US011827899B2

(12) United States Patent
Maguire et al.

(10) Patent No.: US 11,827,899 B2
(45) Date of Patent: *Nov. 28, 2023

(54) VECTOR-FREE DELIVERY OF GENE EDITING PROTEINS AND COMPOSITIONS TO CELLS AND TISSUES

(71) Applicant: Avectas Limited, County Kildare (IE)

(72) Inventors: Michael Maguire, Dublin (IE); Shirley O'Dea, Maynooth (IE)

(73) Assignee: Avectas Limited, County Kildare (IE)

( * ) Notice: Subject to any disclaimer, the term of this patent is extended or adjusted under 35 U.S.C. 154(b) by 534 days.

This patent is subject to a terminal disclaimer.

(21) Appl. No.: 16/067,431

(22) PCT Filed: Dec. 22, 2016

(86) PCT No.: PCT/IB2016/001895
§ 371 (c)(1),
(2) Date: Jun. 29, 2018

(87) PCT Pub. No.: WO2017/115128
PCT Pub. Date: Jul. 6, 2017

(65) Prior Publication Data
US 2019/0194691 A1 Jun. 27, 2019

Related U.S. Application Data

(60) Provisional application No. 62/273,284, filed on Dec. 30, 2015.

(51) Int. Cl.
| | | |
|---|---|---|
| C12N 15/63 | (2006.01) |
| C12N 5/00 | (2006.01) |
| C12N 15/87 | (2006.01) |
| C12N 9/22 | (2006.01) |
| C12N 15/113 | (2010.01) |
| B01L 3/00 | (2006.01) |
| B01L 5/00 | (2006.01) |
| C12N 15/11 | (2006.01) |
| A61K 31/70 | (2006.01) |

(52) U.S. Cl.
CPC ............ *C12N 15/87* (2013.01); *B01L 3/527* (2013.01); *B01L 3/567* (2013.01); *B01L 5/00* (2013.01); *C12N 9/22* (2013.01); *C12N 15/11* (2013.01); *C12N 15/113* (2013.01); *B01L 2400/0487* (2013.01); *B01L 2400/06* (2013.01); *C12N 2310/20* (2017.05); *C12N 2320/32* (2013.01); *C12N 2800/80* (2013.01)

(58) Field of Classification Search
CPC ...... C12N 15/87; C12N 15/113; C12N 15/11; C12N 9/22; C12N 2310/20; B01L 3/527; B01L 3/567; B01L 5/00; B01L 2400/0487
See application file for complete search history.

(56) References Cited

U.S. PATENT DOCUMENTS

| | | | |
|---|---|---|---|
| 5,814,331 A | 9/1998 | Holen | |
| 5,877,023 A | 3/1999 | Sautter et al. | |
| 6,093,557 A | 7/2000 | Pui et al. | |
| 6,764,720 B2* | 7/2004 | Pui .......................... | B05B 1/14 |
| | | | 427/2.14 |
| 7,293,559 B2* | 11/2007 | Ganan-Calvo .... | A61M 15/0065 |
| | | | 128/200.14 |
| 7,667,004 B2 | 2/2010 | Zhong et al. | |
| 7,927,874 B2 | 4/2011 | Ikemoto et al. | |
| 8,101,200 B2 | 1/2012 | Whitbourne et al. | |
| 8,697,359 B1 | 4/2014 | Zhang | |
| 8,932,814 B2 | 1/2015 | Cong et al. | |
| 9,023,649 B2 | 5/2015 | Mali et al. | |
| 9,074,199 B1 | 7/2015 | Chavez et al. | |
| 9,079,878 B2 | 7/2015 | Bagal et al. | |
| 10,612,042 B2 | 4/2020 | Maguire et al. | |
| 11,332,757 B2 | 5/2022 | Maguire et al. | |
| 11,447,798 B2 | 9/2022 | Maguire et al. | |
| 2001/0006643 A1 | 7/2001 | Hope | |
| 2002/0018795 A1 | 2/2002 | Whitbourne et al. | |
| 2004/0033589 A1 | 2/2004 | O'Brien | |
| 2004/0213744 A1 | 10/2004 | Lulla et al. | |
| 2004/0219676 A1 | 11/2004 | Held et al. | |
| 2004/0242416 A1 | 12/2004 | Touitou | |
| 2005/0014259 A1 | 1/2005 | Conroy et al. | |
| 2009/0178934 A1 | 7/2009 | Jarvius et al. | |
| 2010/0305505 A1 | 12/2010 | Ducharme et al. | |
| 2012/0135526 A1 | 5/2012 | Greenberg | |

(Continued)

FOREIGN PATENT DOCUMENTS

| | | |
|---|---|---|
| JP | H03-251187 A | 11/1991 |
| JP | H06-62871 A | 3/1994 |

(Continued)

OTHER PUBLICATIONS

Beerli et al. (Dec. 8, 1998) "Toward Controlling Gene Expression at Will: Specific Regulation of the erbB-2/HER-2 Promoter by Using Polydactyl Zinc Finger Proteins Constructed from Modular Building Blocks", Proceedings of the National Academy of Sciences, 95(25):14628-14633.

Bhakta et al. (Genome Research) "Highly Active Zinc-finger Nucleases by Extended Modular Assembly", 2013, 23:530-538.

Boch et al. (2009) "Breaking the Code of DNA Binding Specificity of TAL-Type III Effectors", Science, 326(5959):1509-1512.

Branzei et al. (Apr. 2008) "Regulation of DNA Repair Throughout the Cell Cycle", Nature Reviews Molecular Cell Biology, 9(4):297-308.

Burger et al. (2016) "Maximizing Mutagenesis with Solubilized CRISPR-Cas9 Ribonucleoprotein Complexes", Development, 143(11):2025-2037.

(Continued)

*Primary Examiner* — Quang Nguyen
(74) *Attorney, Agent, or Firm* — Mintz Levin Cohn Ferris Glovsky and Popeo, P.C.

(57) ABSTRACT

The present subject matter provides a method for delivering a gene editing composition across a plasma membrane of a cell. Related apparatus, system, techniques, compositions, and articles are also described.

10 Claims, 33 Drawing Sheets

Specification includes a Sequence Listing.

(56) References Cited

U.S. PATENT DOCUMENTS

| | | |
|---|---|---|
| 2013/0053794 A1 | 2/2013 | Cadden et al. |
| 2013/0309677 A1 | 11/2013 | Blackman et al. |
| 2014/0349402 A1* | 11/2014 | Cooper .......... A61K 39/001119 |
| | | 435/455 |
| 2015/0044751 A1 | 2/2015 | Chiou et al. |
| 2015/0071903 A1* | 3/2015 | Liu ...................... C12N 9/1241 |
| | | 424/94.3 |
| 2015/0111216 A1 | 4/2015 | Delahunt et al. |
| 2016/0102322 A1* | 4/2016 | Ravinder ............... C12Q 1/686 |
| | | 435/462 |
| 2017/0356011 A1 | 12/2017 | Maguire et al. |
| 2021/0324419 A1 | 10/2021 | Maguire et al. |

FOREIGN PATENT DOCUMENTS

| | | | |
|---|---|---|---|
| JP | 2004-536089 A | 12/2004 | |
| JP | 6779217 B2 | 10/2020 | |
| WO | 92/18164 A1 | 10/1992 | |
| WO | WO-03000174 A2 * | 1/2003 | ......... A61K 48/0033 |
| WO | WO 2009/130187 * | 10/2009 | |
| WO | WO-2010117464 A1 * | 10/2010 | ............ C12N 15/86 |
| WO | 2013/058812 A1 | 4/2013 | |
| WO | 2013/061205 A2 | 5/2013 | |
| WO | 2013142578 A1 | 9/2013 | |
| WO | 2014/033186 A1 | 3/2014 | |
| WO | 2015088643 A1 | 6/2015 | |
| WO | 2015/071474 | 8/2015 | |
| WO | WO 2016/065341 A1 | 4/2016 | |
| WO | 2017/115128 A2 | 7/2017 | |

OTHER PUBLICATIONS

Carr et al. (Dec. 2009) "Genome Engineering", Nature Biotechnology, 27(12):1151-1162.

Cermak et al. (Apr. 14, 2011) "Efficient Design and Assembly of Custom TALEN and other TAL Effector-based Constructs for DNA Targeting", Nucleic Acids Research, 39(12):11 pages.

Chen et al. (Dec. 2003) "Influence of Histidine on the Stability and Physical Properties of a Fully Human Antibody in Aqueous and Solid Forms", Pharmaceutical Research, 20(12):1952-1960.

Chevalier et al. (2001) "Homing Endonucleases: Structural and Functional Insight into the Catalysts of Intron/intein Mobility", Nucleic Acids Research, 29(18):3757-3774.

Cho et al. (Nov. 2013) "Heritable Gene Knockout in Caenorhabditis Elegans by Direct Injection of Cas9-sgRNA Ribonucleoproteins", Genetics, 195(3):1177-1180.

Christian et al. (Oct. 1, 2010) "Targeting DNA Double-Strand Breaks with TAL Effector Nucleases", Genetics, 186(2):757-761.

D'Amico et al. (Feb. 15, 2009) "A Nondetergent Sulfobetaine Improves Protein Unfolding Reversibility in Mlicrocalorimetric Studies", Analytical Biochemistry, 385(2):389-391.

Deng et al. (2012) "Structural Basis for Sequence-specific Recognition of DNA by TAL Effectors", Science, 335(6069):720-723.

Dwyer et al. (1999) "Molecular Simulation of the Effects of Alcohols on Peptide Structure", Biopolymers, 49(7):635-645.

Eyles et al. (Feb. 16, 2010) "Nature's Molecular Sponges: Small Heat Shock Proteins Grow into their Chaperone Roles", Proceedings of the National Academy of Sciences, 107(7):2727-2728.

Ferns et al. (Oct. 2011) "Protection Against Protein Aggregation by Alpha-crystalline as a Mechanism of Preconditioning", Neurochemical Research, 37:244-252.

Fineran et al. (Dec. 2012) "Memory of Viral Infections by CRISPR-Cas Adaptive Immune Systems: Acquisition of New Information", Virology, 434(2):202-209.

Han et al. (Oct. 2007) "Effects of Sugar Additives on Protein Stability of Recombinant Human Serum Albumin During Lyophilization and Storage", Archives of Pharmacal Research, 30(9):1124-1131.

Hsu et al. (Jun. 5, 2014) "Development and Applications of CRISPR-Cas9 for Genome Engineering", Cell, 157(6):1262-1278(34 pages).

Ibarra et al. (Aug. 23, 2016) "Efficient Modification of the CCR5 Locus in Primary Human T Cells With megaTAL Nuclease Establishes HIV-1 Resistance", Molecular Therapy-Nucleic Acids, Article No. e352, 5:10 pages.

Kerwin Bruce A. (Aug. 2008) "Polysorbates 20 and 80 used in the Formulation of Protein Biotherapeutics: Structure and Degradation Pathways", 97(8):2924-2935.

Kim et al. (2014) "Highly Efficient RNA-Guided Genome Editing in Human Cells via Delivery of Purified Cas9 Ribonucleoproteins", Genome Research, 24(6):1012-1019.

Lin et al. (Dec. 15, 2014) "Enhanced Homology-directed Human Genome Engineering by Controlled Timing of CRISPR/Cas9 Delivery", eLife, Article No. e04766, 3:13 pages.

Liu et al. (Oct. 2005) "Trehalose Differentially Inhibits Aggregation and Neurotoxicity of Beta-amyloid 40 and 42", Neurobiology of Disease, 20(1):74-81.

Martin et al. (May 1, 2017) "Efficient Vector-free Engineering of MSC with Retention of Cell Viability and Differentiation Potential", Cytotherapy, 19(5):e23.

Meaking et al. (Dec. 27, 1995) "Electroporation-induced Damage in Mammalian Cell DNA", Biochimica et Biophysica Acta (BBA)—Gene Structure and Expression, 1264(3):357-362.

Miller et al. (Feb. 2011) "A Tale Nuclease Architecture for Efficient Genome Editing", Nature Biotechnology, 29(2):143-148.

Morimoto et al. (2008) "Proteotoxic Stress and Inducible Chaperone Networks in Neurodegenerative Disease and Aging", Genes & Development, 22(11):1427-1438.

Nakamura et al. (2000) "Codon Usage Tabulated from International DNA Sequence Database: Status for the Year 2000", Nucleic Acid Research, 28(1):292.

Ohta et al. (Apr. 2016) "Metabolomic Approach for Improving Ethanol Stress Tolerance in *Saccharomyces cerevisiae*", Journal of Bioscience and Bioengineering, 121(4):399-405.

Omura Tsuneo (1998) "Mitochondria-Targeting Sequence, a Multi-Role Sorting Sequence Recognized at All Steps of Protein Import into Mitochondria", The Journal of Biochemistry, 123(6):1010-1016.

Osborn et al. (Mar. 2016) "Evaluation of TCR Gene Editing Achieved by TALENs, CRISPR/Cas9, and megaTAL Nucleases", Molecular Therapy, 24(3):570-581.

Platts et al. (2015) "Controlling Protein Stability: Mechanisms Revealed using Formulations of Arginine, Glycine and Guanidinium HCL with Three Globular Proteins", International Journal of Pharmaceutics, 486(1-2):131-135.

Reddy et al. (Nov. 2006) "Chaperone-like Activity and Hydrophobicity of a-Crystallin", IUBMB Life, 58 (11):632-641.

Richter et al. (Oct. 20, 2010) "The Heat Shock Response: Life on the Verge of Death", Molecular Cell, 40(2):253-266.

Samuel et al. (2000) "Proline Inhibits Aggregation During Protein Refolding", Protein Science, 9(2):344-352.

Sather et al. (Sep. 30, 2015) "Efficient Modification of CCR5 in Primary Human Hematopoietic Cells Using a megaTAL Nuclease and AAV Donor Template", Science Translational Medicine, 7(307):307ra156(29 pages).

Schumann et al. (Aug. 18, 2015) "Generation of Knock-in Primary Human T Cells using Cas9 Ribonucleoproteins", Proceedings of the National Academy of Sciences, 112(33):10437-10442.

Stengel et al. (Feb. 2, 2010) "Quaternary Dynamics and Plasticity Underlie Small Heat Shock Protein Chaperone Function", Proceedings of the National Academy of Sciences, 107(5):2007-2012.

Sung et al. (Nov. 2013) "Highly Efficient Gene Knockout in Mice and Zebrafish with RNA-guided Endonucleases", Genome Research, 24(1):125-131.

Wang et al. (Mar. 25, 2014) "Progressive Engineering of a Homing Endonuclease Genome Editing Reagent for the Murine X-linked Immunodeficiency Locus", Nucleic Acids Research, 42(10):6463-6475.

Whitley et al. (Apr. 1999) "Heat Shock Proteins: A Review of the Molecular Chaperones", Journal of Vascular Surgery, 29(4):748-751.

Wiedenheft et al. (Feb. 15, 2012) "RNA-Guided Genetic Silencing Systems in Bacteria and Archaea", Nature, 482(7385):331-338.

(56) References Cited

OTHER PUBLICATIONS

Xie et al. (1997) "Mechanism of the Stabilization of Ribonuclease A by Sorbitol: Preferential Hydration is Greater for the Denatured then for the Native Protein", Protein Science, 6(1):211-221.
Young et al. (Dec. 5, 2005) "Gelatin as a Delivery Vehicle for the Controlled Release of Bioactive Molecules", Journal of Controlled Release, 109(1-3):256-274.
Gaj et al. (2016) "Genome-Editing Technologies: Principles and Applications", Cold Springs Harb Perspect Biol, 8:a023754.
Gruber et a. (2008) "The Vienna RNA Websuite", Nucleic Acids Research, 36:W70-W74.
Elhissi et al. (2011) "Vibrating-Mesh Nebulization of Liposomes Generated Using an Ethanol-Based Proliposome Technology", Journal of Liposome Research, 21(2):173-180.
Gurtovenko et al. (Oct. 2010) "Defect-Mediated Trafficking across Cell Membranes: Insights from in Silico Modeling", Chemical Reviews, 110(10):6077-6103.
Gurtovenko et al. (2009) "Interaction of Ethanol with Biological Membranes: The Formation of Non-bilayer Structures within the Membrane Interior and their Significance", The Journal of Physical Chemistry, Part B, 113 (7):1983-1992.
Hapala Ivan, (1997) "Breaking the Barrier: Methods for Reversible Permeabilization of Cellular Membranes", Critical Reviews in Biotechnology, 17(2):105-122.
Lemoine et al. (May 12, 2005) "Mechanism of Efficient Transfection of the Nasal Airway Epithelium by Hypotonic Shock", Gene Therapy, 12(16):1275-1282.
Medepalli et al. (May 12, 2005) "A New Technique for Reversible Permeabilization of Live Cells for Intracellular Delivery of Quantum Dots", Nanotechnology, 205101, 24(20):13 Pages.
Papapetrou et al. ( Oct. 2005) "Genetic Modification of Hematopoietic Stem Cells with Nonviral Systems: Past Progress and Future Prospects", Gene Therapy, 12:S118-S130.
Van De Ven et al. (2009) "Delivery of Optical Contrast Agents Using Triton-X100, Part 1: Reversible Permeabilization of Live Cells for Intracellular Labeling", Journal of Biomedical Optics, 14(2):17 Pages.
Van De Ven et al. (2009) "Delivery of Optical Contrast Agents Using Triton-X100, Part 2: Enhanced Mucosal Permeation for the Detection of Cancer Biomarkers", Journal of Biomedical Optics, 14(2):22 Pages.
Besser MJ, et al., "Modifying lnterleukin-2 Concentrations During Culture Improves Function of T Cells for Adoptive Immunotherapy", Cytotherapy, 2009, vol. 11, No. 2, 206-217.
Brocard , et al., "Peroxisome Targeting Signal 1: Is it Really a Simple Tripeptide?", Biochimica et Biophysica Acta (BBA)—Molecular Cell Research, Dec. 2006, 1763(12):1565-1573.
Cho , et al., "Targeted Genome Engineering in Human Cells with the Cas9 RNA-Guided Endonuclease", Nature Biotechnology, Mar. 2013, 31(3):230-232.
D'Astolfo , et al., "Efficient Intracellular Delivery of Native Proteins", Cell, Apr. 23, 2015, 161(3):674-690.
Dingwall , et al., "Nuclear Targeting Sequences—A Consensus?", Trends in Biochemical Sciences, Dec. 1991, 16(12):478-481.
Jinek , et al., "A Programmable Dual-RNA-Guided DNA Endonuclease in Adaptive Bacterial Immunity", Science, Aug. 17, 2012, 337(6069)1816-821.
Kalderon Daniel, et al., "A Short Amino Acid Sequence Able to Specify Nuclear Location", Biochemistry Division, National Institute for Medical Research, Dec. 1984, Cell, vol. 39 ( Pt 2):499-509.
Makkerh , et al., "Comparative Mutagenesis of Nuclear Localization Signals Reveals the Importance of Neutral and Acidic Amino Acids", Current Biology, Aug. 1996, 6(8):1025-1027.
Park, et al., "Engineering Mesenchymal Stem Cells for Regenerative Medicine and Drug Delivery", Methods, Aug. 2015, 84:3-16.
Rapaport, Doron , "Finding the Right Organelle. Targeting Signals in Mitochondrial Outer-Membrane Proteins", EMBO Reports, Nov. 2003, 4(10):948-952.
Scott, et al., "NoD: A Nucleolar Localization Sequence Detector for Eukaryotic and Viral Proteins", BMC Bioinformatics, Aug. 3, 2011, 12:317.
Zuris , et al., "Efficient Delivery of Genome-Editing Proteins In Vitro and In Vivo", Nature Biotechnology, Jan. 2015, 33(1):73-80.
X. Han et al., CRISPR-Cas9 Delivery to Hard-to-Transfect cells via membrane deformation, Science Advances, vol. 1, No. 7, Aug. 14, 2015, pp. e1500454-e1500454, XP055339291.
O'Dea Shirley et al., Transfection of 'Hard to Transfect Cells Using Electrospray: Sprayfection, Molecular Therapy, vol. 20, No. Suppl. 1, May 2012, pp. S241, & 15th Annual Meeting of the American-Society of Genes and Cell Therapy (ASGCT), Philadelphia, PA, USA May 16, 2012.
O'Dea Shirley et al., Vector-Free Intracellular Delivery by Reversible Permeabilization, Plos One, vol. 12, No. 3, E0174779, Mar. 30, 2017, pp. 1-23, XP002770129, ISSN: 1932-6203, DOI: 10.1371/journal.pne.0174779.
Li Ling et al., Challenges in CRISPR/CAS9 Delivery: Potential Roles of Nonviral Vectors, Human Gene Therapy, Vo. 26, No. 7, Jul. 2015, pp. 452-462.
Xiquan Liang et al., Rapid and Highly Efficient Mammalian Cell Engineering via Cas9 Protein Transfection, Journal of Biotechnology, vol. 208, May 21, 2015, pp. 44-53, XP055196365, ISSN: 0168-1656, DOI: 10.106/j.jbiotec.2015-04-024.

* cited by examiner

Scheme

FIG. 6

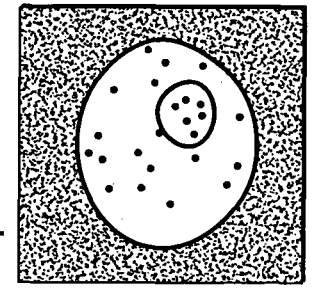
Step 1

A population of suspension or adherent cells can be modified within 4 minutes.

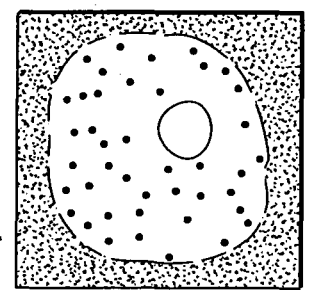
Step 2

The cargo is mixed with the proprietary delivery solution and applied to the cells with precise control of volume and application time.

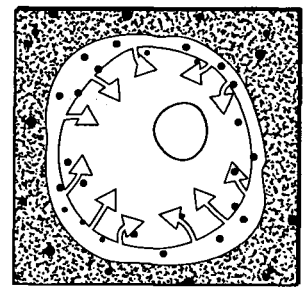
Step 3

The delivery solution gently permeabilizes the cell membrane and the cargo rapidly diffuse into the cell.

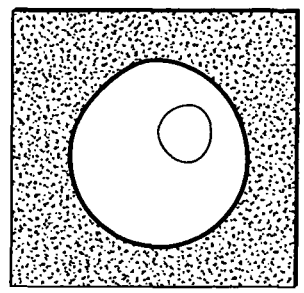
Step 4

The permeabilization solution is replaced with a recovery solution which results in high cell viability and functionality levels.

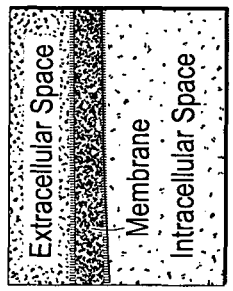
Step 1

A population of suspension or adherent cells can be modified within 4 minutes.

Step 2

The cargo is mixed with the proprietary delivery solution and applied to the cells with precision control.

Step 3

The delivery solution gently permeabilizes the cell membrane allowing rapid diffusion of cargo into the cell.

Step 4

Cell permeabilization is rapidly reversed with a stop solution preserving cell viability and functionality.

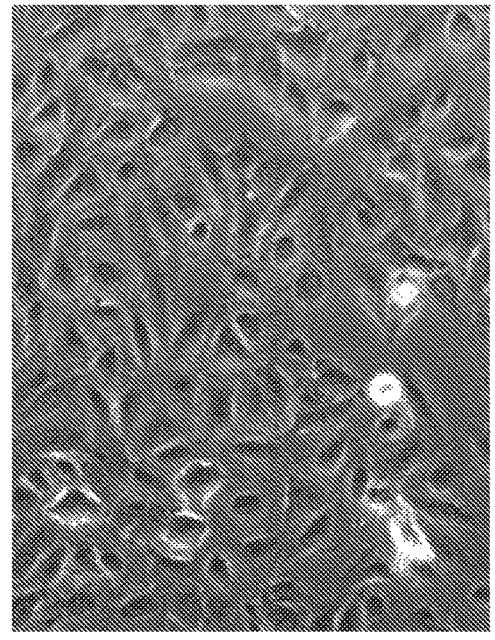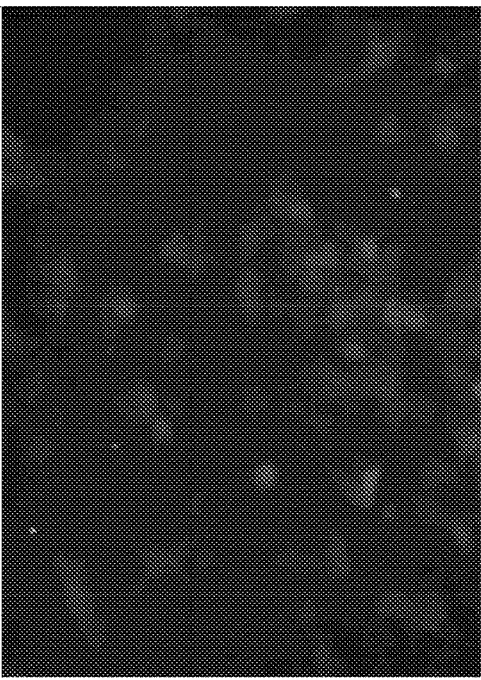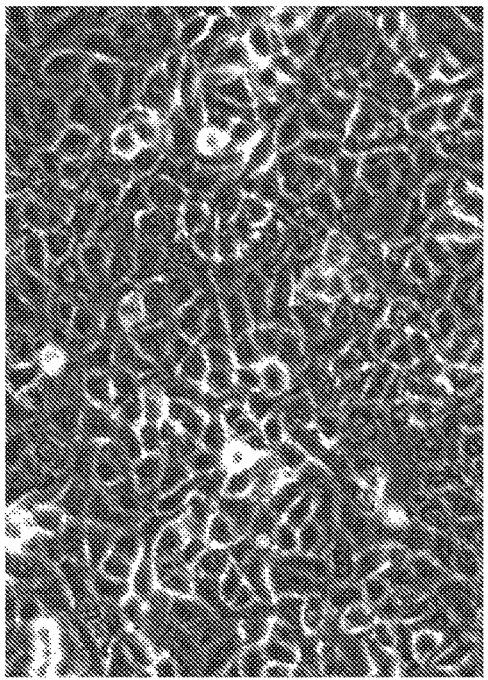
FIG. 8

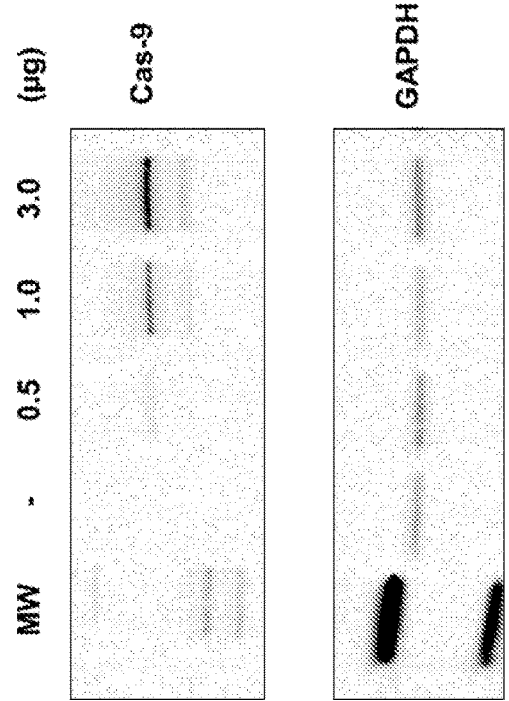
FIG. 10A  A549
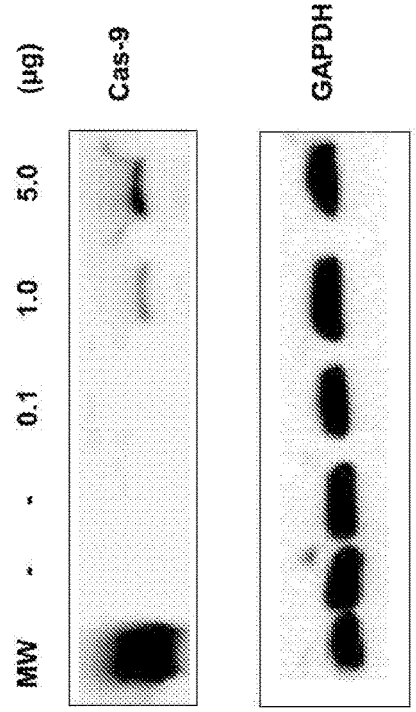
FIG. 10B  Jurkat (24 hr)

Cas9-Cy3

Anti-Cas9 Ab

Dual-RNA1-FAM

RNP-FAM

RNP
Anti-Cas9 Ab

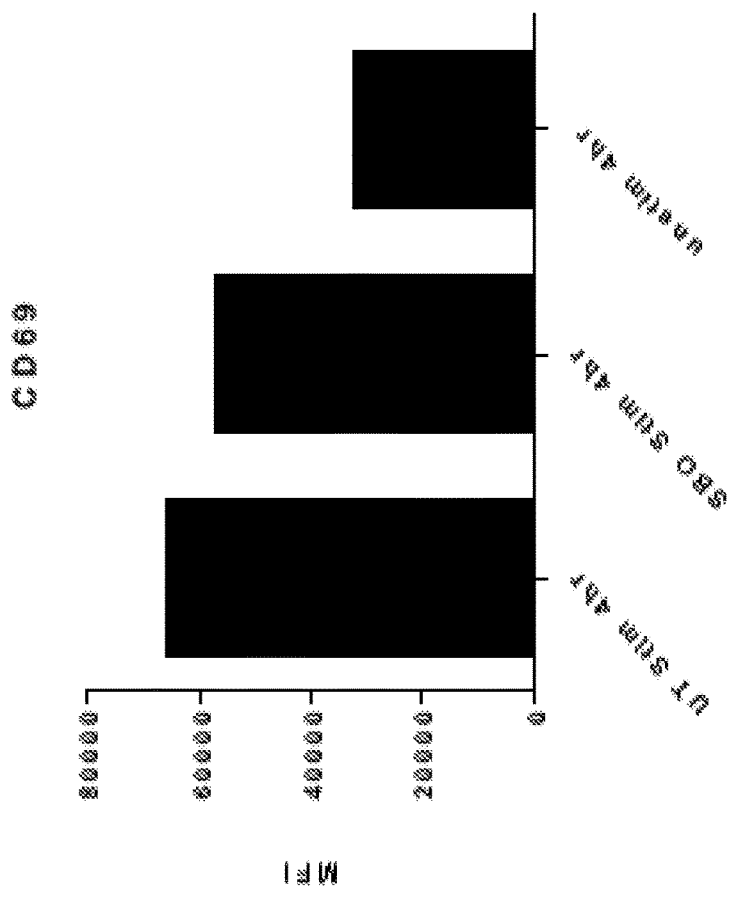
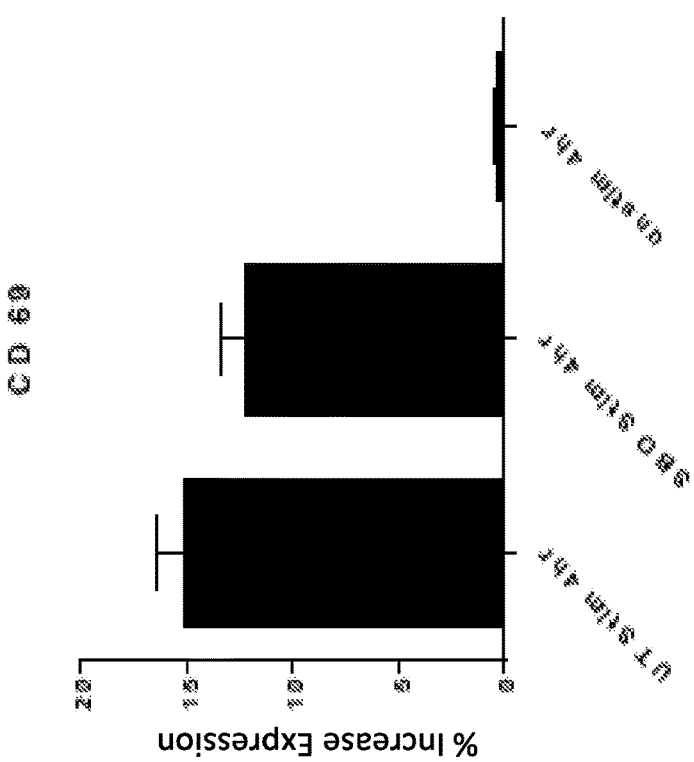
FIG. 14A

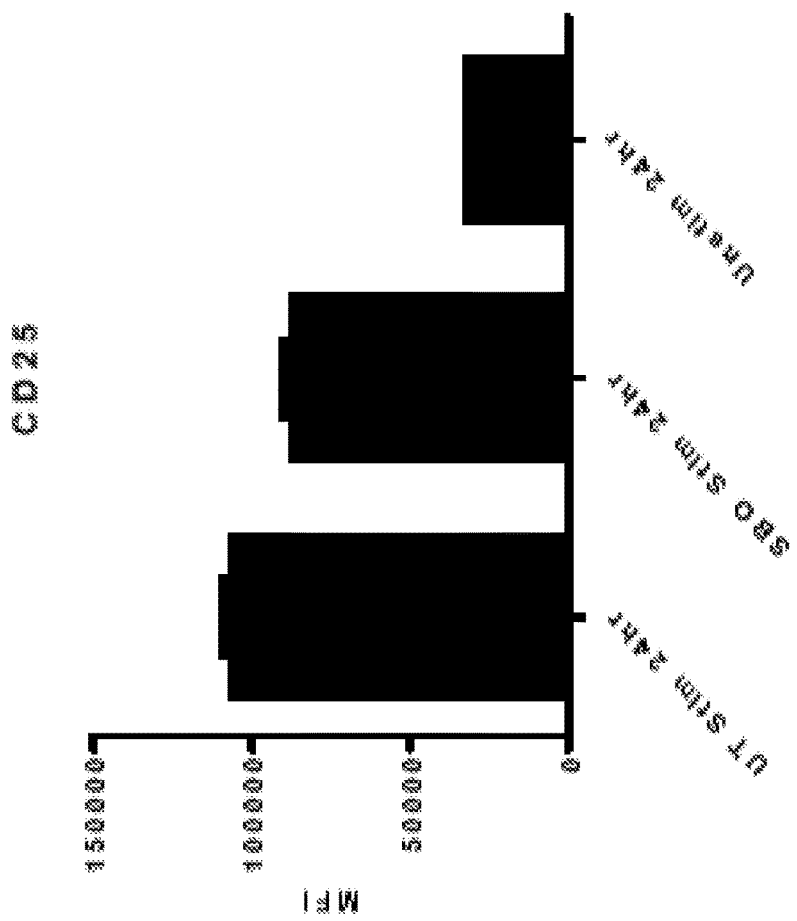
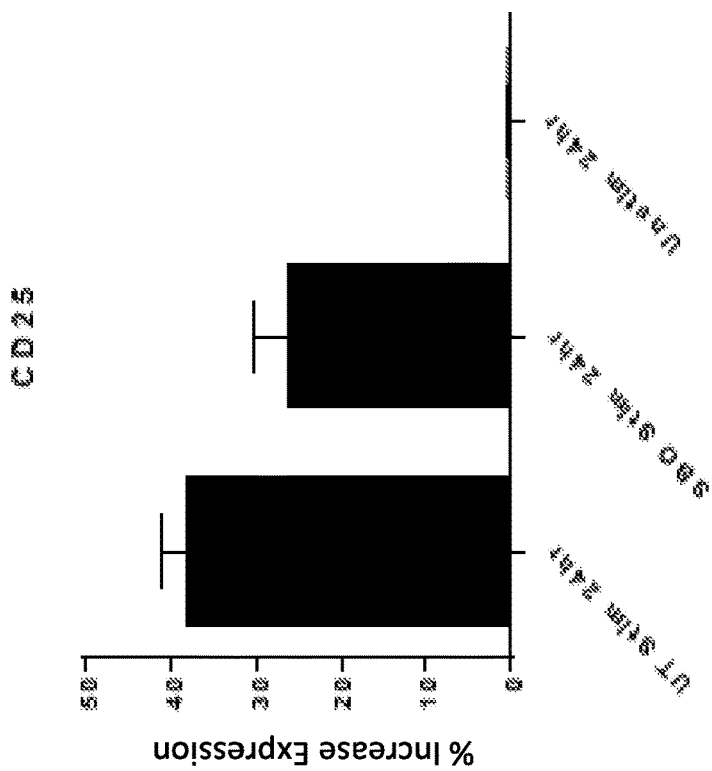
FIG. 14B

MDKKYSIGLDIGTNSVGWAVITDEYKVPSKKFKVLGNTDRHSIKKNLIGALLFDSGETAE
ATRLKRTARRRYTRRKNRICYLQEIFSNEMAKVDDSFHRLEESFLVEEDKKHERHPIFG
NIVDEVAYHEKYPTIYHLRKKLVDSTDKADLRLIYLALAHMIKFRGHFLIEGDLNPDNSD
VDKLFIQLVQTYNQLFEENPINASGVDAKAILSARLSKSRRLENLIAQLPGEKKNGLEGN
LIALSLGLTPNFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEIFFDSKNGYA
GYIDGGASQEEFYKFIKPILEKMDGTEELLVKLNREDLLRKQRTFDNGSIPHQIHLGELH
AILRRQEDFYPFLKDNREKIEKILTFRIPYYVGPLARGNSRFAWMTRKSEETITPWNFEE
VVDKGASAQSFIERMTNFDKNLPNEKVLPKHSLLYEYTVYNELTKVKVYVTEGMRKPAFL
SGEQKKAIVDLLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQLKRRYTGWG
RLSRKLINGIRDKQSGKTILDFLKSDGFANRNFMQLIHDDSLTFKEDIQKAQVSGQGDSL
HEHIANLAGSPAIKKGILQTVKVVDELVKVMGRHKPENIVIEMARENQTTQKGQKNSRER
MKRIEEGIKELGSQILKEHPVENTQLNEKLYLYLQNGRDMYVDQELDINRLSDYDVDH
IVPQSFLKDDSIDNKVLTRSDKNRGKSDNVPSEEVKKMKNYWRQLLNAKLITQRKFDNL
TKAERGGLSELDKAGFIKRQLVETRQITKHVAQILDSRMNTKYDENDKLIREVKVITLKS
KLVSDFRKDFQFYKVREINNYHHAHDAYLNAVVGTALIKKYPKLESEFVYGDYKVYDVRK
MIAKSEQEIGKATAKYFFYSNIMNFKTEITLANGEIRKRPLIETNGETGEIVWDKGRDF
ATVRKVLSMPQVNIVKKTEVQTGGFSKESILPKRNSDKLIARKKDWDPKKYGGFDSPTVA
YSVLVVAKVEKGKSKKLKSVKELLGTIMERSSFEKNPIDFLEAKGYKEVKKDLIIKLPK
YSLFELENGRKRMLASAGELQKGNELALPSKYVNFLYLASHYEKLKGSPEDNEQKQLFVE
QHKHYLDEIIEQISEFSKRVILADANLDKVLSAYNKHRDKPIREQAENIIHLFTLTNLGA
PAAFKYFDTTIDRKRYTSTKEVLDATLIHQSITGLYETRIDLSQLGGDGSGPPKKKRKV
YPYDVPDYA*

(SEQ ID NO: 4)

FIG. 15

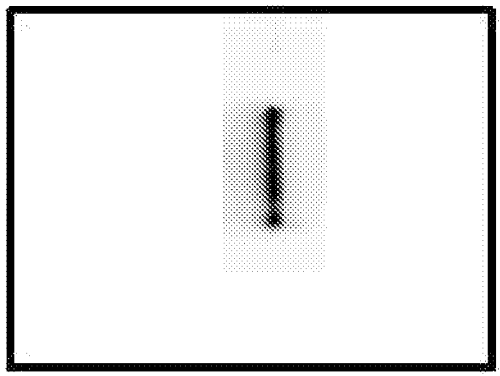
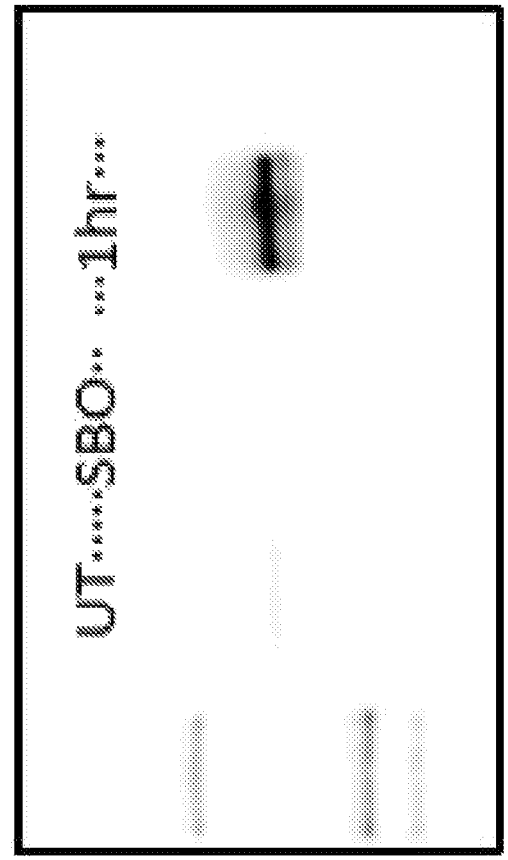
FIG. 16

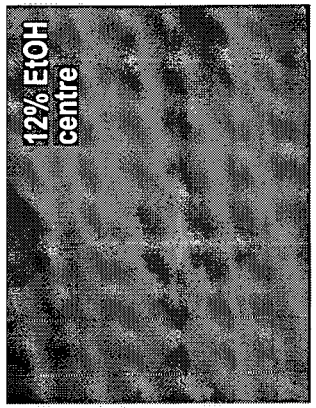
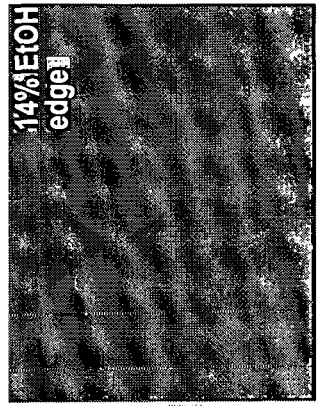
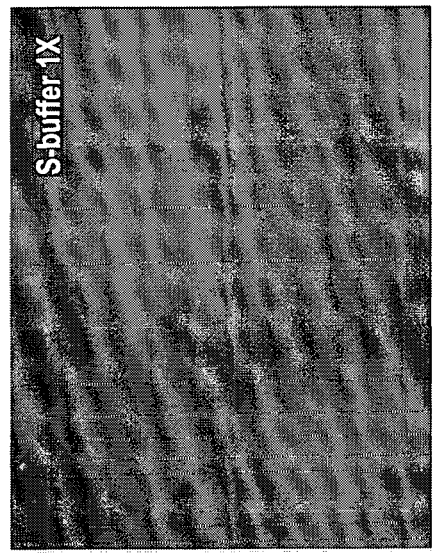
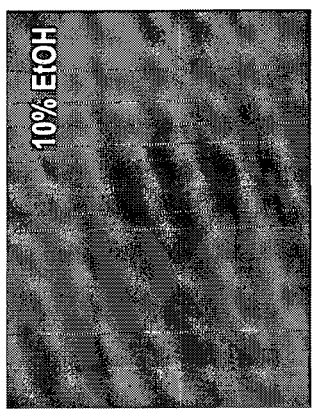
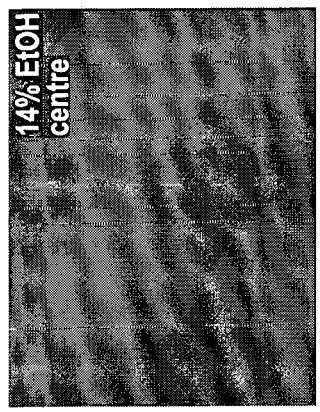
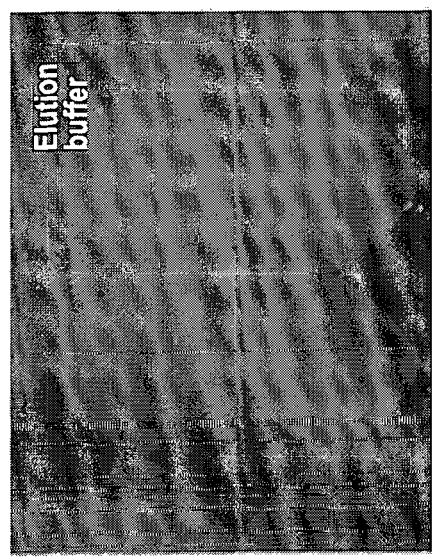
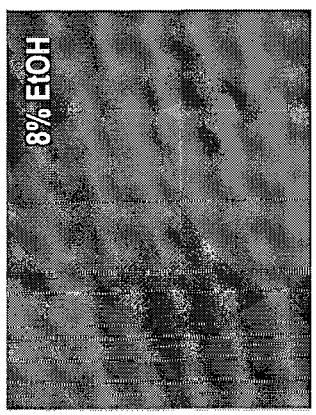
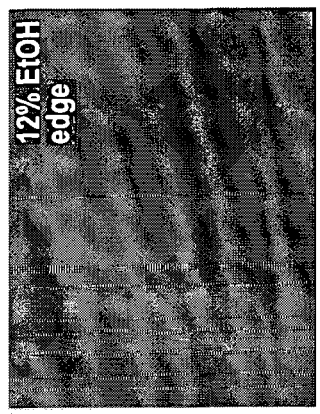
FIG. 23
FIG. 24

VECTOR-FREE DELIVERY OF GENE EDITING PROTEINS AND COMPOSITIONS TO CELLS AND TISSUES

RELATED APPLICATIONS

This application is a National Stage Application, filed under 35 U.S.C. § 371, of International Application No. PCT/M2016/001895 filed Dec. 22, 2016, which claims the benefit of priority to U.S. Provisional Application No. 62/273,284, filed Dec. 30, 2015, the entire contents of each of which are incorporated herein by reference.

TECHNICAL FIELD

The subject matter described herein relates to vector-free delivery of gene editing compounds and complexes to cells and tissues.

INCORPORATION-BY-REFERENCE OF SEQUENCE LISTING

The contents of the text file named "048831_506N01US_ST25.txt", which was created on Jun. 29, 2018 and is 65,837 bytes is size, is hereby incorporated by reference in its entirety.

BACKGROUND

The clustered regularly interspaced short palindromic repeat (CRISPR)-Cas genome engineering system (hereinafter the "CRISPR-Cas system") enables researchers to modify genomic DNA inside cells. Three components are required for this system: Cas9, which may be derived from *Streptococcus pyogenes*, is an endonuclease that is complexed with CRISPR RNA (crRNA) and trans-activating crRNA (tracrRNA) to form an RNA-guided endonuclease (RGEN). These RGENs cleave chromosomal DNA in cells, producing site-specific double-strand breaks (DSBs). Repair of these DSBs can occur via endogenous high-fidelity homologous recombination (HR) or error-prone non-homologous end joining (NHEJ) resulting in targeted mutagenesis and chromosomal rearrangements. The specificity of the RGEN is determined by Watson-Crick base pairing between the crRNA and the target DNA and by Cas9 recognition of the NGG-trinucleotide protospacer adjacent motif (PAM). crRNA and tracrRNA can be fused to form a single-guide RNA (gRNA or sgRNA). A major advantage of CRISPR-Cas9 over other genome editing nucleases is the ability to readily reprogram the specificity of Cas9 by replacing the crRNA, in contrast to zinc finger nucleases (ZFNs) and transcription activator-like effector nucleases (TALENs) whose DNA-targeting specificities must be altered by protein engineering strategies.

The CRISPR-Cas system has been most commonly delivered into cells in the form of plasmid DNA, which encodes for the three components, either as separate or combined plasmids. But plasmids are associated with off-target edits. Plasmids can also integrate randomly in the genome or at Cas9-generated sites. While the latter event can at least be predicted and monitored, the former can be difficult to detect and so can be more problematic. Regardless of the site of integration, these foreign sequences can cause host immune responses, which creates challenges for the use of gene-edited stem cells or primary cells in clinical applications. Furthermore, cells transfected with plasmids for clinical applications are regarded as genetically modified by regulatory authorities and as such are subject to lengthy and costly regulatory procedures.

SUMMARY OF THE INVENTION

The devices, methods, and systems described below solve many of the problems and drawbacks associates with previous gene-editing approaches by providing a reliable and efficient system for delivering the building blocks, e.g., proteins or gene editing complexes, of a gene editing system thereby avoiding delivery of plasmid DNA or other vectors encoding such proteins. The present system also provides advantages over other approaches such as electroporation, magnetofection, liposome-mediated transfection, lentiviral-mediated transfection, or intracellular injection methods Although several gene editing systems use a DNA plasmid form of the Cas9 and the guide RNAs, the invention described herein delivers the RNP [e.g., (gene editing protein(s) and guide RNA (s)] to achieve a more transient gene editing effect, thus leading to fewer off-target effects. Although electroporation can be used to deliver proteins, e.g., gene editing proteins, to cells, the methods, systems, and compositions described herein offer several advantages compared to electroporation. For example, the ethanol-mediated spray delivery system of the invention delivers gene editing proteins and complexes with greater efficiency, e.g., 10%, 20%, 50%, 75%, 2-fold or more, compared to electroporation and with comparable or better viability of the cells after delivery and comparable or better gene editing efficiency compared to electroporation. Moreover, cell function, e.g., differentiation of stem cells or activation of immune cells, is better preserved (e.g., 10%, 20%, 50%, 75%, 2-fold or more) using the ethanol spray methods described compared to electroporation. In addition unlike the system described herein, other methods such as liposome-mediated transfection or electroporation, the latter approaches require that adherent cells be detached from their substratum in order to transfect them using, e.g., a electroporator, and such an extra manipulation step compromises both the sterility and the biology/function of the cells. Moreover, multiple dosing with delivery cargo (gene delivery proteins and/or gene delivery complexes) is not be possible using other methods, e.g., electroporation, due to high levels of cell damage associated with such procedures. The compositions and methods described here permit 2, 3, 4, 5, or more doses (delivery spray, followed by stop solution), a process that increases efficiency delivery of the cargo to cells and amount of those gene editing composition (s) into the target cells. Target cells include primary cells (e.g., those directly cultured from their source organ tissue or obtained from blood) as well as immortalized cells, e.g., cell lines, and adherent cells as well as suspension, e.g., free-floating, cells. Primary human cells are directly cultured from their source organ tissue or blood cells Electroporation is a widely used vector-/carrier-free method but while it can be efficient for delivery of nucleic acids and/or proteins to some cell types, toxicity can be high, particularly in primary cells. Alternative membrane disrupting methods are therefore required. As discussed above, the devices, methods, and systems described herein are advantageous over such other techniques, and in particular advantageous over electroporation.

Aspects of the present subject matter provide methods for delivering a gene editing composition across a plasma membrane of a cell. In preferred embodiments, the method does not comprise a vector, e.g., a lentiviral vector, a liposome, or electroporation. In some embodiments, the method comprises contacting the cells or delivering to the cells plasmid DNA encoding a gene editing protein; in other embodiments, the method does not comprise contacting the cells or delivering to the cells plasmid DNA encoding a gene editing protein. In some embodiments, the method comprises contacting the cells or delivering to the cells RNA encoding a gene editing protein; in other embodiments, the method does not comprise contacting the cells or delivering to the cells RNA encoding a gene editing protein. The methods described here include providing a population of cells and contacting the population of cells with a volume of aqueous solution, e.g., containing gene editing proteins and or complexes. The aqueous solution may comprise the gene editing composition and an alcohol at a concentration of at least about 2%. In various embodiments, the volume is a function of: (i) exposed surface area of the population of cells; or (ii) a number of cells in the population of cells.

Preferably, the solution is delivered to the cells in the form of a spray or mist, e.g., a plurality of 1, 2, 3, 4, 5, 6, 7, 8, 9, 10 or more aqueous particles per cell. For example, the cells are coated with the spray but not soaked or submersed in the delivery compound-containing solution. A spray or mist comprises a liquid that is blown or driven through the air in the form of small drops.

An example of conditions to achieve a coating of a population of coated cells include delivery of a fine particle spray, e.g., the conditions exclude dropping or pipetting a bolus volume of solution on the cells such that a substantial population of the cells are soaked or submerged by the volume of fluid. Thus, the mist or spray comprises a ratio of volume of fluid to cell volume. Alternatively, the conditions comprise a ratio of volume of mist or spray to exposed cell area, e.g., area of cell membrane that is exposed when the cells exist as a confluent or substantially confluent layer on a substantially flat surface such as the bottom of a tissue culture vessel, e.g., a well of a tissue culture plate, e.g., a microtiter tissue culture plate.

Accordingly, there is a need to provide a vector-free e.g., viral vector-free, approach for delivering biologically relevant payloads, e.g., compounds or compositions, across a plasma membrane and into cells. "Cargo" or "payload" are terms used to describe a compound, or composition that is delivered via an aqueous solution across a cell plasma membrane and into the interior of a cell.

In some examples, the aqueous solution comprises alcohol at a concentration between about 2% and about 50%; at least about 2% and less than about 20, 19, 18, 17, 16, or 15%; or at least about 2, 2.5, 3, 3.5, 4, 4.5, 5, 5.5, 6, 6.5, 7. 7.5, 8. 8.5, 9. 9.5, 10, 11, 12, 13, 14, or 15%. In some aspects, the alcohol is at a concentration less than about 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, or 2%. In some aspects, the alcohol, e.g. ethanol, concentration does not exceed 50%. In some aspects, the alcohol, e.g, ethanol, concentration does not exceed 70%. In some examples, the alcohol concentration is about 25%. The alcohol concentration may vary depending on the cell type, for example the alcohol concentration may be 25%, 27% or 33%. For example, certain target cells, e.g., T cells such as primary T cells, are characterized by a higher tolerance for ethanol and maintain viability and functionality after treatment using delivery buffers with greater than 25% ethanol, e.g., 27%, 30%, 33%, 35% or more. NK cells, e.g., primary NK cells, may also have such a tolerance level for the presence/concentration of ethanol in the cargo delivery buffer.

One or more of the following features can be included in any feasible combination. The volume of solution to be delivered to the cells is a plurality of units, e.g., a spray, e.g., a plurality of droplets of aqueous particles. The volume is described relative to an individual cell or relative to the exposed surface area of a confluent or substantially confluent (e.g., at least 75%, at least 80% confluent, e.g., 85%, 90%, 95%, 97%, 98%, 100%) cell population. For example, the volume can be between $6.0 \times 10^{-7}$ microliter per cell and $7.4 \times 10^{-4}$ microliter per cell. The volume is between $4.9 \times 10^{-6}$ microliter per cell and $2.2 \times 10^{-3}$ microliter per cell. The volume can be between $9.3 \times 10^{-6}$ microliter per cell and $2.8 \times 10^{-5}$ microliter per cell. The volume can be about $1.9 \times 10^{-5}$ microliters per cell, and about is within 10 percent. The volume is between $6.0 \times 10^{-7}$ microliter per cell and $2.2 \times 10^{-3}$ microliter per cell. The volume can be between $2.6 \times 10^{9}$ microliter per square micrometer of exposed surface area and $1.1 \times 10^{-6}$ microliter per square micrometer of exposed surface area. The volume can be between $5.3 \times 10^{-8}$ microliter per square micrometer of exposed surface area and $1.6 \times 10^{-7}$ microliter per square micrometer of exposed surface area. The volume can be about $1.1 \times 10^{-7}$ microliter per square micrometer of exposed surface area. The term "about" can be, e.g., within 10 percent, of a stated unit or amount.

Confluency of cells refers to cells in contact with one another on a surface. For example, it can be expressed as an estimated (or counted) percentage, e.g., 10% confluency means that 10% of the surface, e.g., of a tissue culture vessel, is covered with cells, 100% means that it is entirely covered. For example, adherent cells grow two dimensionally on the surface of a tissue culture well, plate or flask. Non-adherent cells can be spun down, pulled down by a vacuum, or tissue culture medium aspiration off the top of the cell population, or removed by aspiration or vacuum removal from the bottom of the vessel.

Contacting the population of cells with the volume of aqueous solution can be performed by gas propelling the aqueous solution to form a spray. The gas can include nitrogen, ambient air, or an inert gas. The spray can include discrete units of volume ranging in size from, 10 nm to 100 µm, e.g., 30-100 µm in diameter. The spray includes discrete units of volume with a diameter of about 30-50 µm. A total volume of aqueous solution of 20 µl can be delivered in a spray to a cell-occupied area of about 1.82 cm², e.g., one well of a 24-well culture plate. A total volume of aqueous solution of 10 µl is delivered to a cell-occupied area of about 0.2-2 cm², e.g, about 0.95 cm². e.g., one well of a 96-well culture plate (area may vary depending on manufacturer of multi-well plate). For example, 10 µl is spray delivered to cell-occupied area of about 1.82 cm² for a 24-well plate, 0.64 cm² for a 48-well plate, and 0.29 cm² for a 96-well plate, with spray delivery volumes adjusted for microtiter plates with more wells and/or smaller approximate cell growth/cell-occupied area per single well of the multi-well plate (additional examples shown below). As described above, well size can vary with supplier of plasticware. An average across suppliers is:

24 well=about 2.0 cm²; deliver 20 µl
48 well=about 0.8 cm²; deliver 5 µl
96 well=about 0.3 cm²; deliver 2.5 µl In this example, the volume of solution that lands in each well size was measured. A ratio of 'volume to surface area' or 'volume to cell number' is generally used.

In another aspect, the culture plate can include sample wells selected from 1, 6, 9, 12, 24, 48, 96, 384, and 1536 wells, in particular examples the culture plate has 96 sample wells. The diameter of the sample well may range from 0.1 mm to 100 mm; for example, a 24-well culture plate may have a diameter of about 15.6 mm, a 48-well culture plate may have a diameter of about 11 mm and a 96-well culture plate may have a diameter of about 6.4 mm. Approximate well dimensions and spray delivery volumes are shown below.

| Microtiter Plate | Single Well Approx. Diameter (Bottom-mm) | Single Well Approx. Growth Area (cm$^2$) | Delivery spray Volume per single well |
|---|---|---|---|
| 1536 Well Plate | 1.63 × 1.63* | 0.025 | 0.1-10 μl |
| 384 Well Plate | 2.7 × 2.7* | 0.056 | 0.1-10 μl |
| 96 Well Plate | 6.4 | 0.32 | 10 μl** |
| 48 Well Plate | 11 | 0.64 | 10 μl |

*square wells;
**2.5 μl as determined by the volume of solution that lands in each well size (see above)

Typically, the aqueous solution includes a payload to be delivered across a cell membrane and into cell, and the second volume is a buffer or culture medium that does not contain the payload. Alternatively, the second volume (buffer or media) can also contain payload. In some embodiments, the aqueous solution includes a payload and an alcohol, and the second volume does not contain alcohol (and optionally does not contain payload). The population of cells can be in contact with said aqueous solution for 0.01-10 minutes, e.g., 0.1-10 minutes, prior to adding a second volume of buffer or culture medium to submerse or suspend said population of cells. The buffer or culture medium can be phosphate buffered saline (PBS). The population of cells can be in contact with the aqueous solution for 2 seconds to 5 minutes prior to adding a second volume of buffer or culture medium to submerse or suspend the population of cells. The population of cells can be in contact with the aqueous solution, e.g., containing the payload, for 30 seconds to 2 minutes prior to adding a second volume of buffer or culture medium, e.g., without the payload, to submerse or suspend the population of cells. The population of cells can be in contact with a sprayed solution for about 1-2 minutes prior to adding the second volume of buffer or culture medium to submerse or suspend the population of cells. In some examples, preparation of the aqueous solution is less than about 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 minute before delivery.

In some embodiments, addition of the alcohol to the aqueous solution may be after 5, 10, 15, 20, 25, 30, 45 minutes of incubation (for example, at 20-30 minutes).

During the time between spraying of cells and addition of buffer or culture medium, the cells remain hydrated by the layer of moisture from the spray volume.

The gene editing composition may include a compound that edits genomic DNA. For example, the gene editing composition may include a compound or complex that cleaves, nicks, splices, rearranges, translocates, recombines, or otherwise alters genomic DNA. Alternatively or in addition, a gene editing composition may include a compound that (i) may be included a gene-editing complex that cleaves, nicks, splices, rearranges, translocates, recombines, or otherwise alters genomic DNA; or (ii) may be processed or altered to be a compound that is included in a gene-editing complex that cleaves, nicks, splices, rearranges, translocates, recombines, or otherwise alters genomic DNA. In various embodiments, the gene editing composition comprises one or more of (a) gene editing protein; (b) RNA molecule; and/or (c) ribonucleoprotein (RNP).

In some embodiments, the gene editing composition comprises a gene editing protein, and the gene editing protein is a zinc finger nuclease (ZFN), a transcription activator-like effector nuclease (TALEN), a Cas protein, a Cre recombinase, a Hin recombinase, or a Flp recombinase. In additional embodiments, the gene editing protein may be a fusion proteins that combine homing endonucleases with the modular DNA binding domains of TALENs (megaTAL). For example, megaTAL may be delivered as a protein or alternatively, a mRNA encoding a megaTAL protein is delivered to the cells.

In various embodiments, the gene editing composition comprises a RNA molecule, and the RNA molecule comprises a sgRNA, a crRNA, and/or a tracrRNA.

In certain embodiments, the gene editing composition comprises a RNP, and the RNP comprises a Cas protein and a sgRNA or a crRNA and a tracrRNA.

Aspects of the present subject matter are particularly useful for controlling when and for how long a particular gene-editing compound is present in a cell.

In various implementations of the present subject matter, the gene editing composition is detectable in a population of cells, or the progeny thereof, for (a) about 0.5, 1, 2, 3, 4, 5, 6, 7, 8, 9, 10, 12, 24, 48, 60, 72, 0.5-2, 0.5-6, 6-12 or 0.5-72 hours after the population of cells is contacted with the aqueous solution, or (b) less than about 0.5, 1, 2, 3, 4, 5, 6, 7, 8, 9, 10, 12, 24, 48, 60, 72, 0.5-2, 0.5-6, 6-12 or 0.5-72 hours after the population of cells is contacted with the aqueous solution.

In some embodiments, the genome of cells in the population of cells, or the progeny thereof, comprises at least one site-specific recombination site for the Cre recombinase, Hin recombinase, or Flp recombinase.

Aspects of the present invention relate to cells that comprise one gene editing compound, and inserting another gene editing compound into the cells. For example, one component of an RNP could be introduced into cells that express or otherwise already contain another component of the RNP. For example, cells in a population of cells, or the progeny thereof, may comprise a sgRNA, a crRNA, and/or a tracrRNA. In some embodiments the population of cells, or the progeny thereof, expresses the sgRNA, crRNA, and/or tracrRNA. Alternatively or in addition, cells in a population of cells, or the progeny thereof, express a Cas protein.

Various implementations of the subject matter herein include a Cas protein. In some embodiments, the Cas protein is a Cas9 protein or a mutant thereof. Exemplary Cas proteins (including Cas9 and non-limiting examples of Cas9 mutants) are described herein.

In various aspects, the concentration of Cas9 protein may range from about 0.1 to about 25 μg. For example, the concentration of Cas9 may be about 1 μg, about 5 μg, about 10 μg, about 15 μg, or about 20 μg. Alternatively, the concentration of Cas9 may range from about 10 ng/μL to about 300 ng/μL; for example from about 10 ng/μL to about 200 ng/μl; or from about 10 ng/μL to about 100 ng/μl, or from about 10 ng/μL to about 50 ng/μl.

In certain embodiments, the gene editing composition comprises (a) a first sgRNA molecule and a second sgRNA molecule, wherein the nucleic acid sequence of the first sgRNA molecule is different from the nucleic acid sequence of the second sgRNA molecule; (b) a first RNP comprising a first sgRNA and a second RNP comprising a second sgRNA, wherein the nucleic acid sequence of the first sgRNA molecule is different from the nucleic acid sequence of the second sgRNA molecule; (c) a first crRNA molecule and a second crRNA molecule, wherein the nucleic acid sequence of the first crRNA molecule is different from the nucleic acid sequence of the second crRNA molecule; (d) a first crRNA molecule and a second crRNA molecule, wherein the nucleic acid sequence of the first crRNA molecule is different from the nucleic acid sequence of the second crRNA molecule, and further comprising a tracrRNA molecule; or (e) a first RNP comprising a first crRNA and a tracrRNA and a second RNP comprising a second crRNA and a tracrRNA, wherein the nucleic acid sequence of the first crRNA molecule is different from the nucleic acid sequence of the second crRNA molecule.

In aspects, the ratio of the Cas9 protein to guide RNA may be 1:1, 1:2, 1:3, 1:4, 1:5, 1:6, 1:7, 1:8, 1:9, or 1:10.

In embodiments, increasing the number of times that cells go through the delivery process (alternatively, increasing the number of doses), may increase the percentage edit; wherein, in some embodiments the number of doses may include 1, 2, 3, 4, 5, 6, 7, 8, 9, or 10 doses.

In various embodiments, the first and second sgRNA or first and second crRNA molecules together comprise nucleic acid sequences complementary to target sequences flanking a gene, an exon, an intron, an extrachromosomal sequence, or a genomic nucleic acid sequence, wherein the gene, an exon, intron, extrachromosomal sequence, or genomic nucleic acid sequence is about 1, 2, 3, 4, 5, 6, 10, 20, 30, 40, 50, 60, 70, 80, 90, 100, 1-100, kilobases in length or is at least about 1, 2, 3, 4, 5, 6, 10, 20, 30, 40, 50, 60, 70, 80, 90, 100, 1-100, kilobases in length. In some embodiments, the use of pairs of RNPs comprising the first and second sgRNA or first and second crRNA molecules may be used to create a polynucleotide molecule comprising the gene, exon, intron, extrachromosomal sequence, or genomic nucleic acid sequence.

In certain embodiments, the target sequence of a sgRNA or crRNA is about 12 to about 25, or about 12, 13, 14, 15, 16, 17, 18, 19, 20, 21, 22, 23, 24, 25, 17-23, or 18-22, nucleotides long. In some embodiments, the target sequence is 20 nucleotides long or about 20 nucleotides long.

In various embodiments, the first and second sgRNA or first and second crRNA molecules are complementary to sequences flanking an extrachromosomal sequence that is within an expression vector.

Aspects of the present subject matter relate to the delivery of multiple components of a gene-editing complex, where the multiple components are not complexed together. In some embodiments, gene editing composition comprises at least one gene editing protein and at least one nucleic acid, wherein the gene editing protein and the nucleic acid are not bound to or complexed with each other.

The present subject matter allows for high gene editing efficiency while maintaining high cell viability. In some embodiments, at least about 10, 20, 30, 40, 50, 60, 70, 80, 90, 95, 99%, 1-99%, or more of the population of cells, or the progeny thereof, become genetically modified after contact with the aqueous solution. In various embodiments, at least about 10, 20, 30, 40, 50, 60, 70, 80, 90, 95, 99%, 1-99%, or more of the population of cells, or the progeny thereof, are viable after contact with the aqueous solution.

In certain embodiments, the gene editing composition induces single-strand or double-strand breaks in DNA within the cells. In some embodiments the gene editing composition further comprises a repair template polynucleotide. In various embodiments, the repair template comprises (a) a first flanking region comprising nucleotides in a sequence complementary to about 40 to about 90 base pairs on one side of the single or double strand break and a second flanking region comprising nucleotides in a sequence complementary to about 40 to about 90 base pairs on the other side of the single or double strand break; or (b) a first flanking region comprising nucleotides in a sequence complementary to at least about 20, 25, 30, 35, 40, 45, 50, 60, 70, 80, or 90 base pairs on one side of the single or double strand break and a second flanking region comprising nucleotides in a sequence complementary to at least about 20, 25, 30, 35, 40, 45, 50, 60, 70, 80, or 90 base pairs on the other side of the single or double strand break. Non-limiting descriptions relating to gene editing (including repair templates) using the CRISPR-Cas system are discussed in Ran et al. (2013) Nat Protoc. 2013 November; 8(11): 2281-2308, the entire content of which is incorporated herein by reference. Embodiments involving repair templates are not limited to those comprising the CRISPR-Cas system.

In various implementations of the present subject matter, the volume of aqueous solution is delivered to the population of cells in the form of a spray. In some embodiments, the volume is between $6.0 \times 10^{-7}$ microliter per cell and $7.4 \times 10^{-4}$ microliter per cell. In certain embodiments, the spray comprises a colloidal or sub-particle comprising a diameter of 10 nm to 100 µm. In various embodiments, the volume is between $2.6 \times 10^{-9}$ microliter per square micrometer of exposed surface area and $1.1 \times 10^{-6}$ microliter per square micrometer of exposed surface area.

In some embodiments, the RNP has a size of approximately 100 Å×100 Å×50 Å or 10 nm×10 nm×5 nm. In various embodiments, the size of spray particles is adjusted to accommodate at least about 1, 2, 3, 4, 5, 6, 7, 8, 9, 10, or more RNPs per spray particle.

For example, contacting the population of cells with the volume of aqueous solution may be performed by gas propelling the aqueous solution to form a spray. In certain embodiments, the population of cells is in contact with said aqueous solution for 0.01-10 minutes (e.g., 0.1-10 minutes) prior to adding a second volume of buffer or culture medium to submerse or suspend said population of cells.

In some embodiments, the buffer or culture medium comprises phosphate buffered saline (PBS). In various embodiments, the aqueous solution comprises an ethanol concentration of about 5 to about 50%. In non-limiting examples, said aqueous solution comprises one or more of (a) about 75 to about 98% $H_2O$; (b) about 2 to 50% ethanol; (c) about 6 to about 91 mM sucrose; (d) about 2 to about 35 mM potassium chloride; (e) about 2 to about 35 mM ammonium acetate; (f) about 1 to about 14 mM (4-(2-hydroxyethyl)-1-piperazineethanesulfonic acid) (HEPES); (g) about 0.1 to about 10 mM or a magnesium salt or about 0.5 to about 10 mM magnesium chloride; and/or (h) about 2, 2.1, 2.2, 2.3, 2.4, 2.5, 2.6, 2.7, 2.8, 2.9, or 3 mM of a magnesium salt or magnesium chloride. As shown in FIG. 8, a delivery solution comprising 2.5 mM magnesium chloride showed a surprising increase in delivery efficiency compared to delivery solution not comprising magnesium chloride.

In various embodiments, the population of cells includes at least one of primary or immortalized cells. For example, the population of cells may include mesenchymal stem cells, lung cells, neuronal cells, fibroblasts, human umbilical vein (HUVEC) cells, and human embryonic kidney (HEK) cells, primary or immortalized hematopoietic stem cell (HSC), T cells, natural killer (NK) cells, cytokine-induced killer (CIK) cells, human cord blood CD34+ cells, B cells. Non limiting examples of T cells may include CD8+ or CD4+ T cells. In some aspects, the CD8+ subpopulation of the CD3+ T cells are used. CD8+ T cells may be purified from the PBMC population by positive isolation using anti-CD8 beads. In some aspects primary NK cells are isolated from PBMCs and GFP mRNA may be delivered by platform delivery technology (i.e., 3% expression and 96% viability at 24 hours). In additional aspects, NK cell lines, e.g., NK92 may be used.

Cell types also include cells that have previously been modified for example T cells, NK cells and MSC to enhance their therapeutic efficacy. For example: T cells or NK cells that express chimeric antigen receptors (CAR T cells, CAR NK cells, respectively); T cells that express modified T cell receptor (TCR); MSC that are modified virally or non-virally to overexpress therapeutic proteins that complement their innate properties (eg. delivery of Epo using lentiviral vectors or BMP-2 using AAV-6) (reviewed in Park et al, Methods, 2015 August; 84-16); MSC that are primed with non-peptidic drugs or magnetic nanoparticles for enhanced efficacy and externally regulated targeting respectively (Park et al., 2015); MSC that are functionalised with targeting moieties to augment their homing toward therapeutic sites using enzymatic modification (eg. Fucosyltransferase), chemical conjugation (eg. modification of $SLe^x$ on MSC by using N-hydroxy-succinimide (NHS) chemistry) or non-covalent interactions (eg. engineering the cell surface with palmitated proteins which act as hydrophobic anchors for subsequent conjugation of antibodies) (Park et al., 2015). For example, T cells, e.g., primary T cells or T cell lines, that have been modified to express chimeric antigen receptors (CAR T cells) may further be treated according to the invention with gene editing proteins and or complexes containing guide nucleic acids specific for the CAR encoding sequences for the purpose of editing the gene(s) encoding the CAR, thereby reducing or stopping the expression of the CAR in the modified T cells.

Aspects of the present subject matter also provide a composition for delivering a payload across a plasma membrane of a cell, the composition comprising an aqueous solution including the payload and an alcohol at a concentration of at least 2%. In some embodiments the composition further comprises a magnesium salt. In certain embodiments, the composition comprises about 0.1 to about 10 mM of a magnesium salt or about 0.1 to about 10 mM magnesium chloride. A magnesium salt comprises magnesium ions.

Aspects of the present subject matter further provide a composition for delivering a payload across a plasma membrane of a cell, the composition comprising an aqueous solution including the payload, an alcohol at a concentration of at least 2%, less than about 46 mM of a salt lacking magnesium ions, less than about 121 mM sugar, less than 19 mM buffering agent, and about 0.1 to about 10 mM of a magnesium salt.

In certain embodiments, the buffering agent is a weak acid or a weak base that is effective to adjust or maintain the pH of the aqueous solution at a pH of about 6.5, 6.75, 7, 7.25, 7.5, 7.75, 8, 8.25, or 8.5. In various embodiments, the alcohol is methanol, ethanol, isopropyl alcohol, butanol, or benzyl alcohol. In some embodiments, the salt that lacks a magnesium ion comprises a Na or a K ion. In some embodiments, the salt is NaCl, KCl, $Na_2HPO_4$, $C_2H_3O_2NH_4$, or $KH_2PO_4$. In certain embodiments, the sugar comprises sucrose. The buffering agent comprise, e.g., 4-2-(hydroxyethyl)-1-piperazineethanesulfonic acid, 3-[[1,3-di-hydroxy-2-(hydroxymethyl)propan-2-yl]amino]-2-hydroxy-propane-1-sulfonic acid, 2-[[1,3-dihydroxy-2-(hydroxymethyl)propan-2-yl]amino]ethanesulfonic acid, 3-(N-morpholino)propanesulfonic acid, or piperazine-N,N'-bis(2-ethanesulfonic acid).

Aspects of the present invention provide an apparatus for delivering a gene editing composition across a plasma membrane of a cell. In various embodiments, the apparatus comprises: a pneumatic generator producing gas under a pressure; an atomizer operatively coupled to the pneumatic generator; a reservoir configured to contain a volume of aqueous solution, the aqueous solution including the gene editing composition and an alcohol at greater than 2 percent concentration; and a valve between the pneumatic generator and atomizer. In some embodiments, the valve is switchable between a closed position for preventing the gas under the pressure from activating the atomizer and an open position for allowing the gas under the pressure to activate the atomizer to produce colloidal droplets from the aqueous solution. In various embodiments, the valve has a switching speed less than about 250 milliseconds. In certain embodiments, the atomizer is oriented to contact a population of cells with the aqueous solution and wherein the volume is a function of: (i) exposed surface area of the population of cells; or (ii) a number of cells in the population of cells.

Additional apparatus, systems, methods, compositions, and articles described or illustrated herein are also provided.

In an aspect, delivering a payload across a plasma membrane of a cell includes providing a population of cells and contacting the population of cells with a volume of an aqueous solution. The aqueous solution includes the payload and an alcohol content greater than 5 percent concentration. The volume of the aqueous solution may be a function of exposed surface area of the population of cells, or may be a function of a number of cells in the population of cells.

In another aspect, a composition for delivering a payload across a plasma membrane of a cell includes an aqueous solution including the payload, an alcohol at greater than 5 percent concentration, less than 46 mM salt, less than 121 mM sugar, and less than 19 mM buffering agent. For example, the alcohol, e.g., ethanol, concentration does not exceed 50%.

One or more of the following features can be included in any feasible combination. The volume of solution to be delivered to the cells is a plurality of units, e.g., a spray, e.g., a plurality of droplets or aqueous particles. The volume is described relative to an individual cell or relative to the exposed surface area of a confluent or substantially confluent (e.g., at least 75%, at least 80% confluent, e.g., 85%, 90%, 95%, 97%, 98%, 100%) cell population. For example, the volume can be between $6.0 \times 10^{-7}$ microliter per cell and $7.4 \times 10^{-4}$ microliter per cell. The volume is between $4.9 \times 10^{-6}$ microliter per cell and $2.2 \times 10^{-3}$ microliter per cell. The volume can be between $9.3 \times 10^{-6}$ microliter per cell and $2.8 \times 10^{-5}$ microliter per cell. The volume can be about $1.9 \times 10^{-5}$ microliters per cell, and about is within 10 percent. The volume is between $6.0 \times 10^{-7}$ microliter per cell and $2.2 \times 10^{-3}$ microliter per cell. The volume can be between $2.6 \times 10^{-9}$ microliter per square micrometer of exposed surface area and $1.1 \times 10^{-6}$ microliter per square micrometer of exposed surface area. The volume can be between $5.3 \times 10^{-8}$ microliter per square micrometer of exposed surface area and $1.6 \times 10^{-7}$ microliter per square micrometer of exposed surface area. The volume can be about $1.1 \times 10^{-7}$ microliter per square micrometer of exposed surface area. About can be within 10 percent.

Confluency of cells refers to cells in contact with one another on a surface. For example, it can be expressed as an estimated (or counted) percentage, e.g., 10% confluency means that 10% of the surface, e.g., of a tissue culture vessel, is covered with cells, 100% means that it is entirely covered. For example, adherent cells grow two dimensionally on the surface of a tissue culture well, plate or flask. Non-adherent cells can be spun down, pulled down by a vacuum, or tissue culture medium aspiration off the top of the cell population, or removed by aspiration or vacuum removal from the bottom of the vessel.

Contacting the population of cells with the volume of aqueous solution can be performed by gas propelling the aqueous solution to form a spray. The gas can include nitrogen, ambient air, or an inert gas. The spray can include discrete units of volume ranging in size from, 10 nm to 100 µm, e.g., 30-100 µm in diameter. The spray includes discrete units of volume with a diameter of about 30-50 µm. For example, a total volume of aqueous solution of 20 µl can be delivered in a spray to a cell-occupied area of about 1.9 cm$^2$, e.g., one well of a 24-well culture plate (see also description above regarding volume and well size/area). A total volume of aqueous solution of 10 µl is delivered to a cell-occupied area of about 0.95 cm$^2$, e.g., one well of a 48-well culture plate. Typically, the aqueous solution includes a payload to be delivered across a cell membrane and into cell, and the second volume is a buffer or culture medium that does not contain the payload. Alternatively, the second volume (buffer or media) can also contain payload. In some embodiments, the aqueous solution includes a payload and an alcohol, and the second volume does not contain alcohol (and optionally does not contain payload). The population of cells can be in contact with said aqueous solution for 0.1-10 minutes prior to adding a second volume of buffer or culture medium to submerse or suspend said population of cells. The buffer or culture medium can be phosphate buffered saline (PBS). The population of cells can be in contact with the aqueous solution for 2 seconds to 5 minutes prior to adding a second volume of buffer or culture medium to submerse or suspend the population of cells. The population of cells can be in contact with the aqueous solution, e.g., containing the payload, for 30 seconds to 2 minutes prior to adding a second volume of buffer or culture medium, e.g., without the payload, to submerse or suspend the population of cells. The population of cells can be in contact with a spray for about 1-2 minutes prior to adding the second volume of buffer or culture medium to submerse or suspend the population of cells. During the time between spraying of cells and addition of buffer or culture medium, the cells remain hydrated by the layer of moisture from the spray volume.

The aqueous solution can include an ethanol concentration of 5 to 30%. The aqueous solution can include one or more of 75 to 98% H$_2$O, 2 to 45% ethanol, 6 to 91 mM sucrose, 2 to 35 mM KCl, 2 to 35 mM ammonium acetate, and 1 to 14 mM (4-(2-hydroxyethyl)-1-piperazineethanesulfonic acid) (HEPES).

The population of cells can include adherent cells or non-adherent cells. The adherent cells can include at least one of primary mesenchymal stem cells, fibroblasts, monocytes, macrophages, lung cells, neuronal cells, fibroblasts, human umbilical vein (HUVEC) cells, Chinese hamster ovary (CHO) cells, and human embryonic kidney (HEK) cells or immortalized cells, such as cell lines. The population of cells can include non-adherent cells. The non-adherent cells can include at least one of primary hematopoietic stem cell (HSC), T cells, natural killer (NK) cells, cytokine-induced killer (CIK) cells, human cord blood CD34+ cells, B cells, or cell lines such as the Jurkat T cell line.

The population of cells can be substantially confluent, such as greater than 75 percent confluent. Confluency of cells refers to cells in contact with one another on a surface. For example, it can be expressed as an estimated (or counted) percentage, e.g., 10% confluency means that 10% of the surface, e.g., of a tissue culture vessel, is covered with cells, 100% means that it is entirely covered. For example, adherent cells grow two dimensionally on the surface of a tissue culture well, plate or flask. Non-adherent cells can be spun down, pulled down by a vacuum, or tissue culture medium aspiration off the top of the cell population, or removed by aspiration or vacuum removal from the bottom of the vessel. The population of cells can form a monolayer of cells.

In some embodiments, a composition or solution of the present subject matter comprises an alcohol; a salt; a sugar; a buffering agent; and/or ammonium acetate. The alcohol can be selected from, e.g., methanol, ethanol, isopropyl alcohol, butanol and benzyl alcohol. The salt can be selected from, e.g., NaCl, KCl, Na$_2$HPO$_4$, KH$_2$PO$_4$, and C$_2$H$_3$O$_2$NH. The sugar can include, e.g., sucrose. The buffering agent can include, e.g., 4-2-(hydroxyethyl)-1-piperazineethanesulfonic acid, 3-[[1,3-dihydroxy-2-(hydroxymethyl)propan-2-yl]amino]-2-hydroxypropane-1-sulfonic acid, 2-[[1,3-dihydroxy-2-(hydroxymethyl)propan-2-yl]amino]ethanesulfonic acid, 3-(N-morpholino)propanesulfonic acid, or piperazine-N,N'-bis(2-ethanesulfonic acid). In some examples, the solution or buffer comprises magnesium ions, e.g., magnesium ions are optionally provided in the form of a salt such as MgCl$_2$.

The present subject matter relates to a method for delivering gene-editing compounds and complexes across a plasma membrane. The method of the present subject matter comprises introducing a compound or complex to an aqueous composition to form a matrix; atomizing the matrix into a spray; and contacting the matrix with a plasma membrane.

The example methods described herein include a payload, wherein the payload includes an alcohol. By the term "an alcohol" is meant a polyatomic organic compound including a hydroxyl (—OH) functional group attached to at least one carbon atom. The alcohol may be a monohydric alcohol and may include at least one carbon atom, for example methanol. The alcohol may include at least two carbon atoms (e.g. ethanol). In other aspects, the alcohol comprises at least three carbons (e.g. isopropyl alcohol). The alcohol may include at least four carbon atoms (e.g., butanol), or at least seven carbon atoms (e.g., benzyl alcohol). The example payload may include no more than 50% (v/v) of the alcohol, more preferably, the payload comprises 2-45% (v/v) of the alcohol, 5-40% of the alcohol, and 10-40% of the alcohol. The payload may include 20-30% (v/v) of the alcohol.

Most preferably, the payload includes 25% (v/v) of the alcohol. Alternatively, the payload can include 2-8% (v/v) of the alcohol, or 2% of the alcohol. The alcohol may include ethanol and the payload comprises 5, 10, 20, 25, 30, 40, or 50% (v/v) of the ethanol. Example methods may include methanol as the alcohol, and the payload may include 5, 10, 20, 25, 30, 40, or 50% (v/v) of the methanol. The payload may include 2-45% (v/v) of methanol, 20-30% (v/v), or 25% (v/v) methanol. Preferably, the payload includes 20-30% (v/v) of methanol. Further alternatively, the alcohol is butanol and the payload comprises 2, 4, or 8% (v/v) of the butanol.

In some aspects of the present subject matter, the payload is in a hypotonic solution or buffer. The payload solution may have an osmotic concentration of 171 mOsm/L.

According to example methods, the payload solution has an osmotic concentration of 171 mOsm/L at room temperature.

According to the present subject matter, the payload may include at least one salt. The salt may be selected from NaCl, KCl, $Na_2HPO_4$, $C_2H_3O_2NH_4$ and $KH_2PO_4$. According to example methods, the payload includes each of NaCl, KCl, $Na_2HPO_4$, and $KH_2PO_4$. The payload may include less than 46 mM salt. Further, the payload includes 2-35 mM salt, or 10-15 mM salt (e.g., 12 mM salt). According to example methods, the salt is KCl and the payload includes 2.4, 4.8, 7.2, 9.6, 12, 24, 28.8, or 33.6 mM KCl, and more preferably 12 mM KCl.

According to example methods of the present subject matter, the payload may include a sugar (e.g., a sucrose, or a disaccharide). According to example methods, the payload comprises less than 121 mM sugar, 6-91 mM, or 26-39 mM sugar. Still further, the payload includes 32 mM sugar (e.g., sucrose). Optionally, the sugar is sucrose and the payload comprises 6.4, 12.8, 19.2, 25.6, 32, 64, 76.8, or 89.6 mM sucrose. According to example methods of the present subject matter, the payload may include a buffering agent (e.g. a weak acid or a weak base). The buffering agent may include a zwitterion. According to example methods, the buffering agent is 4-(2-hydroxyethyl)-1-piperazineethanesulfonic acid. The payload may comprise less than 19 mM buffering agent (e.g., 1-15 mM, or 4-6 mM or 5 mM buffering agent). According to example methods, the buffering agent is 4-(2-hydroxyethyl)-1-piperazineethanesulfonic acid and the payload comprises 1, 2, 3, 4, 5, 10, 12, 14 mM 4-(2-hydroxyethyl)-1-piperazineethanesulfonic acid. Further preferably, the payload comprises 5 mM 4-(2-hydroxyethyl)-1-piperazineethanesulfonic acid.

According to example methods of the present subject matter, the payload includes ammonium acetate. The payload may include less than 46 mM ammonium acetate (e.g., between 2-35 mM, 10-15 mM, ore 12 mM ammonium acetate). The payload may include 2.4, 4.8, 7.2, 9.6, 12, 24, 28.8, or 33.6 mM ammonium acetate.

The methods described herein include a second aspect of the present subject matter, where a second payload (e.g. an aqueous solution) including 68 mM NaCl, 1.4 mM KCl, 5 mM $Na_2HPO_4$, and 0.9 mM $KH_2PO_4$ is provided. The pH of the second payload may be pH 7.4.

In various embodiments, the volume of aqueous solution performed by gas propelling the aqueous solution may include, e.g., compressed air (e.g. ambient air). These and other implementations may include inert gases, for example, helium, neon, and argon.

In certain aspects of the present subject matter, the population of cells may include adherent cells (e.g., lung, kidney, immune cells such as macrophages) or non-adherent cells (e.g., suspension cells).

In certain aspects of the present subject matter, the population of cells may be substantially confluent, and substantially may include greater than 75 percent confluent. In preferred implementations, the population of cells may form a single monolayer. Additional non-limiting descriptions of methods, systems, apparatus and devices for delivering compounds across a cell plasma membrane are described in PCT International Patent Application No. PCT/US2015/057247, filed Oct. 23, 2015, the entire content of which is incorporated herein by reference.

The present subject matter further relates to apparatus, systems, techniques and articles for delivery of payloads across a plasma membrane. The present subject matter also relates to an apparatus for delivering payloads such as proteins or protein complexes across a plasma membrane. The current subject matter may find utility in the field of intra-cellular delivery, and has application in, for example, delivery of gene editing compositions to a target site, such as a cell, tissue, or organ.

In some implementations, an apparatus for delivering a payload across a plasma membrane can include an atomizer having at least one atomizer emitter and a support oriented relative to the atomizer. The method may further comprise the step of atomizing the payload prior to contacting the plasma membrane with the payload.

In various embodiments, the atomizer can be selected from, e.g., a mechanical atomizer, an ultrasonic atomizer, an electrospray, a nebuliser, and a Venturi tube. The atomizer can be a commercially available atomizer. The atomizer can be an intranasal mucosal atomization device. The atomizer can be an intranasal mucosal atomization device commercially available from LMA Teleflex of NC, USA. The atomizer can be an intranasal mucosal atomization device commercially available from LMA Teleflex of NC, USA under catalogue number MAD300.

In certain embodiments, the atomizer can be adapted to provide a colloid suspension of particles having a diameter of 30-100 μm prior to contacting the plasma membrane with the payload. In various embodiments, the atomizer can be adapted to provide a colloid suspension of particles having a diameter of 30-80 μm. For example, the atomizer can be adapted to provide a colloid suspension of particles having a diameter of 50-80 μm.

In some embodiments, the atomizer includes a gas reservoir. For example, the atomizer can include a gas reservoir with the gas maintained under pressure. In certain embodiments, the gas is selected from air, carbon dioxide, and helium. In various embodiments, the gas reservoir includes a fixed pressure head generator. In some embodiments, the gas reservoir can be in fluid communication with the atomizer emitter. In various implementations of the present subject matter, the gas reservoir includes a gas guide, which can be in fluid communication with the atomizer emitter. In some embodiments, the gas guide is adapted to allow the passage of gas there through. The gas guide can, e.g., include a hollow body. For example, the gas guide can be a hollow body having open ends. In some embodiments, the gas guide includes a hollow body having first and second open ends. In various embodiments, the gas guide is a hollow body having first and second opposing open ends. In certain embodiments, the diameter of the first open end is different to the diameter of the second open end. In various embodiments, the diameter of the first open end can be less than or greater than the diameter of the second open end. In various implementations, the first open end is in fluid communication with the gas reservoir or the second open end is in fluid communication with the atomizer emitter.

In certain embodiments, the apparatus includes a sample reservoir. In a non-limiting example, the sample reservoir is in fluid communication with the atomizer. In various embodiments, the sample reservoir is in fluid communication with the atomizer emitter. For example, the gas reservoir and the sample reservoir can both be in fluid communication with the atomizer emitter.

In some embodiments, the apparatus includes a sample valve located between the sample reservoir and the gas reservoir. In these and other embodiments, the apparatus can include a sample valve located between the sample reservoir and the gas guide. In certain embodiments, the sample valve can be adapted to adjust the sample flow from the sample reservoir. In some examples, the sample valve can be adapted to allow continuous or semi-continuous sample flow. In various implementations, the sample valve can be adapted to allow semi-continuous sample flow of a defined amount. For example, the sample valve may be adapted to allow semi-continuous sample flow of 0.5-100 µL or 10 µL. In one non-limiting example, the sample valve is adapted to allow semi-continuous sample flow of 1 µL to an area of 0.065-0.085 cm$^2$.

In various embodiments, the atomizer and the support are spaced apart. The support can include a solid support. In some embodiments, the support can include a plate including sample wells. For example, the support can include a plate including sample wells selected from 1, 6, 9, 12, 24, 48, 384, and 1536 wells. In certain embodiments, the solid support is formed from an inert material. For example, the solid support can be formed from a plastic material, or a metal or metal alloy, or a combination thereof. In some embodiments, the support includes a heating element and/or a resistive element. In certain embodiments, the support is reciprocally mountable to the apparatus. In various implementations, the support is reciprocally movable relative to the apparatus. For example, the support can be reciprocally movable relative to the atomizer. In various embodiments, the support can be reciprocally movable relative to the atomizer emitter. In some embodiments, the support includes a support actuator to reciprocally move the support relative to the atomizer. In various embodiments, the support includes a support actuator to reciprocally move the support relative to the atomizer emitter. In a non-limiting example, the support can include a support actuator to reciprocally move the support relative to the longitudinal axis of the atomizer emitter. In some embodiments, the support can include a support actuator to reciprocally move the support transverse to the longitudinal axis of the atomizer emitter.

In some embodiments, the longitudinal axis of the spray zone is coaxial with the longitudinal axis or center point of the support and/or the circular well of the support, to which the payload is to be delivered. In certain embodiments, the longitudinal axis of the atomizer emitter is coaxial with the longitudinal axis or center point of the support and/or the circular well of the support. In various embodiments, the longitudinal axis of the atomizer emitter, the longitudinal axis of the support, and the longitudinal axis of the spray zone are each coaxial. In certain embodiments, the longitudinal length of the spray zone is greater than the diameter (may be greater than double) of the circular base of the spray zone (e.g., the area of cells to which the payload is to be delivered).

In various embodiments, the apparatus includes a valve located between the gas reservoir and the atomizer. In some embodiments, the valve is an electromagnetically operated valve. In certain embodiments, the valve is a solenoid valve or a pneumatic valve. In some embodiments, the valve is located at the gas guide. For example, the valve can be adapted to adjust the gas flow within the gas guide. In various embodiments, the valve is adapted to allow continuous or semi-continuous gas flow. In a non-limiting example, the valve is adapted to allow semi-continuous gas flow of a defined time interval, such as a one second time interval. In certain embodiments, the apparatus includes at least one filter. In some embodiments, the filter includes a pore size of less than 10 µm or a pore size of 10 µm. In various embodiments, the filter is located at the gas guide. In some embodiments, the filter is in fluid communication with the gas guide.

In certain embodiments, the apparatus includes at least one regulator. The regulator can be, e.g., an electrical regulator or a mechanical regulator. In some embodiments, the regulator is located at the gas guide. In some embodiments, the regulator is in fluid communication with the gas guide. In various embodiments, the regulator is a regulating valve. In some embodiments, the pressure within the gas guide is about 1.0-2.0 bar or about 1.5 bar. In a non-limiting example, the pressure within the gas guide is 1.0-2.0 bar, and the distance between the atomizer and the support is less than or equal to 31 mm. For example, the pressure within the gas guide can be 1.5 bar, and the distance between the atomizer and the support can be 31 mm. In various implementations, the pressure within the gas guide is about 0.05 bar per millimeter distance between the atomizer and the support. In some embodiments, the regulating valve can be adapted to adjust the pressure within the gas guide to about 1.0-2.0 bar or to about 1.5 bar. In certain embodiments, each regulating valve can be adapted to maintain the pressure within the gas guide at about 1.0-2.0 bar or about 1.5 bar.

In some embodiments, the apparatus includes two regulators. For example, the apparatus can include first and second regulators. In various implementations, the first and second regulator can be located at the gas guide. In some implementations, the first and second regulator can be in fluid communication with the gas guide. In certain embodiments, the first regulator is located between the gas reservoir and the filter. In various embodiments, the first regulator can be adapted to adjust the pressure from the gas reservoir within the gas guide to about 2.0 bar or to maintain the pressure within the gas guide at about 2.0 bar. In some embodiments, the second regulator can be located between the filter and the valve.

In various embodiments, the atomizer emitter can be adapted to provide a conical spray zone (e.g., a generally circular conical spray zone). For example, the atomizer emitter can be adapted to provide a 30° conical spray zone. In some embodiments, the apparatus further can include a microprocessor to control any or all parts of the apparatus. In various embodiments, the microprocessor can be arranged to control any or all of the sample valve, the support actuator, the valve, and the regulator. In some implementations, the apparatus can include an atomizer having at least one atomizer emitter; and a support oriented relative to the atomizer; the atomizer can be selected from a mechanical atomizer, an ultrasonic atomizer, an electrospray, a nebuliser, and a Venturi tube. In certain embodiments, the atomizer can be adapted to provide a colloid suspension of particles having a diameter of 30-100 µm. In a non-limiting example, the apparatus can include a sample reservoir and a gas guide, and a sample valve located between the sample reservoir and the gas guide. In some embodiments, the sample valve can be adapted to allow semi-continuous sample flow of 10-100 µL. In various implementations, the atomizer and the support can be spaced apart and define a generally conical spray zone there between; and the distance between the atomizer and the support can be approximately double the diameter of the circular base of the area of cells to which molecules are to be delivered; the distance between the atomizer and the support can be 31 mm and the diameter of the circular base of the area of cells to which molecules are to be delivered can be 15.5 mm. In certain embodiments, the apparatus can include a gas guide and the pressure within the gas guide is 1.0-2.0 bar. In some embodiments, the apparatus can include at least one filter having a pore size of less than 10 µm.

Non-limiting examples of variations include: an atomizer or atomizers held on a static frame over a moving plate positioner; an atomizer or atomizers held on an adjustable x-y-z-r axis (where r is a rotational excursion from 0-360 degrees); an atomizer or atomizers held on a static support over a moving plate positioner; an atomizer or atomizers held on an adjustable x-y axis; an atomizer or atomizers held on a static frame over a moving plate positioner; and an atomizer or atomizers held on an adjustable x axis.

In some implementations, one or more atomizers are positioned at the distal end of a catheter or wand with the purpose of addressing tissues or parts of tissues ex vivo or in vivo. For example, aspects of the present subject matter relate to the delivery of gene editing payload(s) to exposed tissues, e.g., the dermis or eye tissue of an animal, or internal tissues, e.g., tissues comprising a lumen such as lung tissues (airways), gastrointestinal tissues (esophagus, intestines), or cardiovascular tissues (arteries or veins) of a mammal, e.g., a human or a mammal other than a human.

In various embodiments, one or more atomizers is positioned at the distal end of a catheter or wand with the purpose of addressing portions or subsets of a well plate surface (e.g., a portion of a plate or specific wells of a multi-welled plate). In certain embodiments, one or more atomizers is positioned on a static support positioned over a continuously moving substrate. The substrate may be compatible with cell culture or comprises plates or wells in which cells are cultured.

In some embodiments, a device or apparatus of the present subject matter comprises a visible low power laser and lens(es) arrangement co-incident with the atomizer or atomizers to indicate where the spray is being or will be delivered. In various embodiments, the laser and lens(es) can be adapted to adopt the same dispersion pattern as the atomizer(s). In some embodiments, the dispersion pattern is a conical dispersion pattern.

Various implementations of the present subject matter include a liquid dispenser and pipette(s) capable of producing microliter, nanoliter or picoliter drops and positioning drops individually onto cells under microscopic control, visualization, manipulation, and/or tuning of droplet/particle size. For example, droplets/aqueous particles (e.g., containing one or more RNPs) with a nanoliter or picoliter range volume are administered to a single cell (alone or as a member of a monolayer or mat of contiguous cells) under microscopic guidance. Using this approach, the plasma membrane is not punctured with a needle as with microinjection. Rather the droplet(s)/particle(s) are dropped or applied onto a cell and gain entry to the cytoplasm without physical manipulation of the plasma membrane such as microinjection. In this manner, the droplet/particle is tailored in size (e.g., 500 nanometers to 100 microns in diameter) or volume (e.g., between $1.0 \times 10^{-7}$ and 10 microliters; between $1.0 \times 10^{-6}$ and 10 microliters; between $1.0 \times 10^{-5}$ and 1 microliters; between $1.0 \times 10^{4}$ and 1.0 microliters; between $1.0 \times 10^{-6}$ and $1.0 \times 10^{-3}$ microliters; between $6.0 \times 10^{-7}$ and $7.4 \times 10^{-4}$ microliters, between $4.9 \times 10^{-6}$ and $2.2 \times 10^{-3}$ microliters, between $9.3 \times 10^{-6}$ and $2.8 \times 10^{-5}$ microliters, about $1.9 \times 10^{-5}$ microliters, or between $6.0 \times 10^{-7}$ microliter $2.2 \times 10^{-3}$ microliters) for optimal uptake by a cell as a function of the size (diameter) or exposed surface area of the cell. In some examples, the droplet/particle is about 10 to about 100,000 nanometers in diameter. For example, the droplet/particle may be about 10, 50, 100, 200, 300, 400, 500, 1000, 10,000, or 100,000 nanometers in diameter. In some embodiments, a device or apparatus that may be used for microinjection is instead used to deliver a droplet/particle to the surface of a cell without microinjection puncture of the plasma membrane. In such embodiments, the needle does not puncture the cell but instead is used to bring the droplet/particle into the proximity of the cell and/or place the droplet/particle onto the cell. In certain embodiments involving a needle (whether or not in conjunction with a microinjection device or apparatus), the size of the needle and/or pressure through which a solution is pushed through the needle may be adjusted to modify droplet/particle size. In various embodiments, one or more droplets/particles may be delivered to a plurality of cells, such as cultured cells or cells of a living organism. For example, the droplet/particle may be delivered to a mucosal or ocular cell, or to a fertilized egg or zygote. In one non-limiting example, a droplet is delivered to a cell or a plurality of cells of a mouse, frog, or fish (such as a zebrafish) zygote. In such examples, the zygote may be briefly removed from an aqueous solution, receive the droplet/particle, and then returned to an aqueous solution.

Aspects of the present invention relate to the expression vector-free delivery of gene editing compounds and complexes to cells and tissues, such as delivery of Cas-gRNA ribonucleoproteins for genome editing in primary human T cells and hematopoietic stem cells (HSC).

Various aspects of the CRISPR-Cas system are known in the art. Non-limiting aspects of this system are described, e.g., in U.S. Pat. No. 9,023,649, issued May 5, 2015; U.S. Pat. No. 9,074,199, issued Jul. 7, 2015; U.S. Pat. No. 8,697,359, issued Apr. 15, 2014; U.S. Pat. No. 8,932,814, issued Jan. 13, 2015; PCT International Patent Application Publication No. WO 2015/071474, published Aug. 27, 2015; Cho et al., (2013) Nature Biotechnology Vol 31 No 3 pp 230-232 (including supplementary information); and Jinek et al., (2012) Science Vol 337 No 6096 pp 816-821, the entire contents of each of which are incorporated herein by reference.

Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2 (SEQ ID NO: 1) and in the NCBI database as under accession number Q99ZW2.1. UniProt database accession numbers A0A0G4DEU5 and CDJ55032 provide another example of a Cas9 protein amino acid sequence (SEQ ID NO: 18). Another non-limiting example is a *Streptococcus thermophilus* Cas9 protein, the amino acid sequence of which may be found in the UniProt database under accession number Q03JI6.1 (SEQ ID NO:19). In some embodiments, the unmodified CRISPR enzyme has DNA cleavage activity, such as Cas9. In certain embodiments the CRISPR enzyme is Cas9, and may be Cas9 from *S. pyogenes* or *S. pneumoniae*. In various embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A, where the amino acid numbering is as shown in SEQ ID NO: 1) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A (where the amino acid numbering is as shown in SEQ ID NO: 1). In aspects of the invention, nickases may be used for genome editing via homologous recombination.

In certain embodiments, a Cas9 nickase may be used in combination with guide sequence(s), e.g., two guide sequences, which target respectively sense and antisense strands of the DNA target. This combination allows both strands to be nicked and used to induce NHEJ.

As a further example, two or more catalytic domains of Cas9 (RuvC I, RuvC II, and RuvC III) may be mutated to produce a mutated Cas9 substantially lacking all DNA cleavage activity. A D10A mutation may be combined with one or more of H840A, N854A, or N863A mutations to produce a Cas9 enzyme substantially lacking all DNA cleavage activity. In certain embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Other mutations may be useful; where the Cas9 or other CRISPR enzyme is from a species other than *S. pyogenes*, mutations in corresponding amino acids may be made to achieve similar effects.

In certain embodiments, a protein being delivered (such as a Cas protein or a variant thereof) may include a subcellular localization signal. For example, the Cas protein within a RNP may comprise a subcellular localization signal. Depending on context, a fusion protein comprising, e.g., Cas9 and a nuclear localization signal may be referred to as "Cas9" herein without specifying the inclusion of the nuclear localization signal. In some embodiments, the payload (such as an RNP) comprises a fusion-protein that comprises a localization signal. For example, the fusion-protein may contain a nuclear localization signal, a nucleolar localization signal, or a mitochondrial targeting signal. Such signals are known in the art, and non-limiting examples are described in Kalderon et al., (1984) *Cell* 39 (3 Pt 2): 499-509; Makkerh et al., (1996) *Curr Biol.* 6 (8):1025-7; Dingwall et al., (1991) *Trends in Biochemical Sciences* 16 (12): 478-81; Scott et al., (2011) *BMC Bioinformatics* 12:317 (7 pages); Omura T (1998) *J Biochem.* 123(6):1010-6; Rapaport D (2003) *EMBO Rep.* 4(10):948-52; and Brocard & Hartig (2006) *Biochimica et Biophysica Acta (BBA)—Molecular Cell Research* 1763(12):1565-1573, the contents of each of which are hereby incorporated herein by reference. In various embodiments, the Cas protein may comprise more than one localization signals, such as 2, 3, 4, 5, or more nuclear localization signals. In some embodiments, the localization signal is at the N-terminal end of the Cas protein and in other embodiments the localization signal is at the C-terminal end of the Cas protein.

Non-limiting examples of nuclear localization signals include GGSGPPKKKRKV (SEQ ID NO: 2), PKKKRKV (SEQ ID NO: 5), KR[PAATKKAGQA]KKKK (SEQ ID NO: 6), KR[XXXXXXXXXX]KKKK (SEQ ID NO: 7), KKXK (SEQ ID NO: 8), KRXK (SEQ ID NO: 9), KKXR (SEQ ID NO: 10), KRXR (SEQ ID NO: 11), AVKRPAATK-KAGQAKKKKLD (SEQ ID NO: 12), MSRRR-KANPTKLSENAKKLAKEVEN (SEQ ID NO: 13), PAAKRVKLD (SEQ ID NO: 14), PPKKKRKV (SEQ ID NO: 15), and KLKIKRPVK (SEQ ID NO: 16). A non-limiting example of a mitochondrial localization signal includes (SEQ ID NO: 17)
MLSLRQSIRFFKPATRTLCSSRYLL.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis.

Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme corresponding to the most frequently used codon for a particular amino acid.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. In some embodiments, the degree of complementarity is 100%. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), Clustal W, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In certain embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions.

A guide sequence may be selected to target any target sequence. In some embodiments, the target sequence is a sequence within a genome of a cell. Exemplary target sequences include those that are unique in the target genome. For example, for the S. pyogenes Cas9, a unique target sequence in a genome may include a Cas9 target site of the form MMMMMMMMMNNNNNNNNNNNNXGG (SEQ ID NO: 20) where NNNNNNNNNNNNXGG (N is A, G, T, or C; and X can be anything) has a single occurrence in the genome. A unique target sequence in a genome may include an S. pyogenes Cas9 target site of the form MMMMMMMMMNNNNNNNNNNNNXGG where NNNNNNNNNNNNXGG (N is A, G, T, or C; and X can be anything) has a single occurrence in the genome. For the S. thermophilus CRISPR1 Cas9, a unique target sequence in a genome may include a Cas9 target site of the form MMMMMMMMMNNNNNNNNNNNNXXAGAAW (SEQ ID NO: 21) where NNNNNNNNNNNNXXAGAAW (N is A, G, T, or C; X can be anything; and W is A or T) has a single occurrence in the genome. A unique target sequence in a genome may include an S. thermophilus CRISPR1 Cas9 target site of the form MMMMMMMMMNNNNNNNNNNNNXXAGAAW where NNNNNNNNNNNNXXAGAAW (N is A, G, T, or C; X can be anything; and W is A or T) has a single occurrence in the genome. For the S. pyogenes Cas9, a unique target sequence in a genome may include a Cas9 target site of the form MMMMMMMMMNNNNNNNNNNNNXGGXG (SEQ ID NO: 22) where NNNNNNNNNNNNXGGXG (N is A, G, T, or C; and X can be anything) has a single occurrence in the genome. A unique target sequence in a genome may include an S. pyogenes Cas9 target site of the form MMMMMMMMMNNNNNNNNNNNNXGGXG where NNNNNNNNNNNNXGGXG (N is A, G, T, or C; and X can be anything) has a single occurrence in the genome. In each of these sequences "M" may be A, G, T, or C, and need not be considered in identifying a sequence as unique. In some embodiments, a guide sequence is selected to reduce the degree of secondary structure within the guide sequence. Secondary structure may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, Nucleic Acids Research 36: W70-W74; and PA Carr and GM Church, 2009, Nature Biotechnology 27(12): 1151-62).

CRISPR-Cas technology which facilitates genome engineering in a wide range of cell types is evolving rapidly. It has recently been shown that delivery of the Cas9-gRNA editing tools in the form of ribonucleoproteins (RNPs) yields several benefits compared with delivery of plasmids encoding for Cas9 and gRNAs. Benefits include faster and more efficient editing, fewer off-target effects, and less toxicity. RNPs have been delivered by lipofection and electroporation but limitations that remain with these delivery methods, particularly for certain clinically relevant cell types, include toxicity and low efficiency. Accordingly, there is a need to provide a vector-free e.g., viral vector-free, approach for delivering biologically relevant payloads, e.g., RNPs, across a plasma membrane and into cells. "Cargo" or "payload" are terms used to describe a compound, or composition that is delivered via an aqueous solution across a cell plasma membrane and into the interior of a cell.

The current subject matter relates to delivery technology that facilitates delivery of a broad range of payloads to cells with low toxicity. Genome editing may be achieved by delivering RNPs to cells using some aspects of the current subject matter. Cas9 and two Alexa488-labelled gRNAs may be delivered individually to cells such as cells of the A549 human lung cell line. Cas9 may be detected by Western blotting in cells at 1 hour post-delivery. Levels decline thereafter until Cas9 is no longer detectable. The delivery technology per se does not deleteriously affect the viability or functionality of Jurkat and primary T cells. The current subject matter enables gene editing via Cas9 RNPs in clinically relevant cell types with minimal toxicity.

The transient and direct delivery of CRISPR/Cas components such as Cas and/or a gRNA has advantages compared to expression vector-mediated delivery. For example, an amount of Cas, gRNA, or RNP can be added with more precise timing and for a limited amount of time compared to the use of an expression vector. Components expressed from a vector may be produced in various quantities and for variable amounts of time, making it difficult to achieve consistent gene editing without off-target edits. Additionally, pre-formed complexes of Cas and gRNAs (RNPs) cannot be delivered with expression vectors.

In exemplary embodiments, the aqueous solution may further comprise an additive. Additional non-limiting additives, including those that were suboptimal such as glycerol may include glycerol (e.g., a concentration from 0.01 to 25% v/v in the aqueous solution), NDSB (e.g., a concentration of about 0.01 M to about 1 M in the aqueous solution), sorbitol (e.g., a concentration from 0.01 to 10% w/v in the aqueous solution) such as D-sorbitol, mannitol (e.g., a concentration from 0.01 to 10% w/v in the aqueous solution) such as D-mannitol, α-crystallin (e.g., a concentration from 1 to 500 μM in the aqueous solution; or from about 1 to 400 μM, or from about 1 to 300 μM, or from about 1 to 200 μM, or from about 1 to 100 μM, or from about 1 to 50 μM, or from about 1 to 20 μM, or from about 1 to 10 μM) such as α-crystallin purified from bovine eye lens, gelatin (e.g., a concentration from 0.01 to 10% w/v in the aqueous solution) such as gelatin A or gelatin B, glycine (e.g., a concentration of about 0.01 M to about 1 M in the aqueous solution), proline (e.g., a concentration of about 1 mM to about 200 mM in the aqueous solution), Tween-20 (e.g., a concentration of about 0.01% to about 5% v/v in the aqueous solution), L-histidine (e.g., a concentration of about 1 mM to about 200 mM in the aqueous solution), myo-inositol (e.g., a concentration from 0.01 to 10% w/v in the aqueous solution), and trehalose (e.g., a concentration of about 1 mM to about 200 mM in the aqueous solution).

In preferred embodiments, the additive may be α-crystallin. Accession numbers associated with the amino acid sequence of α-crystallin and examples for human α-crystallin include: CAA32891.1, ACP18852.1, AAB22011.1, AAB22010.1, AMM63587.1, EAX09498.1, EAW67163.1, AAI13599.1, AAP35416.1, AMM63591.1, and AAB22009.1 In some examples, the amino acid sequence of α-crystallin comprises Accession number CAA32891.1 (EMBLL X14789 mRNA. Translation: CAA32891.1), wherein the amino acid sequence is shown (SEQ ID NO: 23):

```
  1  mdvtiqhpwfkrtlgpfypsrlfdqffgeglfeydllpflsstispyyrqslfrtvldsg
 61  isevrsdrdkfvifldvkhfspedltvkvqddfveihgkhnerq
```

Exemplary regions or fragments include, but are not limited to, amino acids 1-50 and 60 to 104.

In some examples, the amino acid sequence of α-crystallin comprises Accession number ACP18852.1 (EMBL FJ876064 mRNA. Translation: ACP18852.1), wherein the amino acid sequence is shown (SEQ ID NO: 24):

```
  1  mdiaihhpwihrpffpfhspsrlfdqffgehllesdlfptstslspfylrppsflrapsw
 61  fdtglsemrlekdrfsvnldvkhfspeelkvkvlgdvievhgkheerqdehgfisrefhr
121  kyripadvdpltitsslssdgvltvngprkqvsgpertipitreekpavtaapkk
```

Exemplary regions or fragments include, but are not limited to, amino acids 1 to 51, 14 to 161, or 67-50.

In some embodiments, the commercially available α-crystallin may be of two isoforms, cry-aA or cry-aB. In some embodiments the ratio may be 1:1, 1:2, 1:3, 1:4, 1:5, or 2:1, 3:1, 4:1, or 5:1 of cry-aA to cry-aB. In the lens, alpha-crystallin is a polydisperse molecule consisting of a 3:1 ratio of alpha A to alpha B subunits. In some examples, the α-crystallin may be purified from bovine lens, for example, Bovine alpha crystalline (Sigma C4163).

The amino acid sequence of Alpha-crystallin A chain CRYAA (Bovine) is shown (SEQ ID NO: 25):

```
MDIAIQHPWFKRTLGPFYPSRLFDQFFGEGLFEYDLLPFLSSTISPYY
RQSLFRTVLDSGISEVRSDRDKFVIFLDVKHFSPEDLTVKVQEDFVEI
HGKHNERQDDHGYISREFHRRYRLPSNVDQSALSCSLSADGMLTFSGP
KIPSGVDAGHSERAIPVSREEKPSSAPSS
```

The amino acid sequence of Alpha-crystallin B chain CRYAB (Bovine) is shown (SEQ ID NO: 26):

```
MDIAIHHPWIRRPFFPFHSPSRLFDQFFGEHLLESDLFPASTSLSPFY
LRPPSFLRAPSWIDTGLSEMRLEKDRFSVNLDVKHFSPEELKVKVLGD
VIEVHGKHEERQDEHGFISREFHRKYRIPADVDPLAITSSLSSDGVLT
VNGPRKQASGPERTIPITREEKPAVTAAPKK
```

In some embodiments, human Alpha A or B crystallin may be purchased from any suitable vendor, including Cell Sciences. In some examples, the Alpha crystallin A (Item no. CRC167) may have the amino acid sequence (SEQ ID NO: 27)

```
MDVTIQHPWF KRTLGPFYPS RLFDQFFGEG LFEYDLLPFL
SSTISPYYRQ SLFRTVLDSG ISEVRSDRDK FVIFLDVKHF
SPEDLTVKVQ DDFVEIHGKH NERQDDHGYI SREFHRRYRL
PSNVDQSALS CSLSADGMLT FCGPKIQTGL DATHAERAIP
VSREEKPTSA PSS
```

In other examples, the Alpha crystallin B (Item no. CRC168) may have the amino acid sequence (SEQ ID NO: 28)

```
MDIAIHHPWI RRPFFPFHSP SRLFDQFFGE HLLESDLFPT
STSLSPFYLR PPSFLRAPSW FDTGLSEMRL EKDRFSVNLD
VKHFSPEELK VKVLGDVIEV HGKHEERQDE HGFISREFHR
KYRIPADVDP LTITSSLSSD GVLTVNGPRK QVSGPERTIP
ITREEKPAVT AAPKK
```

In some embodiments, human Alpha A or B crystallin may be purchased from any suitable vendor, including also, Abcam, wherein Alpha A (ab48778) has the amino acid sequence (SEQ ID NO: 29)

```
MDVTIQHPWF KRTLGPFYPS RLFDQFFGEG LFEYDLLPFL
SSTISPYYRQ SLFRTVLDSG ISEVRSDRDK FVIFLDVKHF
SPEDLTVKVQ DDFVEIHGKH NERQDDHGYI SREFHRRYRL
PSNVDQSALS CSLSADGMLT FCGPKIQTGL DATHAERAIP
VSREEKPTSA PSS
```

In other aspects, the Alpha crystallin B from Abcam (ab48779) has the amino acid sequence (SEQ ID NO: 30)

```
MDIAIHHPWIRRPFFPFHSP SRLFDQFFGE HLLESDLFPT
STSLSPFYLR PPSFLRAPSW FDTGLSEMRL EKDRFSVNLD
VKHFSPEELK VKVLGDVIEV HGKHEERQDE HGFISREFHR
KYRIPADVDP LTITSSLSSD GVLTVNGPRK QVSGPERTIP
ITREEKPAVT AAPKK
```

In some embodiments $MgCl_2$ may be in a concentration for less than about 2.5, 2, 0.5, 0.1, or 0.01 $MgCl_2$ and/or less than about 5, 4, 3, 2, 1, 0.5, 0.1, 0.01% w/v glycerol.

A further advantage of the compositions and methods described herein includes a minimization or reduction of precipitation of gene editing protein cargo, e.g., Cas9. Cas9, a bacterial protein, has been observed to precipitate out of solution under certain conditions, which precipitation may reduce its function or activity. To reduce, minimize, or eliminate Cas9 precipitation, the delivery buffer compositions optionally include excipients or additives that protect the protein from precipitation. Such protectants include a heat shock protein, e.g., α-crystallin. Other heat shock protein protectants include Hsp60, Hsp72 and Hsp73 (Whitley et al., 1999, J. of Vascular Surgery 29(4):748-751).

Other excipients or additives include a sugar alcohol, e.g., sorbitol. The addition of α-crystallin and/or sorbitol improved the nuclease activity of Cas-9:gRNA after exposure to an alcohol, e.g, ethanol-based delivery solution, thereby overcoming the problems and drawbacks of Cas9 precipitation/reduction of activity in certain buffers.

Thus, the invention includes a composition, e.g, buffer solution, for delivering a gene editing protein or gene editing complex to a cell, which contains at least 2% (but less than 70%) alcohol, e.g., ethanol, and which optionally contain a heat shock protein such as α-crystallin and/or a sugar alcohol such as sorbitol. A method for editing a target gene in a cell comprises contacting the cell (in which gene editing is desired) with a spray of mist of droplet comprising a gene editing protein or complex, incubating the cells for a time, e.g., about 0-10 minutes, 0.1-10 minutes, 1-5 minutes, e.g., about 2 minutes, to destabilize the plasma membrane of the cell thereby allowing entry of the cargo across the plasma membrane and into the cell, contacting the same cells with a stop solution for a time, e.g., 0-5 minutes, 0.1-5 minutes, 0.2-4 minutes, 0.3-3 minutes, 0.4-2 minutes, 0.5-1 minute, e.g., 30 seconds, to reverse the cell membrane permeabilization/destabilization process, and incubating the cells in cell culture media, e.g., a standard cell culture media, during which gene editing occurs, e.g., the cells may be remain in this solution for the duration of culture. As was discussed above, a significant advantage of the described methods is that this series of steps may optionally be repeated several (2, 3, 4, 5, 6, 8, 10, or more) times to increase the amount of cargo delivered into the cell and/or the efficiency of gene editing. Optionally, a recovery period between doses (e.g., the next delivery spray) ranges from 1-8 hours, e.g., 2-6 hours, e.g., about 4 hours, between cargo delivery spray delivery events.

The methods and compositions described herein are advantageous over other delivery methods, because the duration from treatment of cells to viable, gene-edited cells suitable for clinical use is shorter. The speed of delivery of cargo using the ethanol spray delivery system described here is comparable to electroporation; however, cell recovery is faster than electroporation. For T cells, proliferation is not delayed by the methods of the invention but is delayed for 2 days by electroporation. For MSC, cell differentiation is equivalent to untreated controls with the technology of the invention but is delayed by electroporation. In terms of viability and functionality, the cells are ready for use 4 hours after treatment using the spray technology described here.

Thus, the speed of processing cells for subsequent use, e.g., delivery to a human or animal subject for clinical treatment, is an advantage over procedures that require lengthy time periods for the treated cells to resume normal health/function. For example, delivery by electroporation compromises the function of some cells such as MSCs and T cells. This drawback of electroporation is likely due to large electrical gradients (especially in small cells) and local heating, which trigger DNA damage and endogenous repair mechanisms (Meaking et al., 1995, Biochimica et Biophysics Acta 1264:357-362 and Branzei et al., 2008, Nature Reviews Molecular Cell Biology 9:297-308). For example, the functional integrity of some cells become compromised, e.g., reduced differentiation, reduced activity, after electroporation, e.g., reduced functional integrity for up to weeks after electroporation. In contrast, the viability and functionality of cells treated using the methods and compositions is minimally or not compromised, and the cells are ready for use within hours (1, 2, 6, 12, 18, 24 hours after treatment) or days (1, 2, 3, 4, 5, 6, 7 days after treatment). Thus, an overall key advantage of the gene editing technology described herein is avoidance of the membrane disruption by electrical gradients. Moreover, electroporation parameters may vary widely depending on the cell type and experimental condition. In contrast, the methods and systems of the invention data work well on a wide range of cell types, the method can be completed in minutes, and is carried out under cell-friendly conditions. The viability and functionality of cells treated using the spray delivery methods and compositions described here are minimally or not compromised, and the cells are ready for use within hours (1, 2, 6, 12, 18, 24 hours after treatment) or days (1, 2, 3, 4, 5, 6, 7 days after treatment).

Each embodiment disclosed herein is contemplated as being applicable to each of the other disclosed embodiments. In some aspects, the aqueous solution does not comprise $MgCl_2$ and/or glycerol. Thus, all combinations of the various elements described herein are within the scope of the invention.

The details of one or more variations of the subject matter described herein are set forth in the accompanying drawings and the description below. Other features and advantages of the subject matter described herein will be apparent from the description and drawings, and from the claims. All references cited herein including the contents of accession number citations for protein or nucleic acid sequences are incorporated by reference.

DESCRIPTION OF THE DRAWINGS

FIG. 6 is graphical representation of the methods described herein, wherein the delivery mechanism described.

FIG. 8 is a set of images validating effectiveness of the delivery solution containing 15% EtOH and 2.5 mM $MgCl_2$. Successful delivery of reporter protein ovalbumin-FITC (OVA-FITC) to A549 cells was observed when delivery solution was modified to contain 15% ethanol and 2.5 mM $MgCl_2$. Delivery appeared enhanced in the presence of 2.5 mM $MgCl_2$.

FIGS. 10A and B are western blots illustrating a Cas9 protein-dose delivery response. Increasing levels of Cas9 were detected in (FIG. 10A) A549 cells and (FIG. 10B) Jurkat cells when increasing doses of Cas9 protein were delivered.

(FIG. 11A) Cas9-Cy3 protein (red) was delivered to cells and analyzed 1 hr post-delivery by fluorescence microscopy. DAPI nuclear counterstain (blue) shows nuclei. Addition of $MgCl_2$ to the delivery solution (+$MgCl_2$) resulted in increased delivery efficiency of Cas9. (FIG. 11B) Cas9 protein was delivered and cells were fixed with methanol 1 hr post-delivery. Cas9 expression was visualized by immunofluorescence using an anti-Cas9 antibody (green). DAPI nuclear counterstain (blue) shows nuclei. (FIG. 11C) Dual-RNA1-FAM (green) was delivered to cells and analyzed 1 hr post-delivery by fluorescence microscopy. DAPI nuclear counterstain (blue) shows nuclei. Addition of $MgCl_2$ to the delivery solution (+$MgCl_2$) resulted in increased delivery efficiency of Dual-RNA1-FAM. (FIG. 11D) RNP comprising Cas9: Dual-RNA1-FAM (green) was delivered to cells and analyzed 1 hr post-delivery by fluorescence microscopy. DAPI nuclear counterstain (blue) shows nuclei. (FIG. 11E) RNP comprising Cas9: Dual-RNA1-FAM was delivered and cells were fixed with methanol 1 hr post-delivery. RNP expression was visualized by immunofluorescence using an anti-Cas9 antibody (red). DAPI nuclear counterstain (blue) shows nuclei.

FIG. 13 is a set of graphs comparing viability and efficiency with Neon electroporator and the Delivery Platform.

FIGS. 14A and B are a set of graphs showing the effect of Delivery Platform technology on the activation of Jurkat cells. Delivery solution without payload (SBO) was delivered to Jurkat cells. Control cells were untreated (UT). Expression of CD69 (FIG. 14A) and CD25 (FIG. 14B) was analyzed at 4 hr or 24 hr respectively post-stimulation with PHA.

FIG. 15 is the amino acid sequence of an exemplary Cas9 protein (SEQ ID NO: 4), which includes, from the N-terminus to the C-terminus, a *Streptococcus pyogenese* protein (SEQ ID NO: 1) followed by a nuclear localization signal (SEQ ID NO: 2) followed by an Human influenza hemagglutinin (HA) epitope tag (SEQ ID NO: 3). The nuclear localization signal and the HA epitope tag are underlined.

FIG. 16 is set of Western blots showing delivery of Cas9 protein to PBMC and Beas-2B cells. Cas9 protein was delivered to PBMC and Beas-2B cells and detected by Western blotting of cell lysates.

μl Ethanol, MGW to 10 μl), 2 μl on a glass slide for microscopy observed under a light microscope. The clusters visible in the picture (arrow) represent aggregates of Cas9 protein falling out of solution immediately after the addition of 25% Ethanol.

Figure 22:
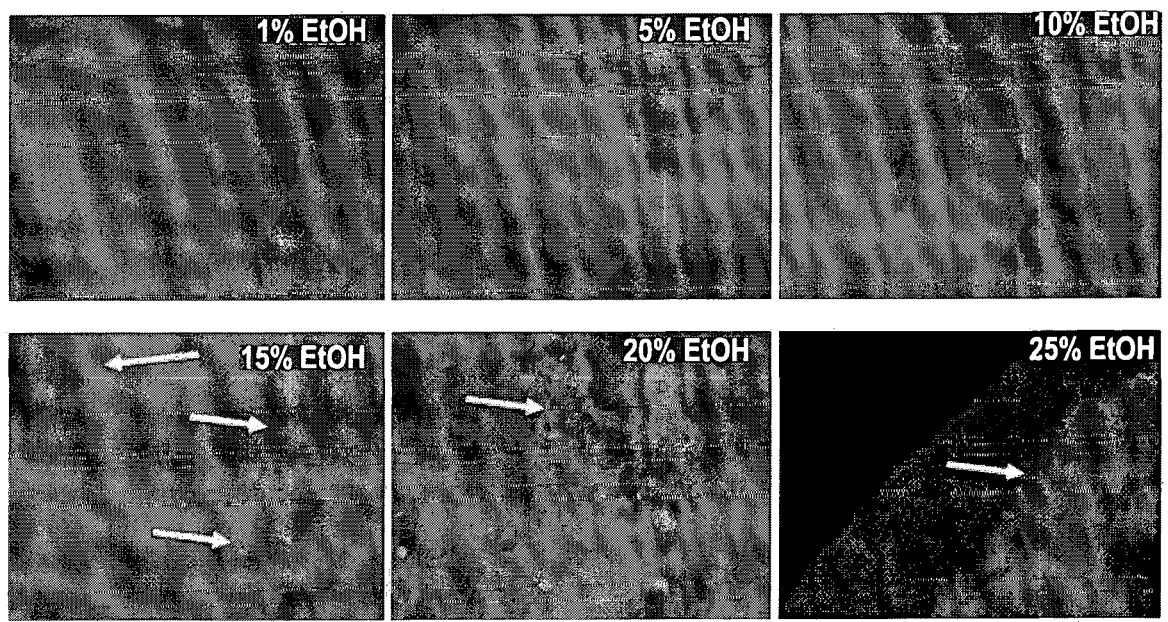

FIG. 22 are images depicting the effects of ethanol concentration in delivery solution on precipitation of Cas9. Labelled Cas9 93 ng/μl in delivery solution (25% S-buffer, 25% Ethanol, water to 10 μl) with 10× magnification are depicted in the top three images, and 20× magnification is depicted in the bottom three images. 2 μl sample on glass slides were observed under a fluorescence microscope. For 1%, 5% and 10% no aggregation and precipitation was observed. At 15% Ethanol small aggregates formed and precipitated (arrows), for 20 and 25% Ethanol big clusters of protein formed and separated from solution (arrows). Images were recorded 10 s after Ethanol addition to the solution containing Cas9 and all components of the delivery solution except Ethanol.

FIG. 23 are images depicting the effects of ethanol concentration in delivery solution on precipitation of Cas9. Labelled Cas9 93 ng/μl in delivery solution (25% S-buffer, 25% Ethanol, water up to 10 μl) at 20× magnification is depicted. 12% Ethanol was the lowest concentration that triggered protein precipitation.

FIG. 24 are images depicting Cas9 with no ethanol and protein eluted from the column. Cas9 as eluted and in S-buffer (40× magnification) was depicted to show the absence of significant aggregation or precipitation before Ethanol addition and to show that S-buffer was not a detrimental effect on the protein solubility.

Figure 25:
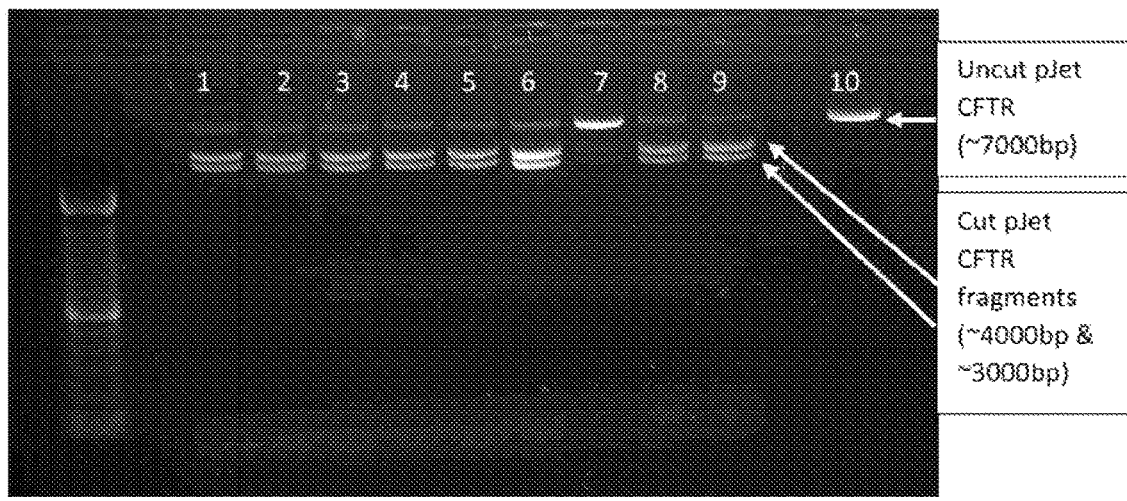

FIG. 25 is an image of an electrophoresis agarose gel illustrating Cas9 concentration for RNP complexes made up in delivery solution containing different amounts of ethanol. Samples correspond to those reported in Table 9. Sample 10 represents a negative control where the RNP tool was not present, hence the DNA target was intact. In all other samples edit was confirmed by the presence of the two front bands representing the two fragments of target DNA cut by the RNP tool. The agarose gel was a 1.5% gel run at 100V.

Figure 26A:
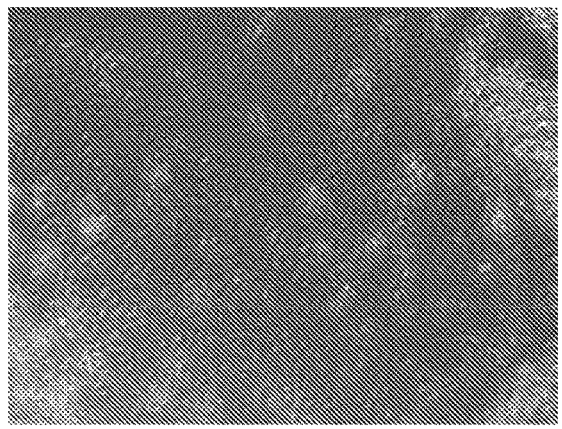
Figure 26B:
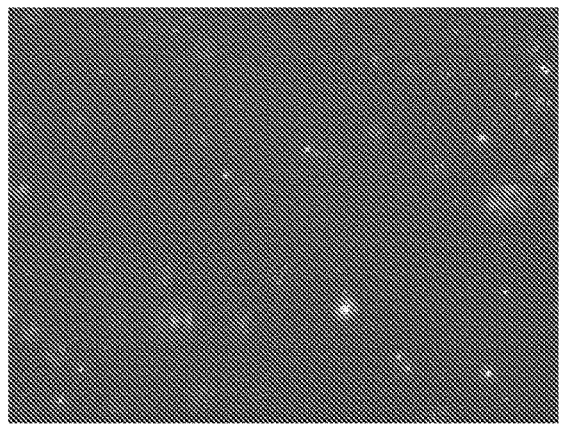
Figure 26C:
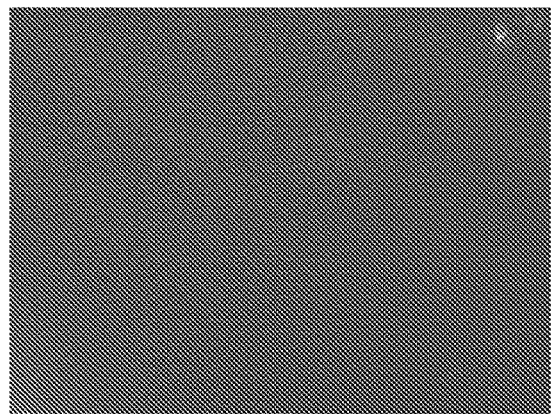

FIGS. 26A-26C are images depicting the effect of NDSB-201 on Cas9 precipitation. FIG. 26A is an image depicting unlabelled Cas9 500 ng/μl in delivery solution (0.5 μl Cas9 μg/μl, 2.5 μl S-buffer, 2.5 μl Ethanol, MGW to 10 μl), 2 μl on a glass slide for microscopy observed under a light microscope. The clusters visible in the picture represented aggregates of Cas9 protein falling out of solution immediately after the addition of 25% Ethanol; FIG. 26B is an image depicting RNP (3:1 gRNA/Cas9) in delivery solution containing 0.5 M NDSB, the precipitation phenomenon was significantly decreased; FIG. 26C is an image depicting RNP (3:1 gRNA/Cas9) in delivery solution containing 20% glycerol, no visible precipitation was observed.

Figure 27:
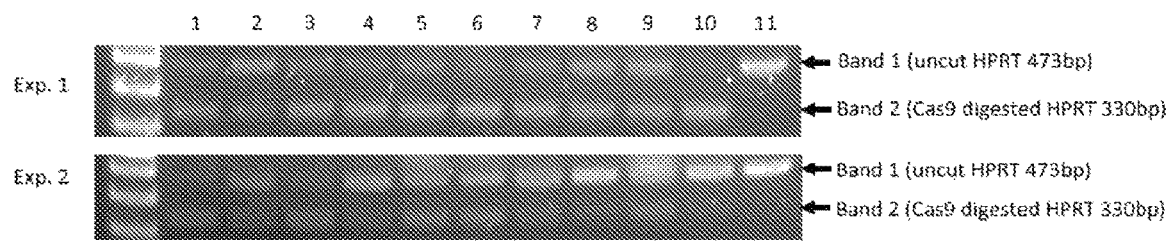

FIG. 27 is a gel depicting the editing efficiency of Cas9: gRNA on HPRT DNA (Editing efficiency=band 2/(band 1+band 2)). The editing efficiencies were normalized to the 0% Ethanol sample. Two replicates are shown for each condition. The samples were as follows, lane 1: 0% Ethanol, lane 2: 25% Ethanol, lane 3: sorbitol (4% w/v), lane 4: D-mannitol (2% w/v), lane 5: α-crystallin (100 μM), lane 6: α-crystallin (220 μM), lane 7: NDSB (0.2 M), lane 8: trehalose (26.4 mM) lane 9: trehalose (26.4 mM)/α-crystallin (100 μM), lane 10: TF-Ethanol (0.7%) used instead of Ethanol, lane 11: uncut HPRT DNA.

Figure 28:
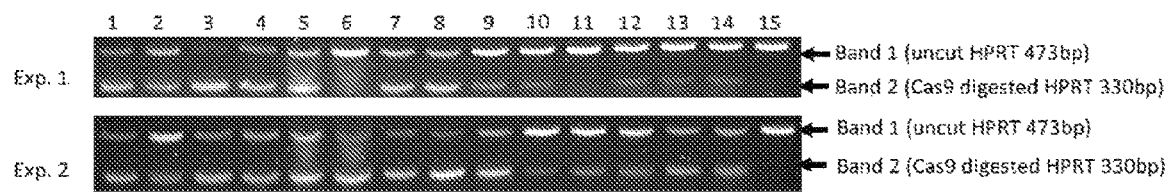

FIG. 28 is a gel depicting the editing efficiency of Cas9: gRNA on HPRT DNA (Editing efficiency=band 2/(band 1+band 2)). The editing efficiencies were normalized to the 0% Ethanol sample. Two replicates are shown for each condition. The samples were as follows, lane 1: 1: 0% Ethanol, lane 2: 25% Ethanol, lane 3: D-sorbitol (4% w/v) (in S. buffer), lane 4: D-sorbitol, lane 5: α-crystallin (220 μM), lane 6: α-crystallin (220 μM)/D-sorbitol (4% w/v) (in S. buffer), lane 7: gelatin A (1% w/v), lane 8: gelatin B (1% w/v), lane 9: glycine (0.25 M), lane 10: proline (75 mM), lane 11: L-arginine (50 mM), lane 12: histidine (12.8 mM), lane 13: myo-inositol (1% w/v), lane 14: tween-20 (0.1% v/v), lane 15: uncut HPRT DNA.

Figure 29A:
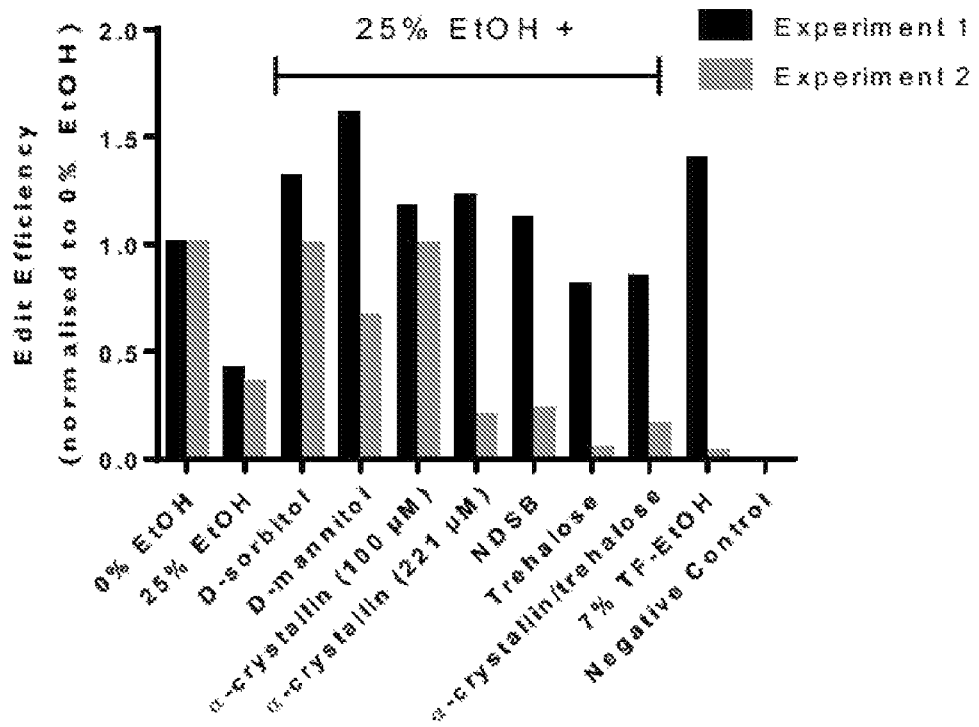
Figure 29B:
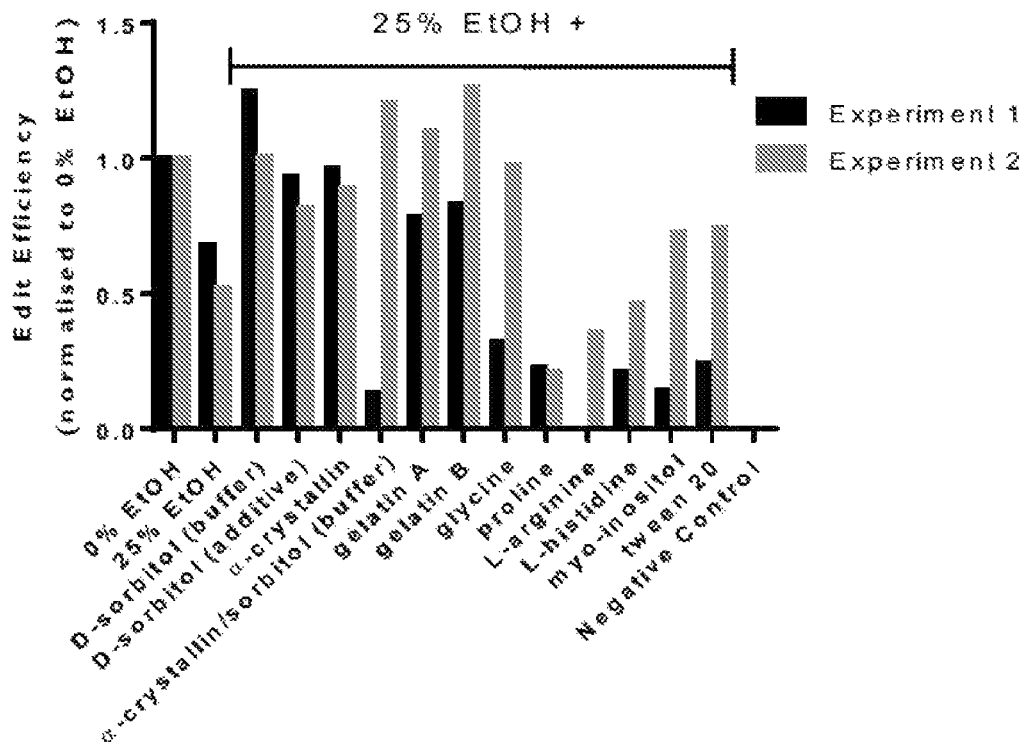

FIGS. 29A and 29B are bar graphs indicating the editing efficiency of Cas9: gRNA on HPRT DNA (Editing efficiency=band 2/(band 1+band 2)). The editing efficiencies were normalized to 0% Ethanol sample. Two replicates are shown for each condition. FIG. 29A depicts a bar graph indicating the effects of additives including 0% EtOH, 25% EtOH, D-sorbitol, D-mannitol, α-crystallin (100 μM), α-crystallin (221 μM), NDSB, trehalose, α-crystallin/trehalose, 7% TF-EtOH, and a negative control. FIG. 29B depicts a bar graph indicating the effects of additives including 0% EtOH, 25% EtOH, D-sorbitol (buffer), D-sorbitol (additive), α-crystallin, α-crystallin/sorbitol (buffer), gelatin A, gelatin B, glycine, proline, L-arginine, L-histidine, myo-inositol, tween-20, and a negative control.

Figure 30:
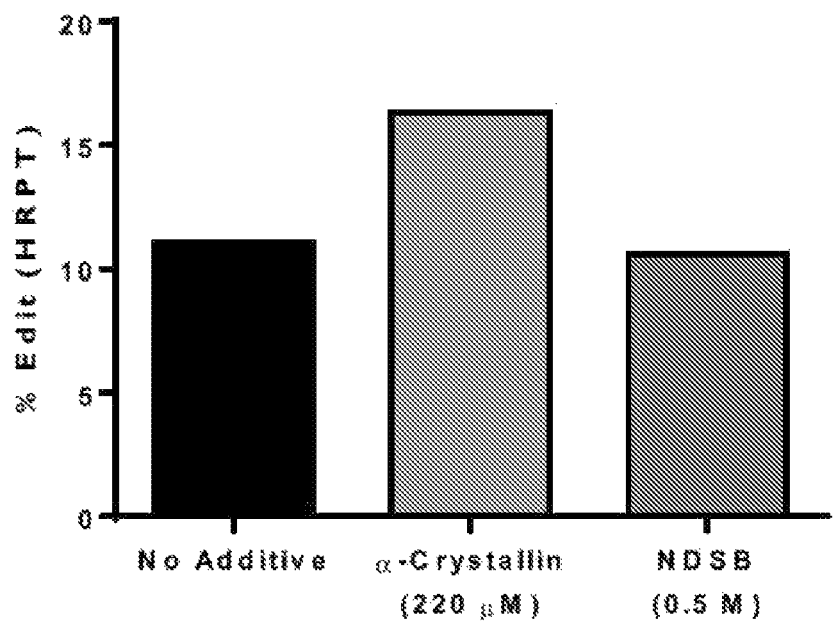

FIG. 30 is a bar graph depicting the percentage of CRISPR induced hprt edit of MSC cells with and without additives.

Figure 31:
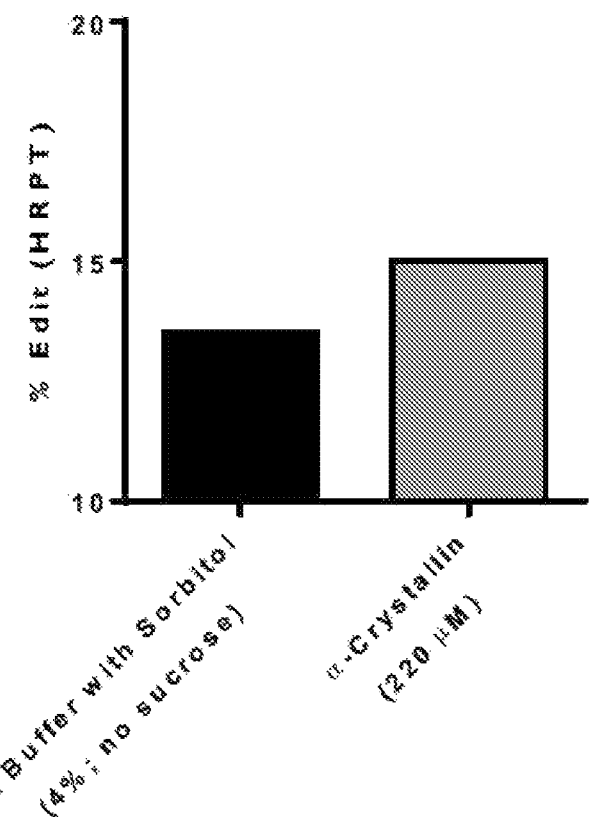

FIG. 31 is a bar graph illustrating the percentage of CRISPR induced hprt edit of U2OS cells with and without additives (2 hits).

Figure 32:
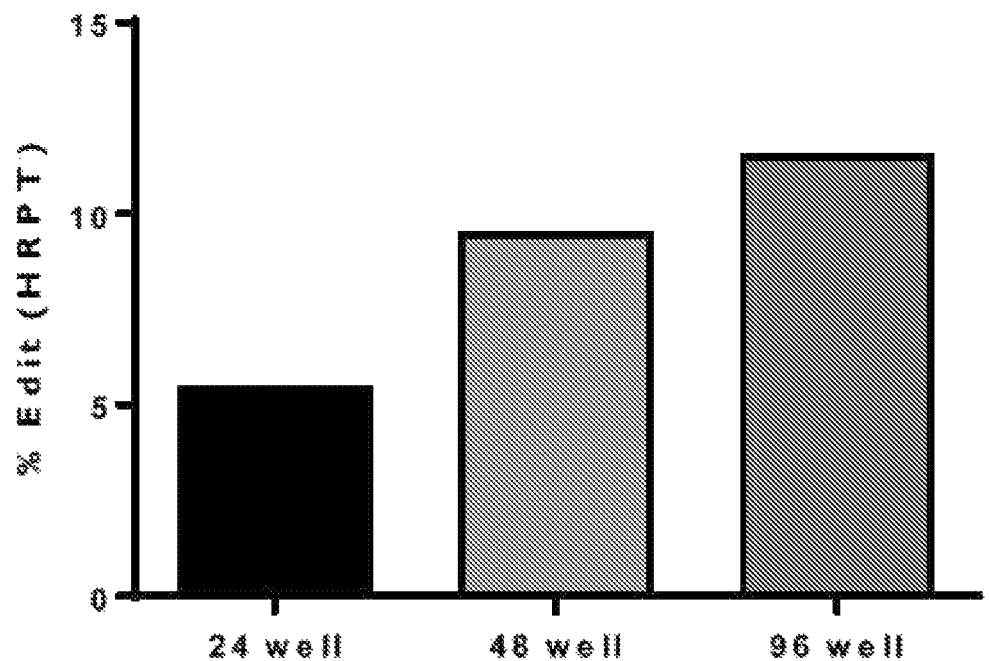

FIG. 32 is a bar graph illustrating the edit efficiency in smaller wells (24-well plate, 48-well plate, and a 96-well plate). The edit efficiency increased in cells seeded in smaller wells.

Figure 33:
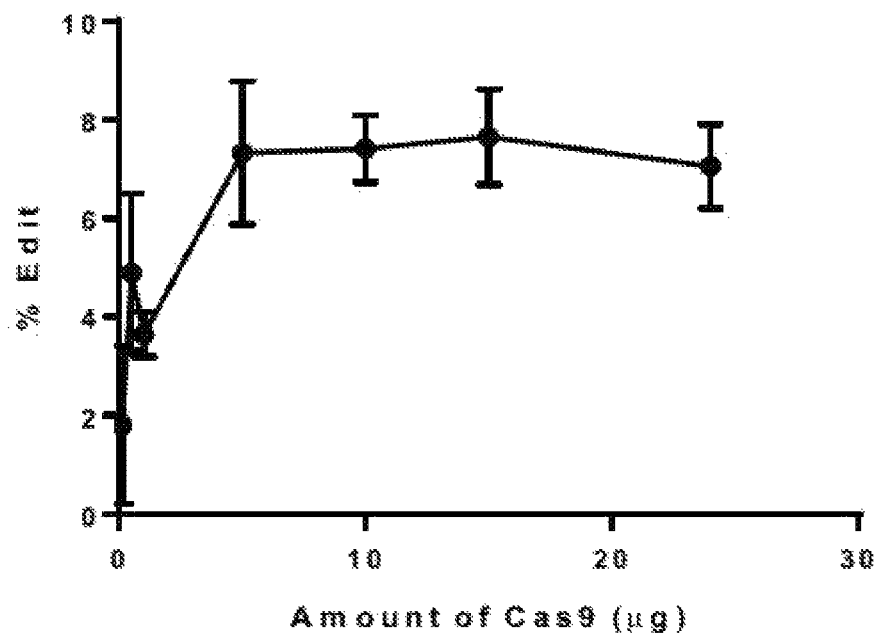

FIG. 33 is a graph depicting the effect of increasing Cas9 concentration on edit efficiency. Increasing the amount of Cas9 increased the percentage edit in MSCs.

Figure 34:
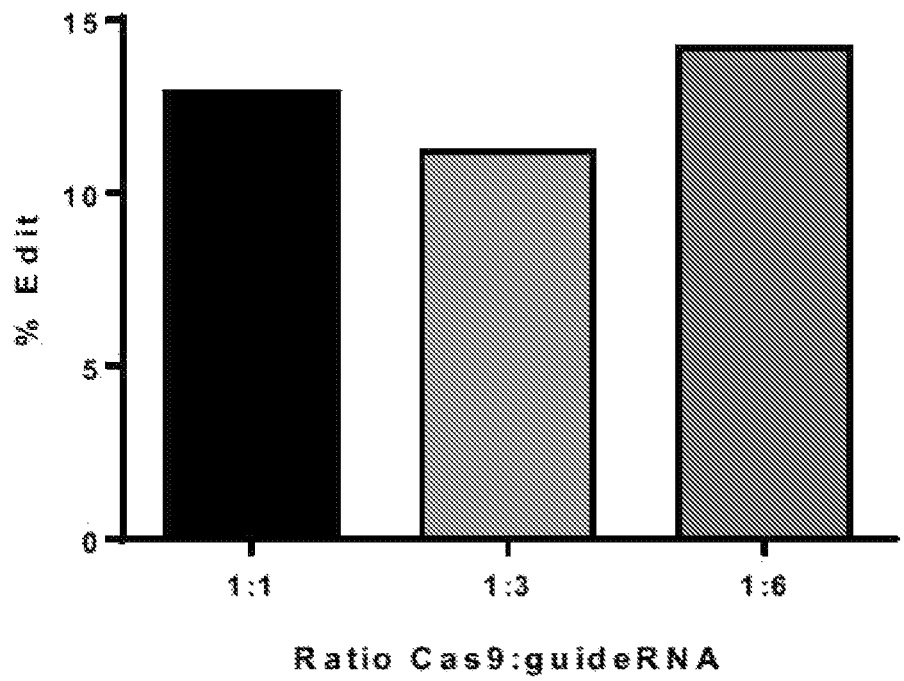

FIG. 34 is a bar graph depicting the effect of Cas9:gRNA ratio on edit efficiency. Altering the ratio of Cas9 to guide RNA did not affect edit efficiency.

Figure 35:
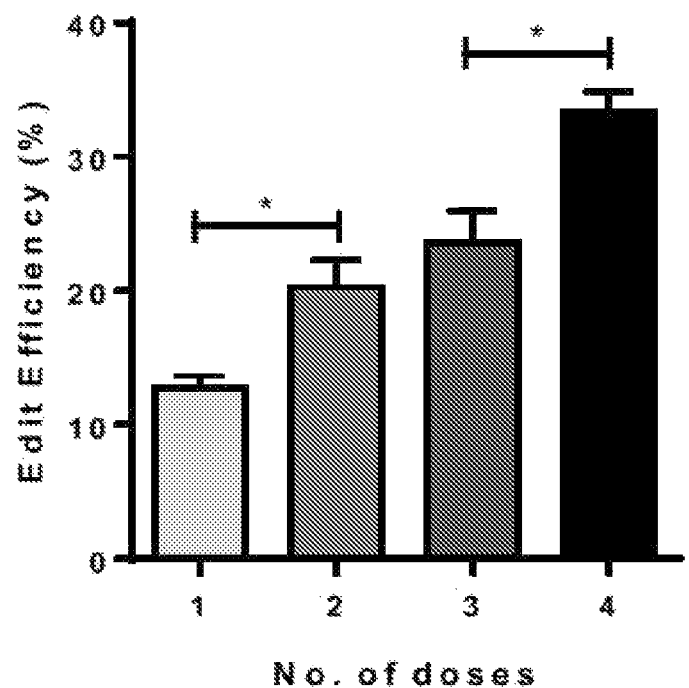

FIG. 35 is a bar graph depicting the effect of RNP doses delivered on edit efficiency. Increasing the number of doses increased the percentage edit in MSCs.

Figure 36:
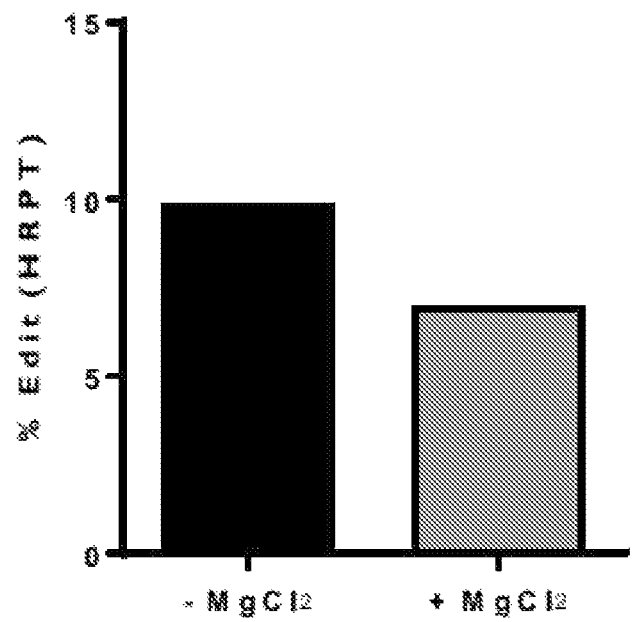

FIG. 36 is a bar graph depicting the effect of $MgCl_2$ on edit efficiency. Edit efficiency was not improved with $MgCl_2$ addition.

Figure 37:
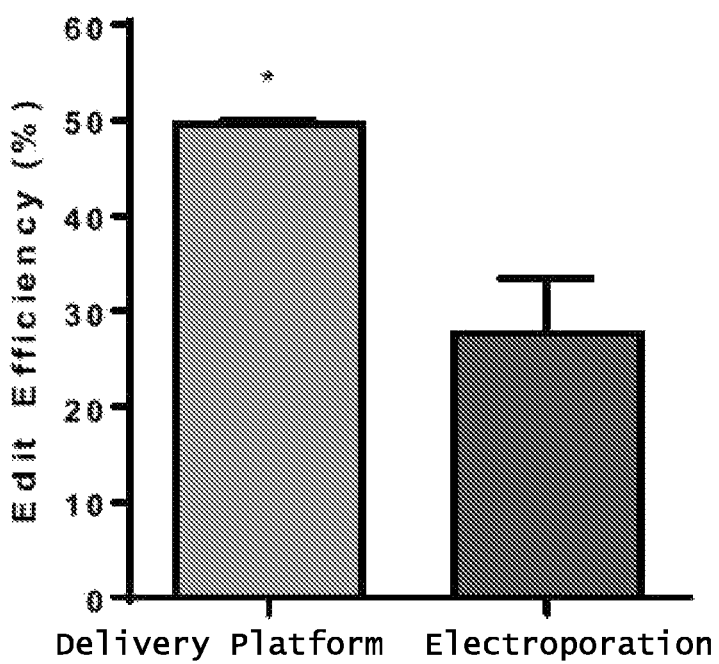

FIG. 37 is a bar graph depicting a comparison of edit efficiency between Delivery Platform technology and electroporation. Edit efficiency was greater in MSCs when Cas9 RNP was delivered by Delivery Platform technology as compared with electroporation.

Figure 38:
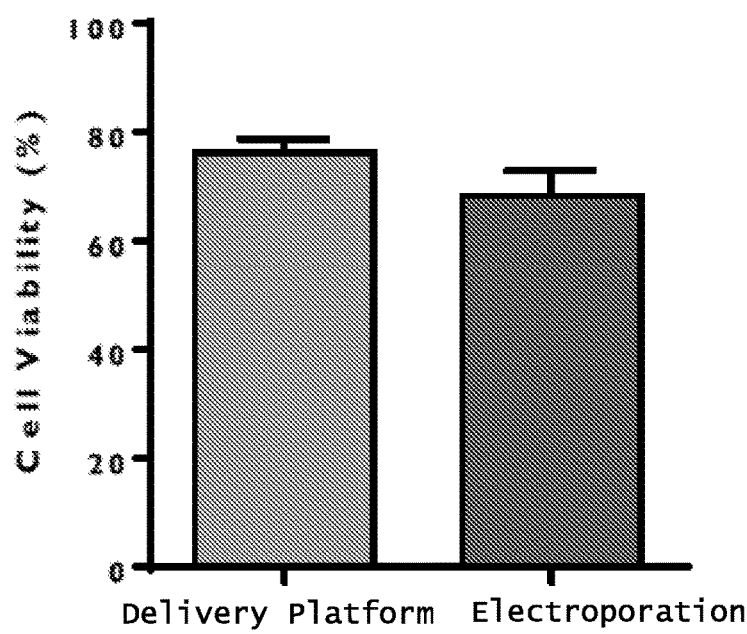

FIG. 38 is a bar graph depicting a comparison of cell viability following RNP delivery: Delivery Platform technology versus electroporation. Comparable viability was observed in cells treated by either Delivery Platform technology or electroporation.

Figure 39:
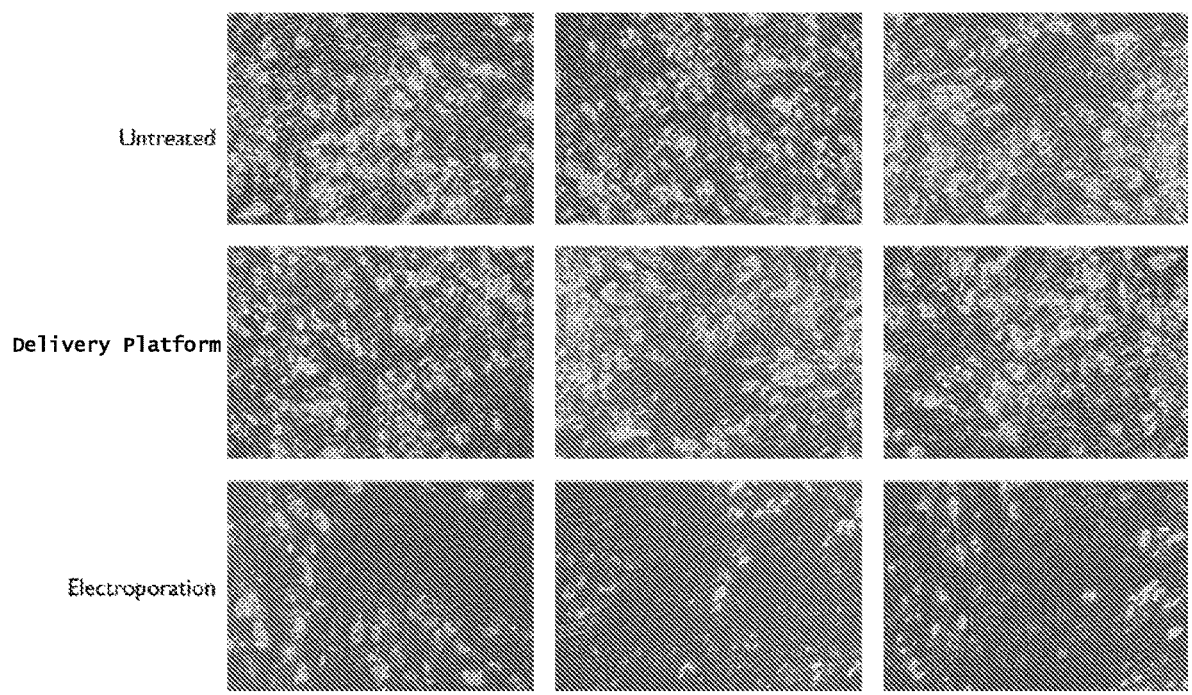

FIG. 39 are images depicting a comparison of cell functionality following RNP delivery: Delivery Platform technology versus electroporation. The functionality of MSCs was unaffected by Delivery Platform technology. Three representative images of differentiated MSC from an untreated group (Untreated), a Cas9 RNP delivered by Delivery Platform technology group (Delivery Platform), and a Cas9 RNP delivered by Electroporation group (Electroporation) are shown. There was no difference between untreated and Delivery Platform-treated cells. However, differentiation was inhibited in cells treated by electroporation.

Figure 40:
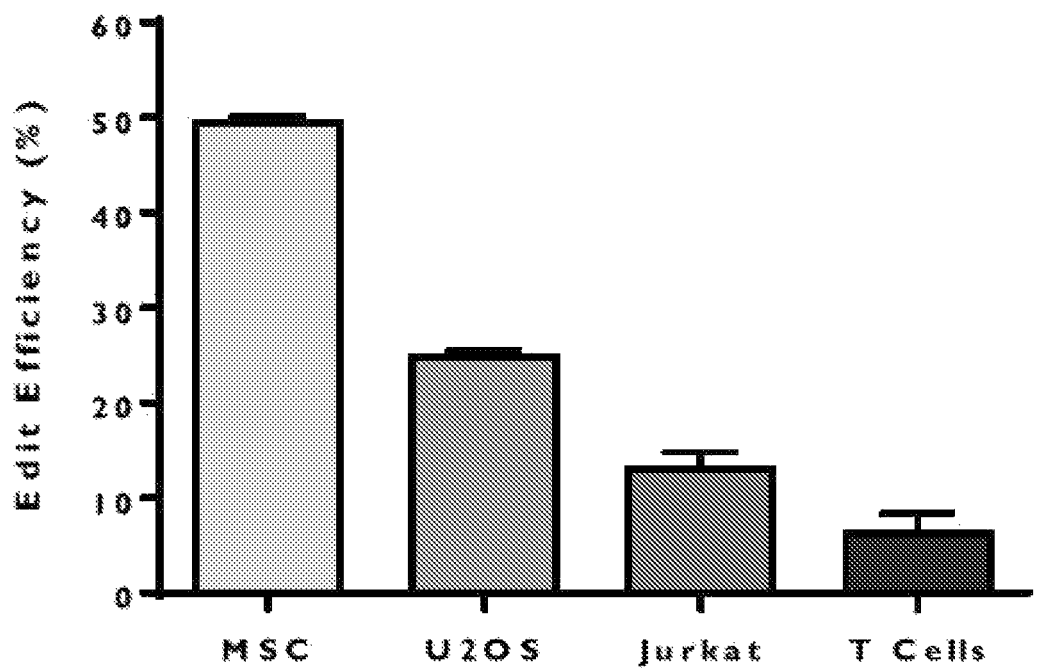

FIG. 40 is a bar graph depicting the edit efficiency in adherent and suspension cell lines, and primary cells. Edit efficiency data for adherent (MSC, U2OS) and suspension (T cell, Jurkat), cell lines (U2OS, Jurkat) and primary cells (MSC, T cell). Successful edit was observed in both cell lines and primary human cells.

Figure 41:
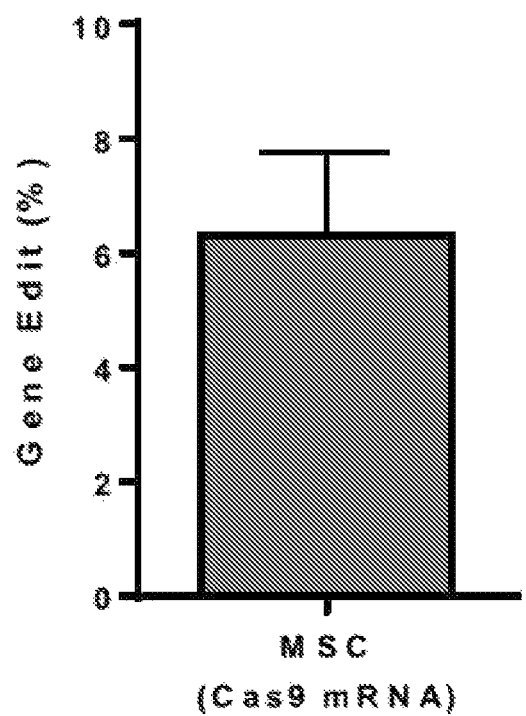

FIG. 41 is a bar graph depicting the edit efficiency using Cas9 mRNA. Delivery of Cas9 mRNA and guide RNA by Delivery Platform technology induced edit in MSC Like reference symbols in the various drawings indicate like elements.

DETAILED DESCRIPTION

To date, the CRISPR-Cas9 system has been most commonly delivered into cells in the form of plasmid DNA, which encodes for the three components, either as separate or combined plasmids. mRNA encoding for Cas9 has also been used (Liang et al., (2015) J Biotechnol 20; 208:44-53). Cas9 protein has been used as an alternative to a Cas9-encoding plasmids or mRNAs. Interestingly, Cas9 ribonucleoproteins (RNPs comprising Cas9), in which purified Cas9 protein is complexed with gRNA prior to delivery into cells, have recently been reported to provide several benefits over plasmid and mRNA approaches, for example, as described in: Cho S W, Lee J, Carroll D, Kim J S, Lee J. Heritable gene knockout in *Caenorhabditis elegans* by direct injection of Cas9-sgRNA ribonucleoproteins. *Genetics*. 2013. 195(3):1177-80; Sung Y H, Kim J M, Kim H T, Lee J, Jeon J, Jin Y, Choi J H, Ban Y H, Ha S J, Kim C H, Lee H W, Kim J S. Highly efficient gene knockout in mice and zebrafish with RNA-guided endonucleases. Genome Res. 2014. 24(1):125-131; Kim S, Kim D, Cho S W, Kim J, Kim J S. Highly efficient RNA-guided genome editing in human cells via delivery of purified Cas9 ribonucleoproteins. *Genome Res.* 2014. 24(6):1012-9 (hereinafter "Kim et al."); Lin S, Staahl B T, Alla R K, Doudna J A. Enhanced homology-directed human genome engineering by controlled timing of CRISPR/Cas9 delivery. eLife. 2014. 15; 3:e04766; Zuris J A, Thompson D B, Shu Y, Guilinger J P, Bessen J L, Hu J H, Maeder M L, Joung J K, Chen Z Y, Liu D R. Cationic lipid-mediated delivery of proteins enables efficient protein-based genome editing in vitro and in vivo. *Nat Biotechnol.* 2015. 33(1):73-80; Liang X, Potter J, Kumar S, Zou Y, Quintanilla R, Sridharan M, Carte J, Chen W, Roark N, Ranganathan S, Ravinder N, Chesnut J D. Rapid and highly efficient mammalian cell engineering via Cas9 protein transfection. *J Biotechnol.* 2015. 20; 208:44-53 (hereinafter "Lin et al."); and Schumann K, Lin S, Boyer E, Simeonov D R, Subramaniam M, Gate R E, Haliburton G E, Ye C J, Bluestone J A, Doudna J A, Marson A. Generation of knock-in primary human T cells using Cas9 ribonucleoproteins. *Proc Natl Acad Sci USA*. 2015. 18; 112(33):10437-42, the entire content of each of which is incorporated herein by reference.

Gene editing nucleases, including ZFN have been described in Bhakta, M. et al., *Genome Research* 23:530-538; 2013, and Beerli, R. et al., *Proc. Natl. Acad. Sci* v. 95 pp 14628-14633; 1998, TAL has been described in Cermak, T. et al., *Nucleic Acids Research* 2011, v. 39, no. 12, Miller, J. et al., *Nature Biotechnology* vol. 29 no. 2; 2011, Christian, M. et al., *Genetics* 186:757-761; 2010, Deng, D. et al, *Science* 2012: v. 335 p. 720, and Boch, J. et al., *Science* 2009: v. 326 p. 1509, the entire content of each of which is incorporated herein by reference. Additionally, Cre has been described in Chevalier, B. et al., *Nucleic Acids Research* 2001, v. 29 no. 18, the entire content of which is incorporated herein by reference. MegaTal has been described in Sather, B. et al *Sci Transl Med* 7(307) 2015, Ibarra, G. et al., *Molecular Therapy-Nucleic Acids* (2016) 5, e352, Osborn, M. et al., *Molecular Therapy* v. 24 no. 3, 570-581 (2016); Wang, Y. et al., *Nucleic Acid Research* 2014; v. 42, 6463-6475; and Gaj, T. et al., *Cold Spring Harbor Perspectives in Biology* 2015, each of which is incorporated herein by reference. Cas9 has been described in Wiedenheft, Bl. et al., *Nature* 2012; v. 482; 331, Fineran, P. et al., *Virology* 2012; 433; 202-209, and Hsu, P. et al., *Cell* 2014; v. 157; 1262-1278, the entire content of each of which is incorporated herein by reference.

Plasmids and mRNA can be silenced in some cell types while other cell types can be refractory to DNA transfection. RNPs have been shown in several studies to produce both more rapid and more efficient editing than plasmid transfection. This may be due to the direct introduction of the fully formed complex, which can function immediately in the cell and does not require transcription, translation, and assembly as with plasmids. RNPs have also been reported to be less toxic than plasmid DNA. This may be because exogenous DNA per se can be toxic to some cells or because the half-life of the RNPs is significantly shorter than that of plasmids, which produce longer-term expression of these foreign mRNAs and proteins. Importantly, the shorter expression time of RNPs has been also associated with fewer off-target edits compared to plasmids presumably because the duration of activity of the Cas9 protein is reduced. Plasmids can also integrate randomly in the genome or at Cas9-generated sites. While the latter event can at least be predicted and monitored, the former can be difficult to detect and so can be more problematic. Regardless of the site of integration, these foreign sequences can cause host immune responses, which creates challenges for the use of gene-edited stem cells or primary cells in clinical applications. Furthermore, cells transfected with plasmids for clinical applications are regarded as genetically modified by regulatory authorities and as such are subject to lengthy and costly regulatory procedures.

The present subject matter provides for vector-free (e.g., viral vector-free) delivery of a payload across a plasma membrane. In some embodiments, the delivery does not involve an expression vector. In particular, it has been discovered that intracellular delivery of materials can be achieved by contacting a cell (and/or population of cells) with an aqueous solution that includes an alcohol and the delivery materials (e.g., the payload). The alcohol acts to permeabilize the membrane to allow the payload to translocate across the membrane. But permanent or severe (e.g., irreversible) damage to the cell may occur (adversely affecting cell viability) when the volume of aqueous solution that contacts the cell is too large and/or exposure occurs for too long a time. Conversely, intracellular delivery of materials is not achieved when the volume of aqueous solution that contacts the cell is too small and/or exposure occurs for too short a time. Thus, to achieve delivery of a payload across a plasma membrane while maintaining cell viability, an appropriate volume of aqueous solution can be applied and/or the length of exposure can be controlled.

The appropriate volume of aqueous solution that is contacted to a population of cells can vary based on the intended application, for example, based on (e.g., be a function of) number of cells in the population, exposed cell surface area, cell size, makeup of the aqueous solution, payload, technique of contacting the aqueous solution to the population of cells, and the like.

The delivery platform is used to deliver Cas9 RNPs to cells such that genome editing is achieved.

Vector-Free Genome Editing

Figure 1:
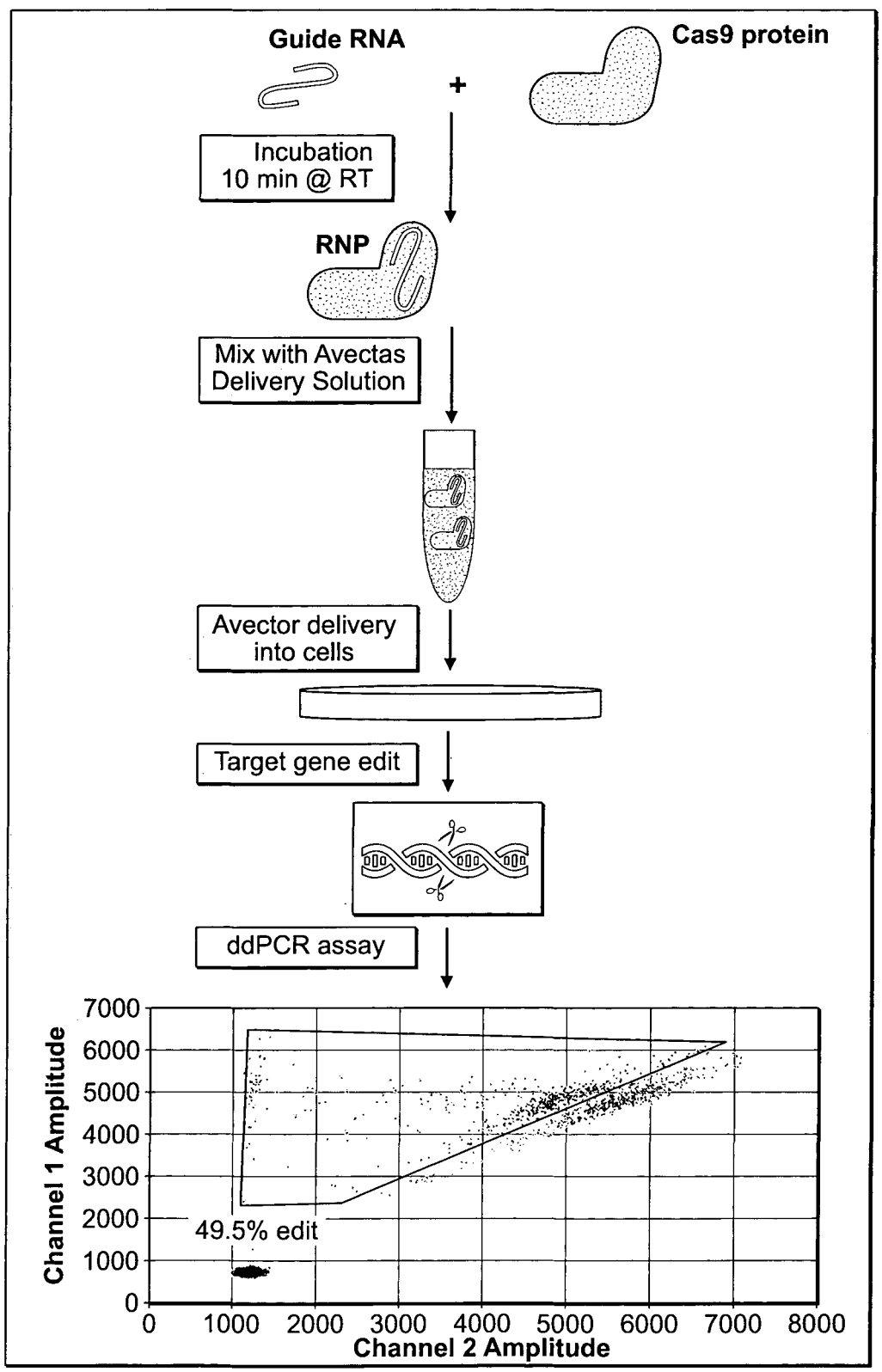
FIG. 1 is a cartoon illustrating an scheme to edit a target gene in A549 cells. Guide RNAs are delivered in the form of sgRNA. Dual-RNAs are chemically synthesized. sgRNA1s are transcribed in vitro. Guide RNAs are incubated with Cas9. Cas9:gRNA complexes are delivered into A549 cells using the Delivery Platform. Following cleavage with Cas9 and non-homologous end joining (NHEJ), the DNA is harvested from the cells and the edit is detected using droplet digital PCR (ddPCR) and drop-off probe assay.

In order to determine whether genome editing could be achieved by delivering Cas9 RNPs using the Delivery Platform technology, a strategy to delete a region from the target gene in the A549 human lung cell line is devised (FIG. 1). Cas9-mediated cleavage would be followed by non-homologous end joining (NHEJ). PCR primers, that flank the target region, and internal probes that act as a reference and a drop-off probe are designed. If editing is successful a ddPCR assay would result in a separation of droplets depicting where the drop-off probe is unable to bind in the edited genes and only the reference probe binds.

Two guide RNA approaches are taken using 2-part guide RNAs and single guide RNAs. For the 2-part guide RNA approach, a 42 bp CRISPR RNA (crRNA) molecule is designed to target the selected region within the target gene. A 69 bp trans-activating crRNA (tracrRNA or trRNA) is also designed. The crRNA and tracrRNA molecules are chemically synthesized and the tracrRNA molecule is labelled with FAM. For experiments, tracrRNA is incubated with crRNA to form a 2-part guide RNA molecule. For the single guide RNA approach, a sgRNA corresponding to the target sequence is in vitro transcribed from DNA templates.

Cas9 RNPs are formed by incubating Cas9 protein with either the 2-part guide RNA or the single guide RNA.

General Definitions and General Techniques

Unless specifically defined otherwise, all technical and scientific terms used herein shall be taken to have the same meaning as commonly understood by one of ordinary skill in the art (e.g., in cell culture, molecular genetics, and biochemistry).

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

As used herein, the term "about" in the context of a numerical value or range means±10% of the numerical value or range recited or claimed, unless the context requires a more limited range.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg Guide RNA (gRNA) can be used in two formats: crRNA and tracrRNA can be used in the form of a duplex RNA (or "dual-RNA") or can be engineered a single-guide RNA (sgRNA) molecule. As used herein, "gRNA" refers to a CRISPR-Cas system guide RNA. The term "gRNA" may refer to a combination of crRNA with a tracrRNA (dual-RNA) or a single RNA molecule comprising both a crRNA and a tracrRNA sequence (sgRNA).

As used herein, a complex means an association of molecules by a non-covalent interaction. For example, a complex may comprise two or more molecules that are hydrostatically associated with each other, e.g., via hydrogen bonds. A non-limiting example of a complex is an RNP comprising a Cas protein and a gRNA.

As used herein, a "gene editing protein" is a protein that cleaves a sugar-phosphate backbone of a DNA molecule or a protein that binds target DNA with sufficient affinity to reduce gene expression. A non-limiting example of a protein that binds target DNA with sufficient affinity to reduce gene expression is nuclease dead Cas9 (dCas9), i.e., a Cas9 that cannot cleave DNA. An example of a dCas9 is a D10A and H840A double mutant of a Cas9 protein having the amino acid sequence set forth as SEQ ID NO:1.

As used herein, an "expression vector" is a DNA or RNA vector that is capable of effecting expression of one or more polynucleotides. Preferably, the expression vector is also capable of replicating within the host cell. Expression vectors can be either prokaryotic or eukaryotic, and are typically plasmids. Expression vectors of the present invention include any vectors that function (i.e., direct gene expression) in host cells of the present invention, including in one of the prokaryotic or eukaryotic cells described herein, e.g., gram-positive, gram-negative, pathogenic, non-pathogenic, commensal, cocci, bacillus, or spiral-shaped bacterial cells; archaeal cells; or protozoan, algal, fungi, yeast, plant, animal, vertebrate, invertebrate, arthropod, mammalian, rodent, primate, or human cells. Expression vectors of the present invention contain regulatory sequences such as transcription control sequences, translation control sequences, origins of replication, and other regulatory sequences that are compatible with the host cell and that control the expression of a polynucleotide. In particular, expression vectors of the present invention include transcription control sequences. Transcription control sequences are sequences which control the initiation, elongation, and termination of transcription. Particularly important transcription control sequences are those which control transcription initiation such as promoter, enhancer, operator and repressor sequences. Suitable transcription control sequences include any transcription control sequence that can function in at least one of the cells of the present invention. A variety of such transcription control sequences are known to those skilled in the art. In preferred embodiments, the methods do not comprise the use of viral vectors such as adenoviruses to deliver nucleic acid molecules or constructs.

Payload compositions such as polynucleotides, polypeptides, complexes, or other agents may be purified and/or isolated. Specifically, as used herein, an "isolated" or "purified" compound, nucleic acid molecule, polynucleotide, polypeptide, or protein, or a complex comprising, e.g., a protein and a polynucleotide, is substantially free of other cellular material with which it naturally occurs, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. Examples of a an isolated or purified nucleic acid molecule include: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones.

Example 1: The Following Materials and Methods were Used to Generate the Data Described Herein Cells and Cell Culture A549 cells (A549 European Collection of Cell Cultures (ECACC) cells were purchased through Sigma-Aldrich Corp. (Cat No 86012804)(St. Louis, Mo., USA) and Beas-2B (Sigma-Aldrich Corp Cat. No. 95102433) and were routinely cultured in DMEM (Gibco) supplemented with 5% fetal bovine serum and 2 mM L-glutamine (Gibco). Jurkat cells (European Collection of Authenticated Cell Cultures; ECACC) were grown and maintained in RPMI 1640 (Gibco) supplemented with 10% (v/v) FBS (Sigma), and 1% (v/v) Penicillin/Streptomycin at 37° C. with 5% $CO_2$. Primary human PBMC were freshly isolated and were maintained in RPMI 1640 supplemented (Gibco) with 10% (v/v) heat inactivated FBS, 0.01% (v/v) 2-βmercaptoethanol (lifesciences) and 1% (v/v) L-glutamine at 37° C. with 5% $CO_2$. CD34+bone marrow-derived cells (HSC) were purchased from Lonza and were grown and maintained in HPMG-Hematopoietic Growth Medium (Lonza), supplemented with the growth factors SCF (25 ng/ml), TPO (50 ng/ml) and FLT-3 (50 ng/ml). Culture was maintained for 1 week at 37° C. with 5% $CO_2$ and media changed every 3 days.

Delivery Using Delivery Platform

The Delivery System includes a delivery apparatus, device, or instrument and a permeabilizing delivery solution (FIG. 6 depicts a graphical representation of the delivery mechanism). The delivery device includes an atomizer held on an adjustable x-y-z axis over a plate positioner platform. The atomizer is connected via tubing to a 5 bar compressor. A positioning collar allows centering of the spray over the well and the plate positioner platform enables reproducible well positioning under the atomizer. The payload is pipetted into a delivery port located at the top of the atomizer and the spray is generated using a spray actuator button. A preferred delivery solution includes 32 mM sucrose, 12 mM potassium chloride, 12 mM ammonium acetate, 5 mM HEPES and 25% ethanol), and optionally 2.5 mM $MgCl_2$, in molecular grade water (Sigma-Aldrich). Prior to addition of ethanol, the solution was adjusted to pH 7.4 and filter-sterilized. In the case of varied payload volume, the water volume was adjusted accordingly.

For delivery to adherent cells, cells were seeded in 48-well or 96-well culture plates (Nunc) (in other examples, culture plates with sample wells selected from 1, 6, 9, 12, 24, 48, 96, 384, and 1536 may be used) at densities that achieved 70-95% confluency at time of delivery. The supernatant was removed from the target well, the plate was placed on the plate positioner platform and the atomizer was positioned using the x-y-z axis to a distance of 31 mm from the spray head to the cell monolayer. 10 µl delivery solution was sprayed onto the cells. After 2 min at room temperature, 100 µl 0.5×-PBS was added onto the cells using a micropipette and cells were incubated at room temperature for 30 sec (for 48-well culture plates); 50 µl 0.5×-PBS was added onto the cells if using a 96-well plate. The 0.5×-PBS solution was removed and 100 µl fresh culture medium was added. After 3 hours, 100 U/ml penicillin and 100 g/ml streptomycin was added to each well. In the case of double spray, the procedure was repeated after 1-5 hour (e.g., 2 hour or preferably 4 hour) incubation from the first spray treatment. Cells were then incubated for 3 hours before the addition of antibiotics.

For delivery to suspension cells, $1.0 \times 10^6$ cells were placed into a 0.4 µm polyester membrane insert (Corning). The insert was placed into an in-house vacuum instrument and a vacuum of between −0.5 bar and −0.68 bar was applied to remove the culture medium. The insert was then placed into a 12 well plate and positioned under the nasal spray head. The spray procedure was carried out as described for adherent cells and when fresh culture medium was added, the cells were transferred to a fresh culture plate.

In Vitro Transcription of sgRNAs

In vitro transcription of sgRNAs was carried out using the Agilent (Santa Clara, Calif.) Sure Guide in vitro transcription kit as per manufacturer's guidelines.

Cas9 RNP Assembly and Delivery

Recombinant Cas9 protein was purchased from ToolGen, Inc and IDT-DNA. Guide RNA was generated using the SureGuide IVT kit (Agilent) according to manufacturer's guidelines. pCas9-GFP-382a2-384 plasmid was used as a positive control in assays. This plasmid contained CAS9-GFP and two gRNA. Cas9 protein (1 ug-20 ug) was premixed with in vitro transcribed gRNA (1 ug-20 ug) and the complex was incubated for 10 minutes at room temperature. The RNP complex was added to delivery solution (1×S buffer 25% EtOH) and delivered into cells using the delivery platform. For plasmid mediated expression of RGENs $1 \times 10^5$ cells were transfected with pCas9-GFP-382a2-384 using Lipofectamine 2000.

Western Blotting

Cells were scraped in ice-cold 1×PBS solution and centrifuged at 2200 rpm for 5 mins. The pellets were lysed in radioimmunoprecipitation (RIPA) buffer (Sigma, Dublin) and 25 mg of protein was loaded onto a 4-20% polyacrylamide gel. Following gel electrophoresis, the protein was transferred onto a nitrocellulose membrane and blocked in 5% milk/1×TBS 0.1% Tween-20 (Sigma, Dublin). Membranes were probed with primary antibodies overnight at 4° C. before secondary antibodies coupled with horse-radish peroxidase were applied for 1 hour at room temperature. Gel visualization was carried out using an ECL detection system (Gbox, Syngene, Cambridge UK). Primary antibodies used include anti-cas9 (Abcam, Cambridge U K), GAPDH (Sigma, Dublin).

Immunofluorescence

Immunofluorescence was carried out using a Millipore anti-Cas9 antibody at a 1/200 dilution.

PCR Assay for Edit

The reaction mix used for PCR was: H2O 30.5 μl, Buffer 5×10 μl, MgCl$_2$ 25 mM 5 μl, dNTP 10 mM 1 μl, PrimerF 10 μM 1 μl, PrimerR 10 μM 1 μl, Taq polymerase 0.5 μl, DNA 1 μl, Total Vol 50 μl.

Thirty-five cycles were used:

95° C.: 120 seconds(s)
95° C: 30 s
55° C: 30 s ×35
72° C: 45 s
72° C.: 5 minutes Viability Assays Viability and presence of apoptotic markers were analysed in Jurkat cells with the Annexin V and Propidium Iodide (PI) apoptosis detection kit (eBioscience) according to manufacturer's protocols. Cells were washed once in 1× binding buffer and re suspended in 1× binding buffer at a concentration of 1-5×10$^6$ cells/ml. APC conjugated Annexin V was added to 100 μl of cell suspension. Cells were incubated with fluorochrome for 15 mins at RT in the dark. After incubation, cells were washed with 1× binding buffer and resuspended in 100 μl 1× binding buffer. 5 μl PI was added to cells. Cells were analysed by flow cytometry no longer than 4 hours after staining. Percentage viable and apoptotic cells were calculated and graphed.

Analysis of Activation Markers

Jurkat cells were stimulated with 5 μg/ml PHA for 4 hr and 24 hr in a 24 well plate. Surface marker expression of the activation markers CD25 and CD69 was analyzed by flow cytometry. Cells were harvested and washed twice with PBS and re-suspended in FACs buffer at a concentration of 1×10$^6$ cells/ml. 100 μl of cell suspension was stained with CD25 APC (eBioscience) and CD69 PE (eBioscience) or with isotype controls for 15 min in the dark at 4° C. 500 μl was added to wash cells, and cells were re-suspended in 100 μl FACs buffer and analyzed on a BD Accuri C6 flow cytometer.

Figure 2:
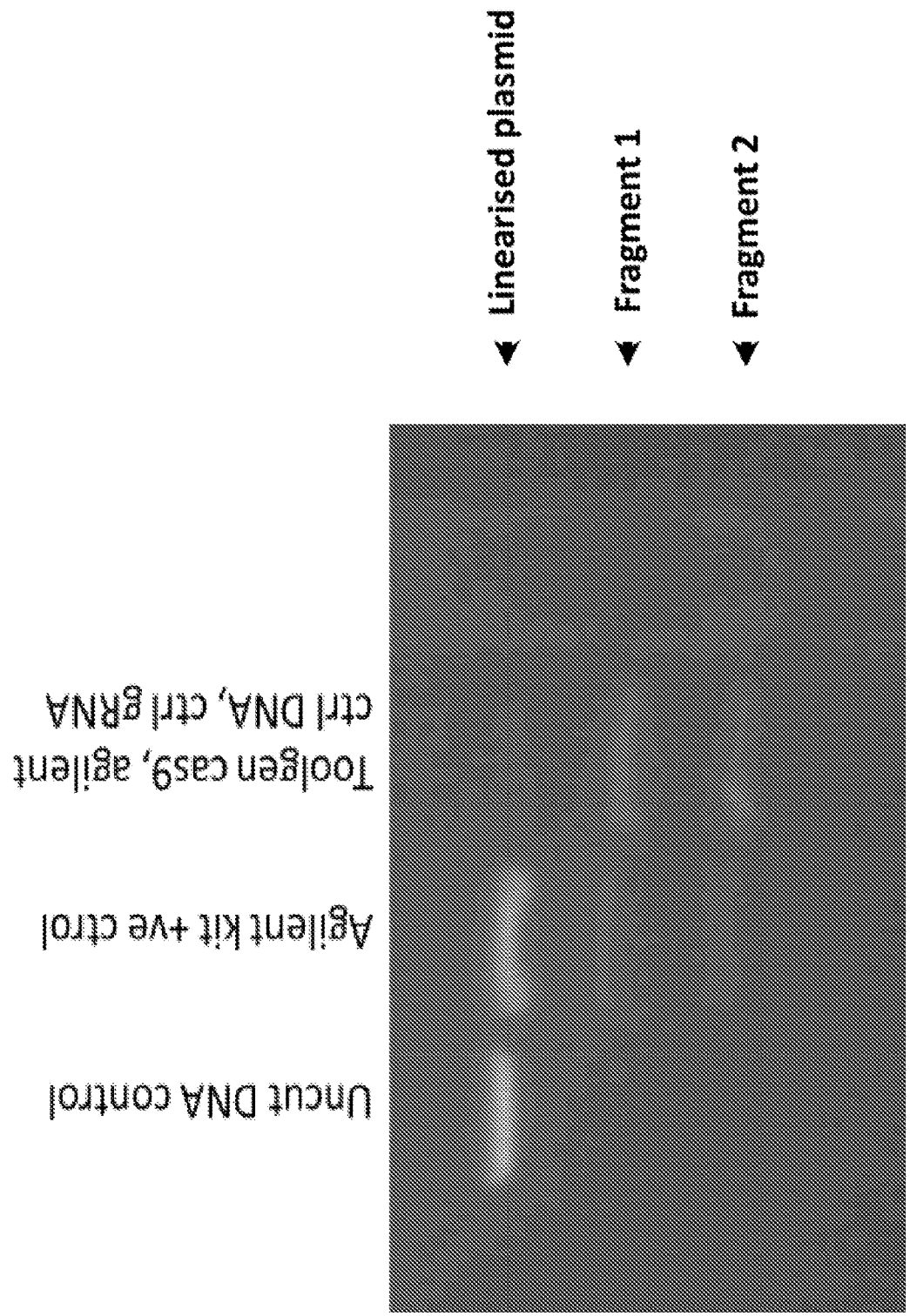
FIG. 2 is an image of an electrophoresis gel demonstrating the function of Cas9 protein in in vitro edit assay. Functionality of recombinant Cas9 purchased from Toolgen was confirmed in an in vitro edit assay. For the positive control, DNA, gRNA and Cas9 were provided in the Agilent kit and the predicted DNA fragments 1 and 2 were produced using these reagents. The Cas9 sourced from Toolgen (ToolGen, Inc., Seoul, South Korea) also successfully generated DNA fragments 1 and 2 using the control DNA and gRNA.

Effect of Delivery Solution Composition on Activity of Cas9 RNP in In Vitro Edit Assay The effect of the delivery solution composition on the activity of Cas9 protein was analyzed in an in vitro assay first. Cas9 protein (from Toolgen; Seoul, South Korea) was incubated with a control gRNA and a control plasmid supplied in the Agilent kit, along with kit buffer (Soln. A, Table 1). A cleaved product was observed (FIG. 2).

Figure 3:
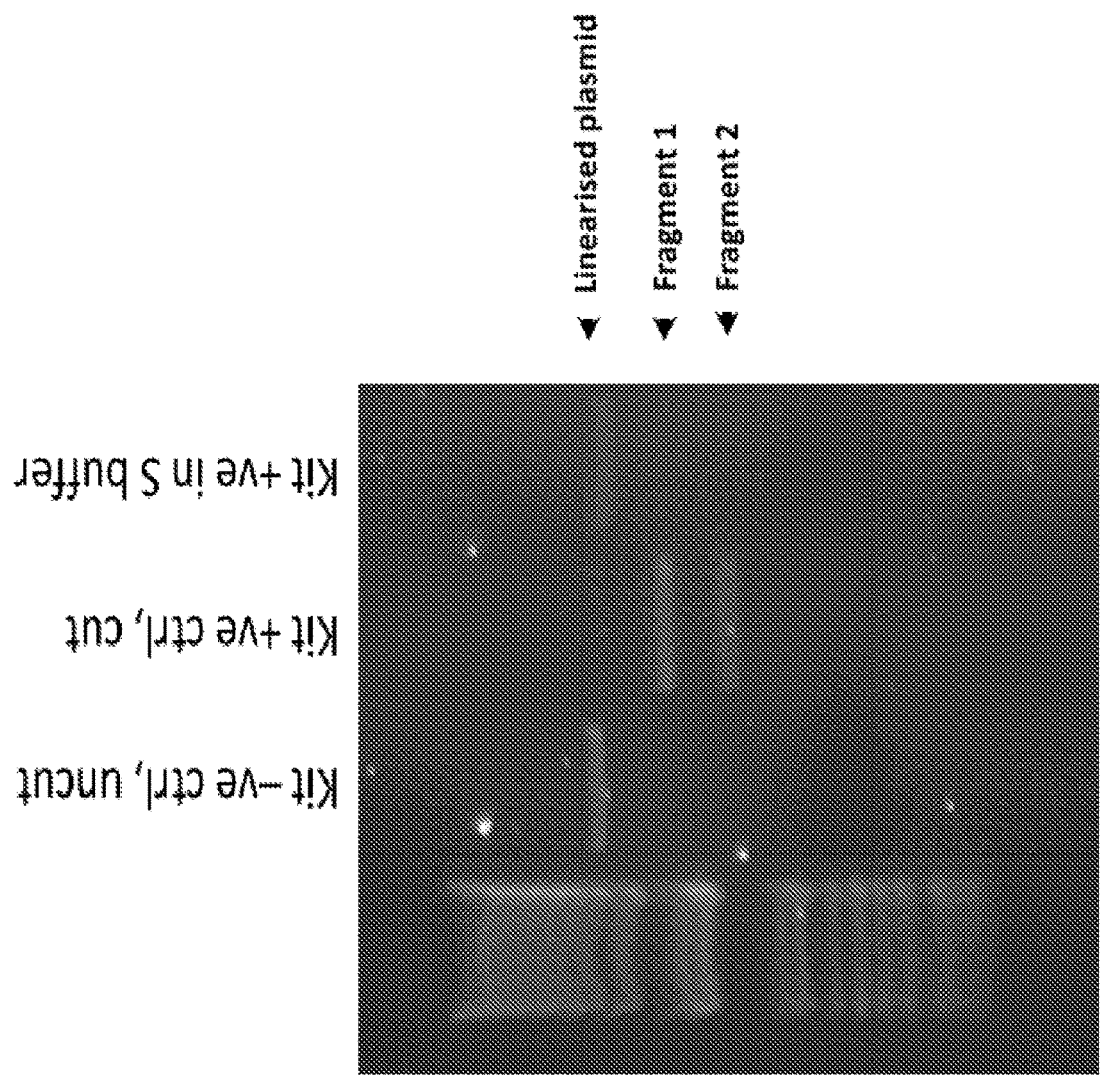
FIG. 3 is an image of an electrophoresis gel demonstrating the function of Cas9 protein in delivery solution in an in vitro edit assay. The Agilent in vitro assay was carried out in either buffer provided with the Agilent kit or in Delivery solution w/o ethanol (S buffer). The predicted DNA fragments 1 and 2 were produced using the Agilent buffer but not with S buffer.

The effect of replacing the kit buffer with delivery solution (without ethanol) was determined next (Soln. B, Table 1). A cleaved product was not observed (FIG. 3).

TABLE 1

Composition of buffers for in vitro edit.

|  | Soln A (ul) | Soln B (ul) | Soln C (ul) |
|---|---|---|---|
| Toolgen Cas9 (600 ng/ul) | 1 | 1 | 1 |
| Agilent Ctrl DNA (50 ng/ul) | 2 | 2 | 2 |
| Agilent Ctrl gRNA (1uM) | 1 | 1 | 1 |
| 10X Kit buffer (10X) | 2 | 0 | 0 |
| 10X Delivery solution (w/o EtOH) | 0 | 2 | 2 |

TABLE 1-continued

Composition of buffers for in vitro edit.

|  | Soln A (ul) | Soln B (ul) | Soln C (ul) |
|---|---|---|---|
| H$_2$O | 14 | 14 | 13 |
| MgCl$_2$ (25 mM) | — | — | 1 |
| Edit | Y | N | Y |

Figure 4:
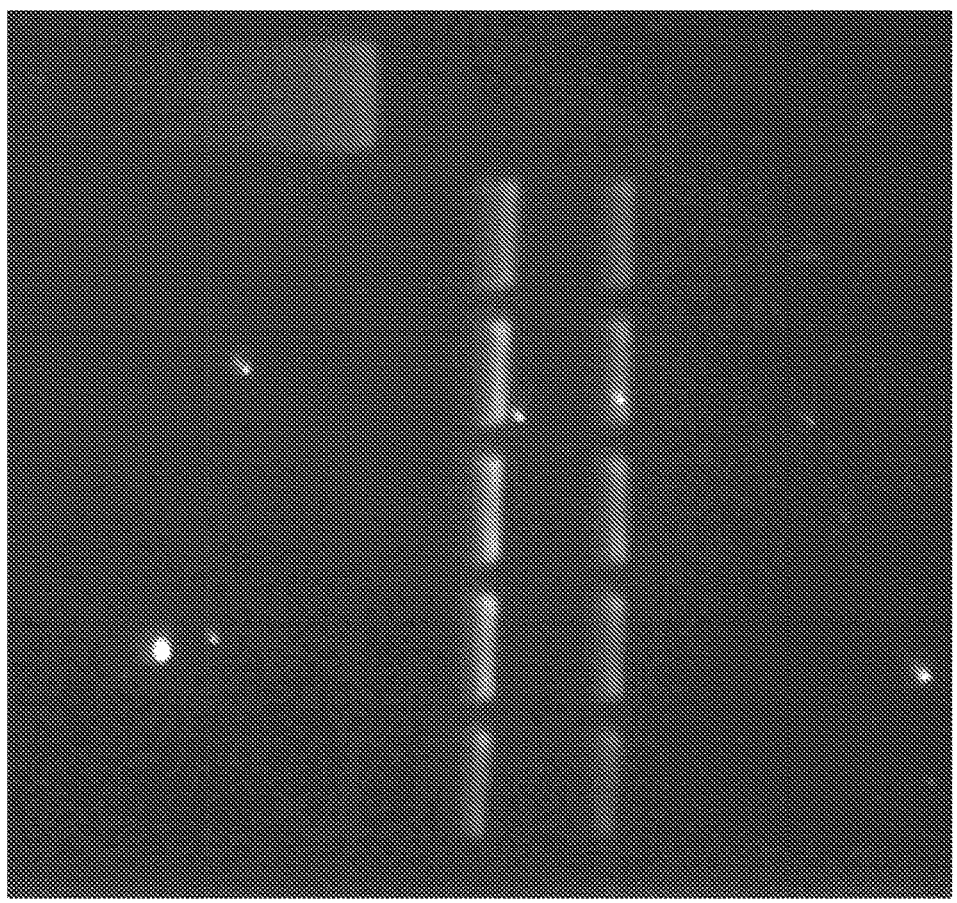
FIG. 4 is an image of an electrophoresis gel demonstrating the function of Cas9 protein in various ratios of delivery solution to kit buffer in an in vitro edit assay. Various ratios of 'Delivery solution w/o ethanol (S buffer)':'Agilent kit buffer' were tested using the Agilent in vitro assay. Ratios are shown in Table 2. The predicted DNA fragments 1 and 2 were produced in the presence of all ratio combinations except when Agilent kit buffer was absent (lane 6).
Figure 5:
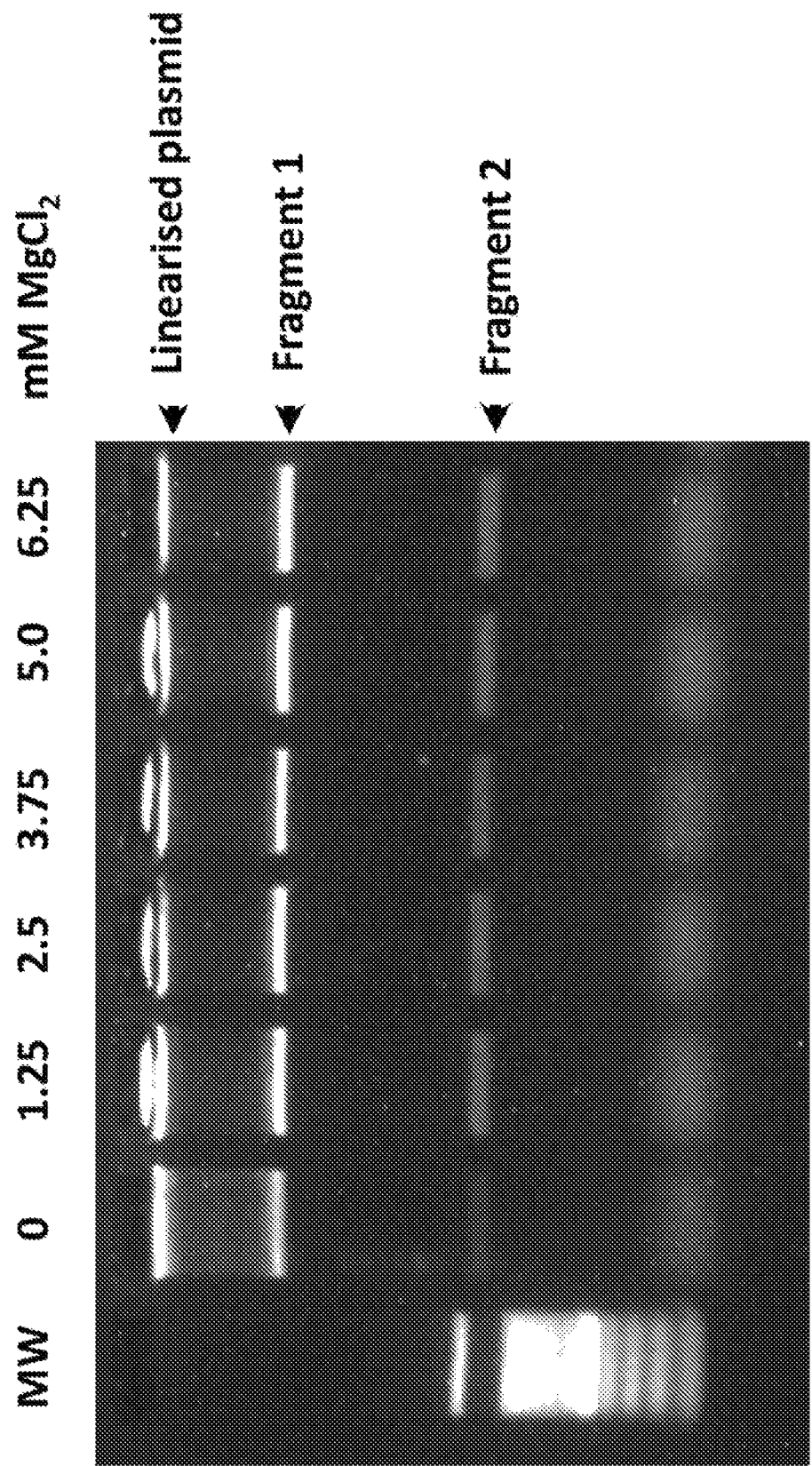
FIG. 5 is an image of an electrophoresis gel showing the effect of $MgCl_2$ concentration in the delivery solution on function of Cas9 RNP in an in vitro edit assay. The presence of $MgCl_2$ in the delivery solution allows Cas9 to function in delivery solution in the absence of ethanol. Increasing $MgCl_2$ concentrations do not have either a detrimental or a positive effect on the activity.

Experiments were carried out to determine the effect of delivery solutions. Various different ratios of delivery solution:Kit buffer were used. It was found that cleavage occurred at certain ratios of delivery solution up to 1.5 μl S buffer: 0.5 μl Kit buffer (Table 2 and FIG. 4). The effect of addition of MgCl$_2$ to the delivery solution/reaction buffer was therefore examined (Soln C, Table 1). The addition of 1.25 mM MgCl$_2$ to Soln B allowed the cleavage reaction to take place (FIG. 5). It appears that some cleavage can take place in the absence of MgCl$_2$, but this is sub-optimal and inconsistent. Therefore, 2.5 mM MgCl$_2$ was included in the delivery solution from this point on. A desirable delivery solution comprises: 32 mM sucrose, 12 mM KCl, 12 mM ammonium acetate, 5 mM HEPES, 2.5 mM MgCl$_2$, 15% ethanol, and 85% H$_2$O.

TABLE 2

Composition of buffers for in vitro edit where Agilent Kit buffer is mixed with Delivery solution (10x S buffer) in various ratios

|  | 1 | 2 | 3 | 4 | 5 | 6 |
|---|---|---|---|---|---|---|
| Ctrl DNA | 2 | 2 | 2 | 2 | 2 | 2 |
| gRNA | 2 | 2 | 2 | 2 | 2 | 2 |
| Cas9 | 1 | 1 | 1 | 1 | 1 | 1 |
| H2O | 14 | 14 | 14 | 14 | 14 | 14 |
| Kit 10x Buffer | 2 | 1.8 | 1.5 | 1 | 0.5 | 0 |
| 10x S buffer | 0 | 0.2 | 0.5 | 1 | 1.5 | 2 |

The efficiency of the delivery platform solution containing 15% ethanol and supplemented with 2.5 mM MgCl$_2$ to deliver a reporter payload, Ovalbumin-FITC (OVA-FITC) was examined. Surprisingly, the delivery of OVA-FITC appeared enhanced in the delivery solution containing 2.5 mM MgCl$_2$ compared to delivery solution without MgCl$_2$ (FIG. 8).

Therefore, for subsequent studies, the Cas9 RNP was delivered in a delivery solution containing 15% ethanol supplemented with 2.5 mM MgCl$_2$.

Delivery of Cas9 Protein and Time Course of Expression

Figure 9:
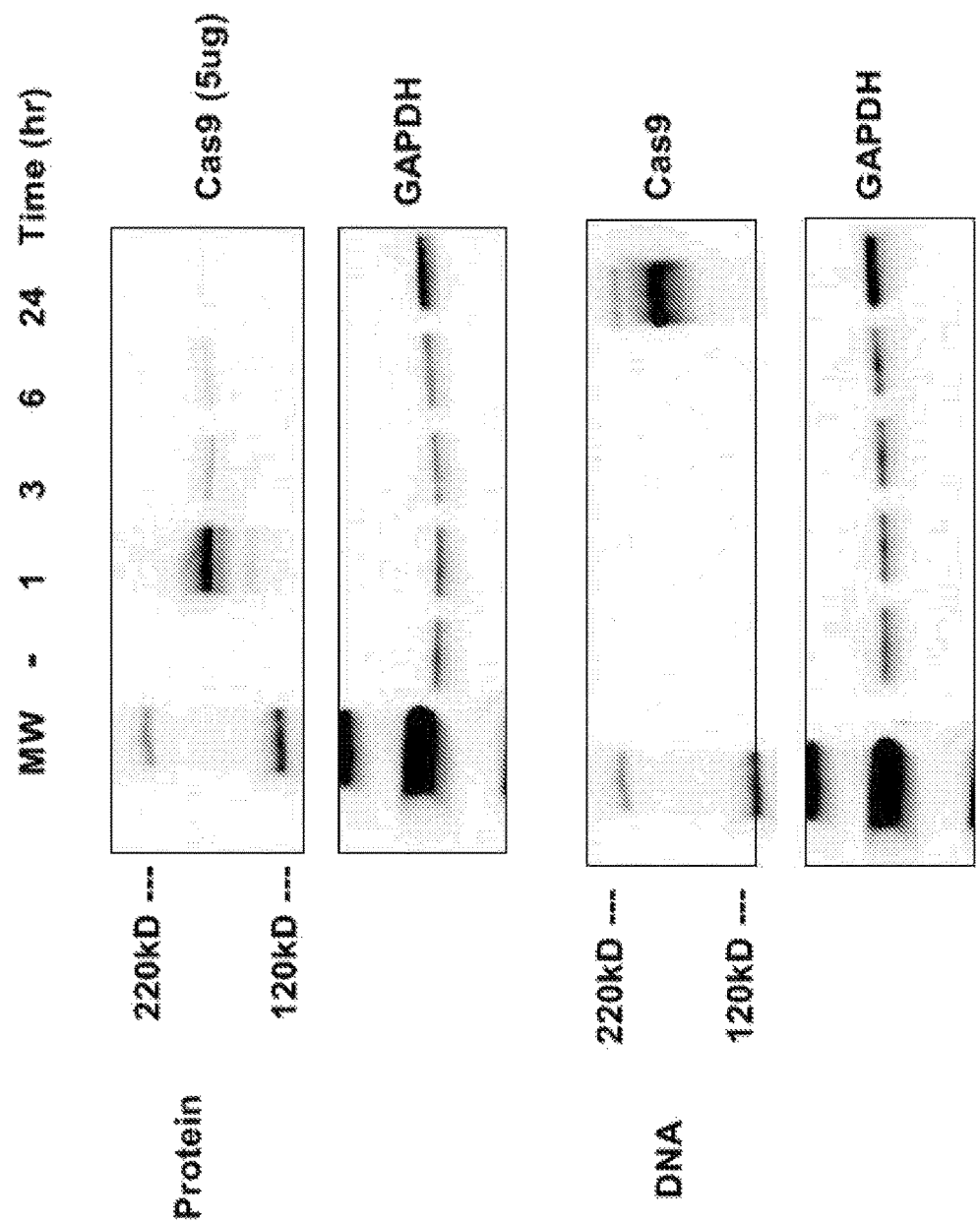
FIG. 9 is a set of western blots illustrating delivery of Cas9 protein resulting in rapid and transient protein expression compared to lipofected plasmid DNA. Cas9 protein was delivered to A549 cells and detected by Western blotting of cell lysates. When the delivery platform was used, Cas9 was detected at 1 hour post-delivery and levels decreased thereafter. GAPDH was used as a loading control. In contrast, when plasmid coding for Cas9 was delivered by lipofection to A549 cells, expression was not apparent for 6 hours.

Cas9 is usually delivered in the form of DNA encoding the Cas9 protein. However, DNA can persist in cells for days to months and this can lead to off-targets effects where the enzyme cleaves at non-specific sites in the cells. It has been suggested that delivering the protein form of Cas9 would result in a reduction in the duration of expression of the enzyme and therefore result in reduced off-target effects. Whether purified recombinant Cas9 protein without gRNAs could be delivered into A549 cells using the delivery platform was. The duration of expression compared with plasmid-mediated expression was also examined. Cas9 protein (5 μg) was delivered to A549 cells and expression was examined by Western blot analysis of cell lysates. Cas9 protein was detected in cells at 1 hour post-delivery and levels decreased thereafter (FIG. 9). In contrast, when a plasmid encoding Cas9 was lipofected into cells, expression was not observed before 6 hr and strong levels of expression were observed at 24 hr (FIG. 9).

Cas9 protein was also successfully delivered to BEAS-2B cells, Jurkat cells, human PBMC and HSC (Table 3).

TABLE 3

Cell types to which Cas9 protein was successfully delivered.

| Cell Types | Cas9 protein delivery |
|---|---|
| A549 | Yes |
| Beas-2B | Yes |
| Jurkat | Yes |
| PBMC | Yes |
| HSC | Yes |

Delivery of Cas9 Protein

With viral delivery of CRISPR/Cas9, it can be difficult to control the dose of editing tools delivered. It was therefore examined whether the Delivery Platform technology could deliver incremental doses of Cas9 protein.

A dose response was seen when increasing concentrations of Cas9 protein were delivered to A549 and Jurkat cells (FIGS. 10A and B).

Delivery of Cas9 Protein and RNPs—Sub-Cellular Localization

Because Cas9 RNPs function in the nucleus, the sub-cellular localization of Cas9 protein and Cas9 RNPs following delivery with the delivery platform was determined. Cy3-labelled Cas9 and FAM-labelled dual-RNAs were used to examine the localization of Cas9 and RNPs by fluorescence microscopy. In addition, Cas9 was detected by immunofluorescence using an anti-Cas9 antibody.

Figure 11A:
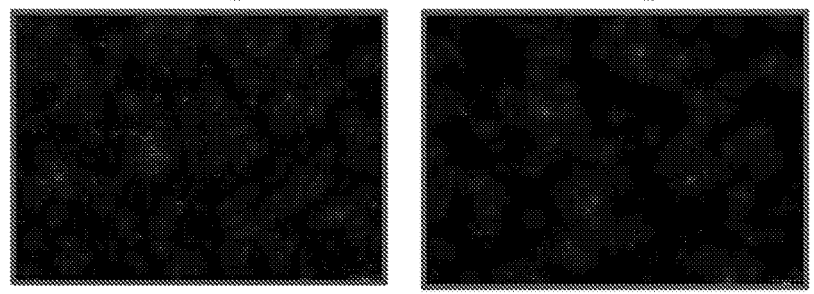
FIG. 11A-E are images illustrating sub-cellular localization of Cas9 protein after delivery into A549 cells.

1 ug Cas9-Cy3 protein was delivered into A549 cells using the delivery platform. At 1 hr post-delivery, Cas9 was observed throughout the cytoplasm and in the nucleus of cells (FIG. 11A).

Figure 11B:
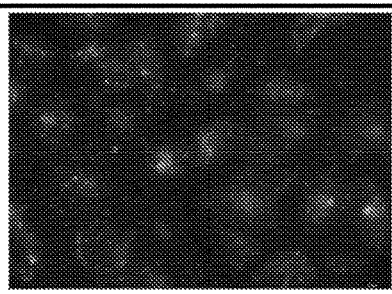

10 ug unlabelled Cas9 protein was delivered into A549 cells using the delivery platform and Cas9 was detected by immunofluorescence using an anti-Cas9 antibody. At 1 hr post-delivery, Cas9 was observed throughout the cytoplasm and in the nucleus of cells (FIG. 11B). The staining pattern was similar to that observed for Cas9-Cy3.

Figure 11C:
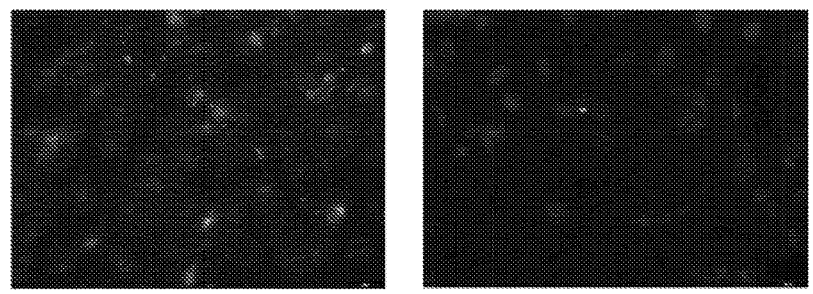

100 uM sgRNA1-FAM was delivered into A549 cells using the delivery platform. At 1 hr post-delivery, sgRNA1-FAM was observed throughout the cytoplasm and in the nucleus of cells (FIG. 11C).

Figure 11D:
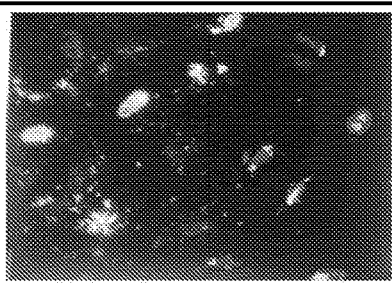

Next, the localization of RNPs was examined following delivery to A549 cells. Unlabeled Cas9 was complexed to sgRNA1-FAM and delivered using the delivery platform. At 1 hr post-delivery, sgRNA1-FAM was observed throughout the cytoplasm and in the nucleus of cells (FIG. 11D). The staining pattern appeared more 'speckled' than that of sgRNA1-FAM shown in FIG. 11C indicating that the sgRNA was indeed complexed to Cas9.

Figure 11E:
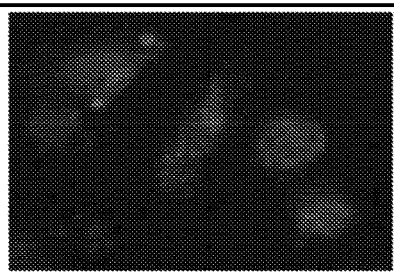

The localization of RNPs was then examined by immunofluorescence using an anti-Cas9 antibody. Unlabeled Cas9 was complexed to sgRNA1-FAM and delivered using the delivery platform. At 1 hr post-delivery, Cas9 was observed throughout the cytoplasm and in the nucleus of cells (FIG. 11E). The staining pattern was similar to that shown in FIG. 11D, as expected.

Effect of Delivery Platform-Mediated Delivery to Jurkat Cells, PMBC and HSC

Figure 7:
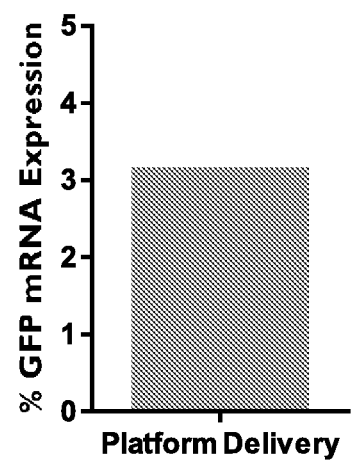
FIG. 7 is a bar graph illustrating the percent GFP mRNA expression in NK cells using the methods and delivery platform described herein.
Figure 12A:
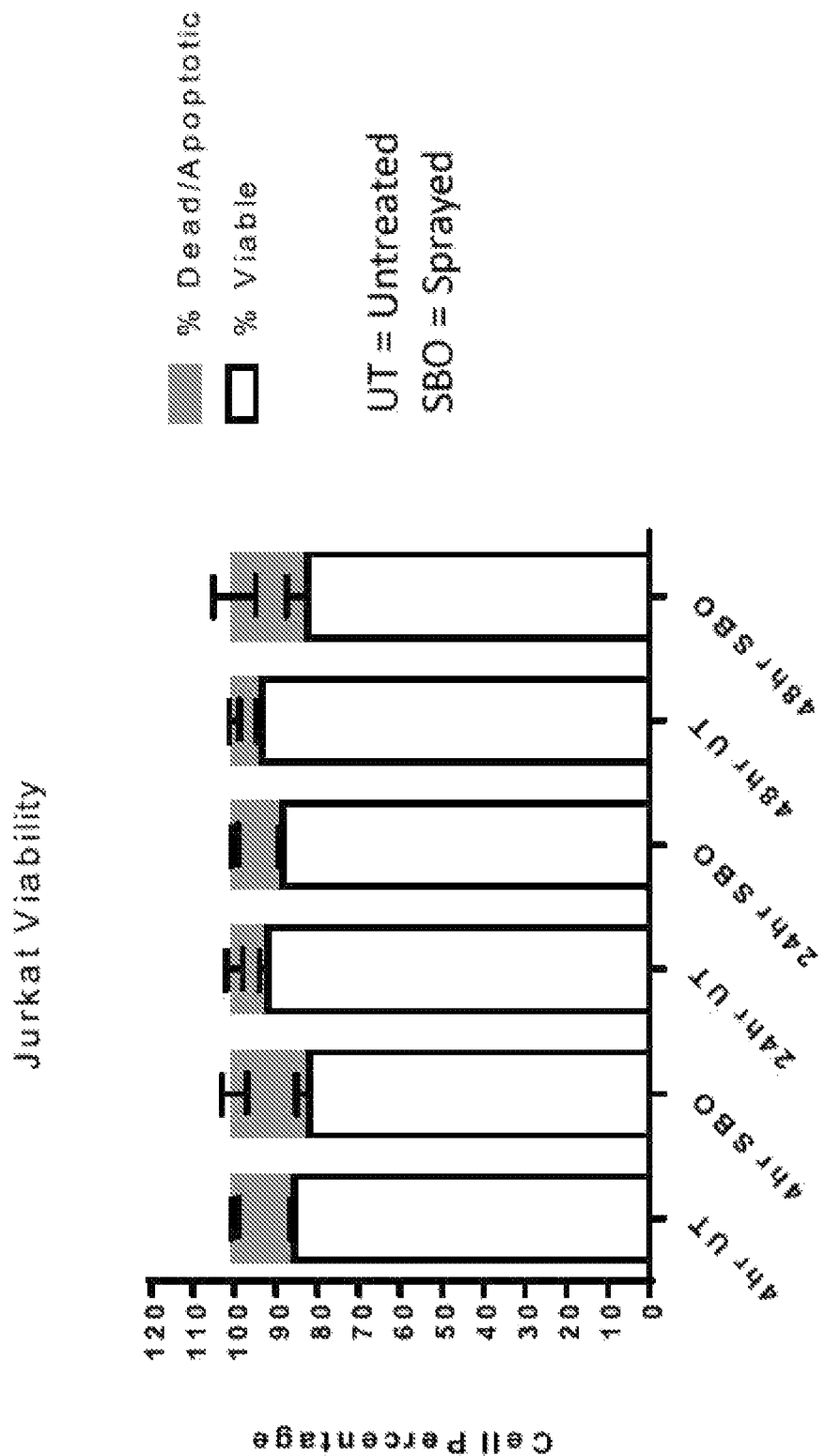
FIG. 12A-C are a set of graphs showing the effect of the delivery platform technology on the viability of Jurkat cells (FIG. 12A), human peripheral blood mononuclear cells (PBMCs) (FIG. 12B) and HSCs (FIG. 12C). Delivery solution without payload (SBO) was delivered to Jurkat cells, human PBMCs or HSCs. An Annexin V and propidium iodide assay demonstrated a minimal reduction in viability in each cell type. UT=untreated.
Figure 12B:
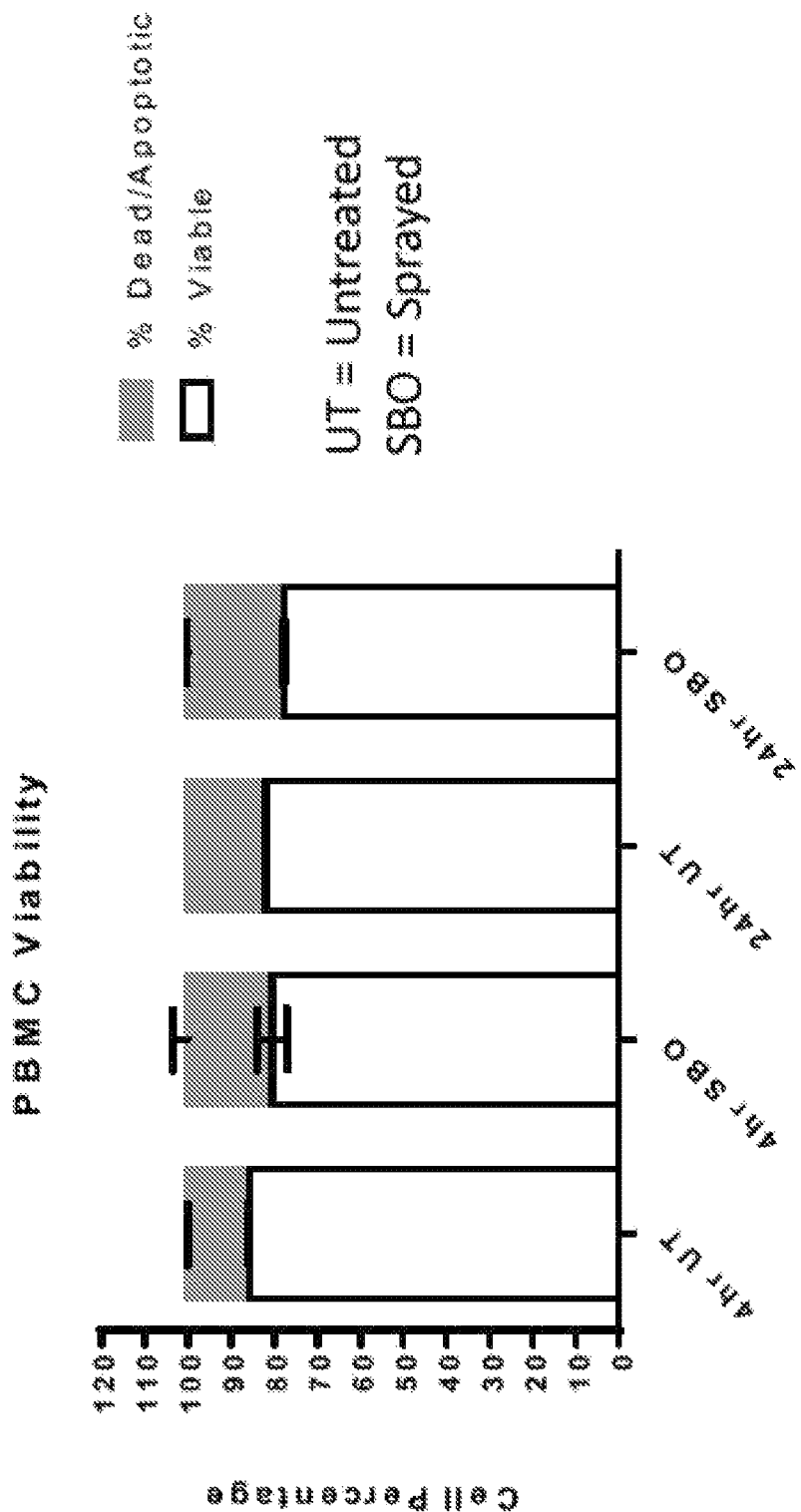
Figure 12C:
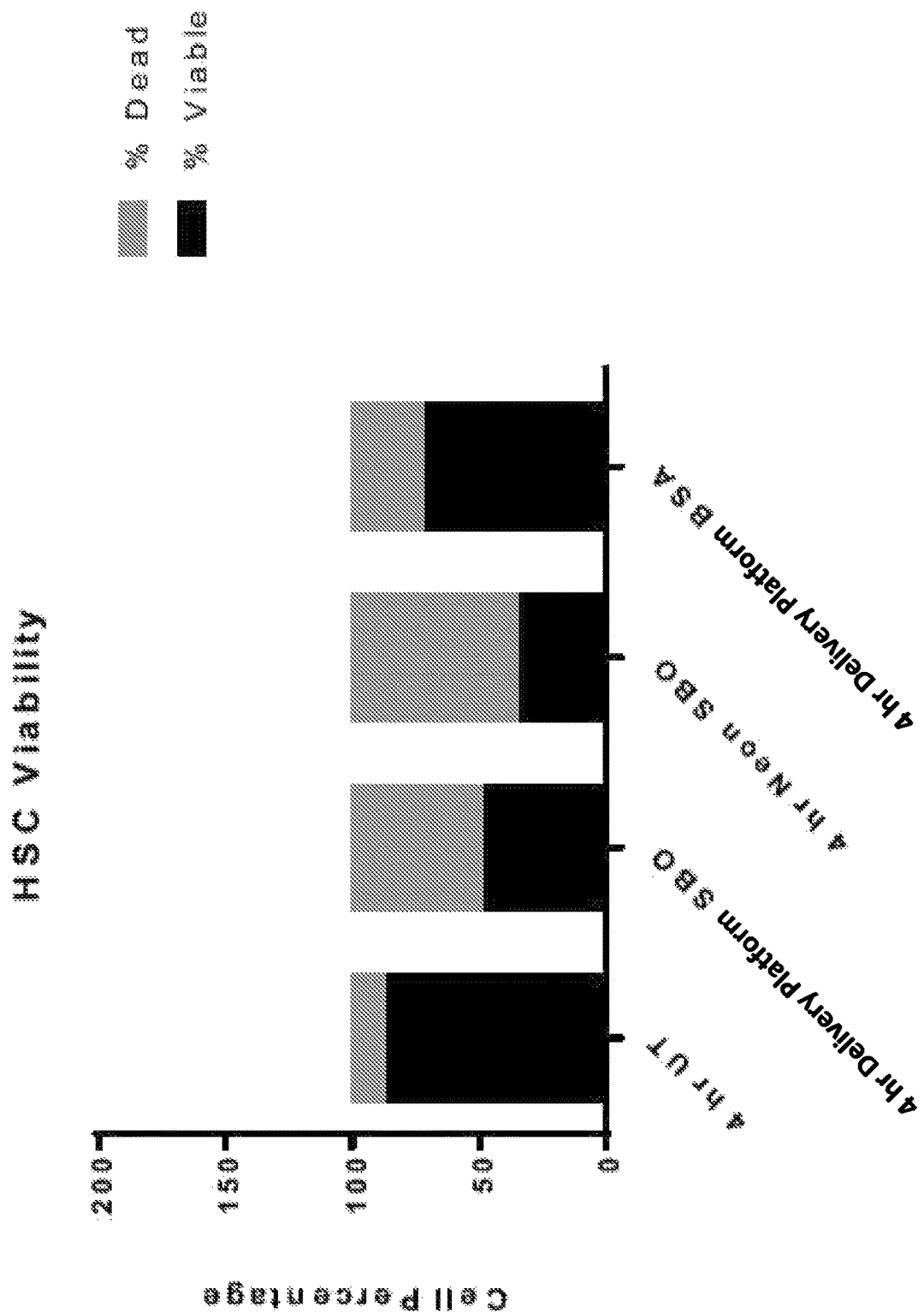

For clinical applications, it is critical that high rates of viability and functionality are retained by cells following delivery and transfection protocols. The effect of the Delivery Platform technology on the viability of Jurkat cells, PBMC and HSC was examined. For analysis of the effect of platform-mediated delivery, delivery solution without payload was delivered to Jurkat cells, human PBMC and HSC. Viability of cells post-delivery was examined by annexin V/propidium iodide (PI) staining. The viability of the cells was reduced minimally compared to untreated controls (FIG. 12). Additionally, GFP mRNA was delivered to primary NK cells (FIG. 7) and the cells had 96.6% viability.

Comparison of Viability and Efficiency: Ethanol Spray Delivery Vs Neon Electroporator Electroporation has been used to deliver Cas9 RNPs to cells in vitro (Kim et al., (2014) Genome Res 24(6):1012-9; Lin et al., (2014) eLife 15; 3:e04766; Liang et al., (2015) J Biotechnol 20; 208:44-53; Schumann et al., (2015) Proc Natl Acad Sci USA 18; 112(33):10437-42). However, electroporation is known to affect the viability and function of clinically relevant cells including T cells and stem cells. Therefore, the effect of platform-mediated delivery was compared with that of electroporation. Neon electroporation was used, which has been used by other groups (Liang et al., (2015) J Biotechnol 20; 208:44-53; Schumann et al., (2015) Proc Natl Acad Sci USA 18; 112(33):10437-42).

Figure 13A:
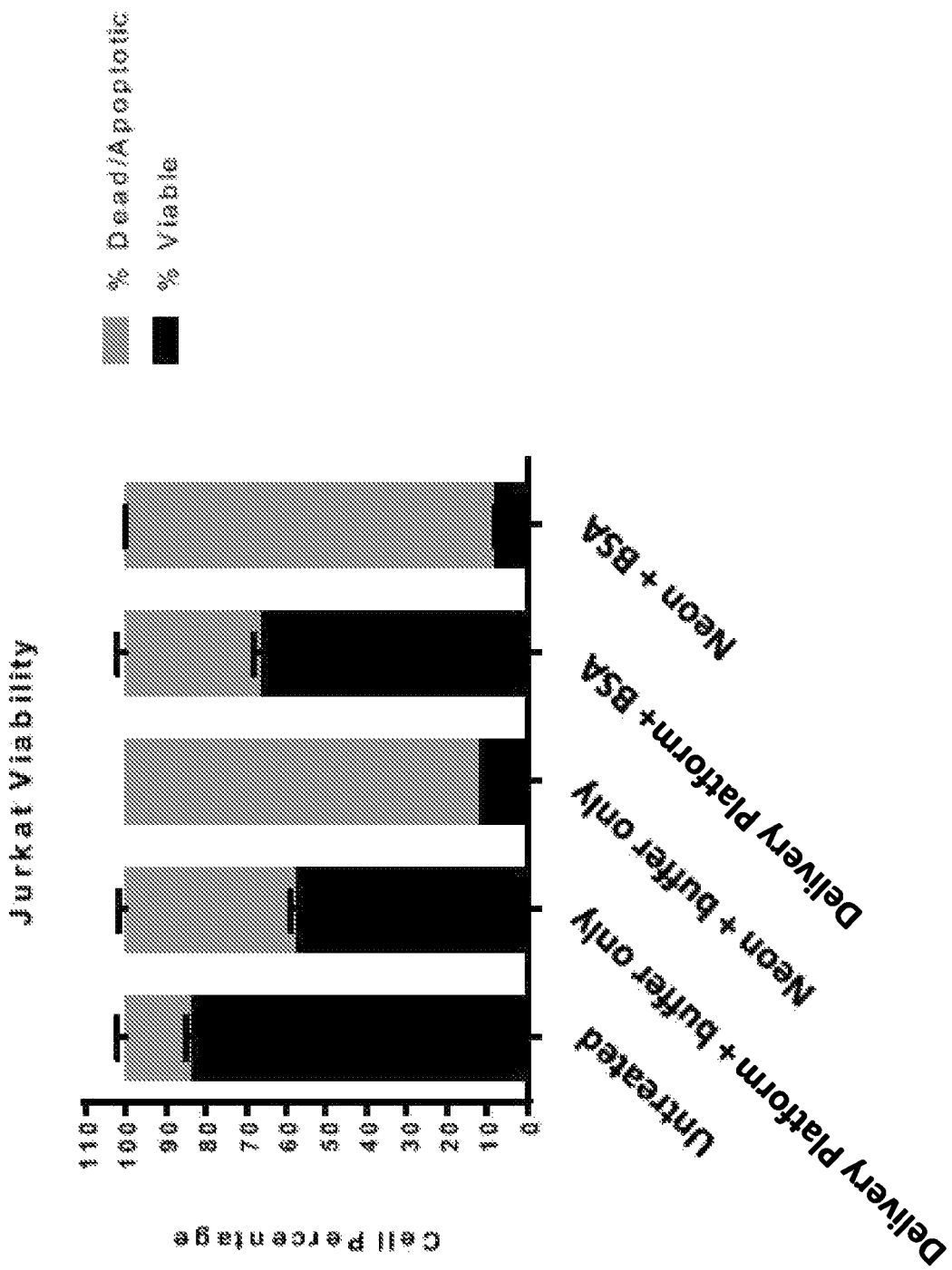
(FIG. 13A) Comparing the viability of Jurkat cells following delivery using Delivery Platform vs Neon.

Bovine serum albumin-FITC (BSA-FITC) was delivered to Jurkat cells and viability was determined at 24 hr post-delivery. With the delivery platform, viability was reduced from 81% in untreated controls to 65% in cells that received BSA-FITC (FIG. 13A). In contrast, viability levels dropped to 8% when BSA-FITC was delivered to cells by electroporation. Similar reductions in viability were seen when buffer only (without BSA-FITC) was delivered.

Figure 13B:
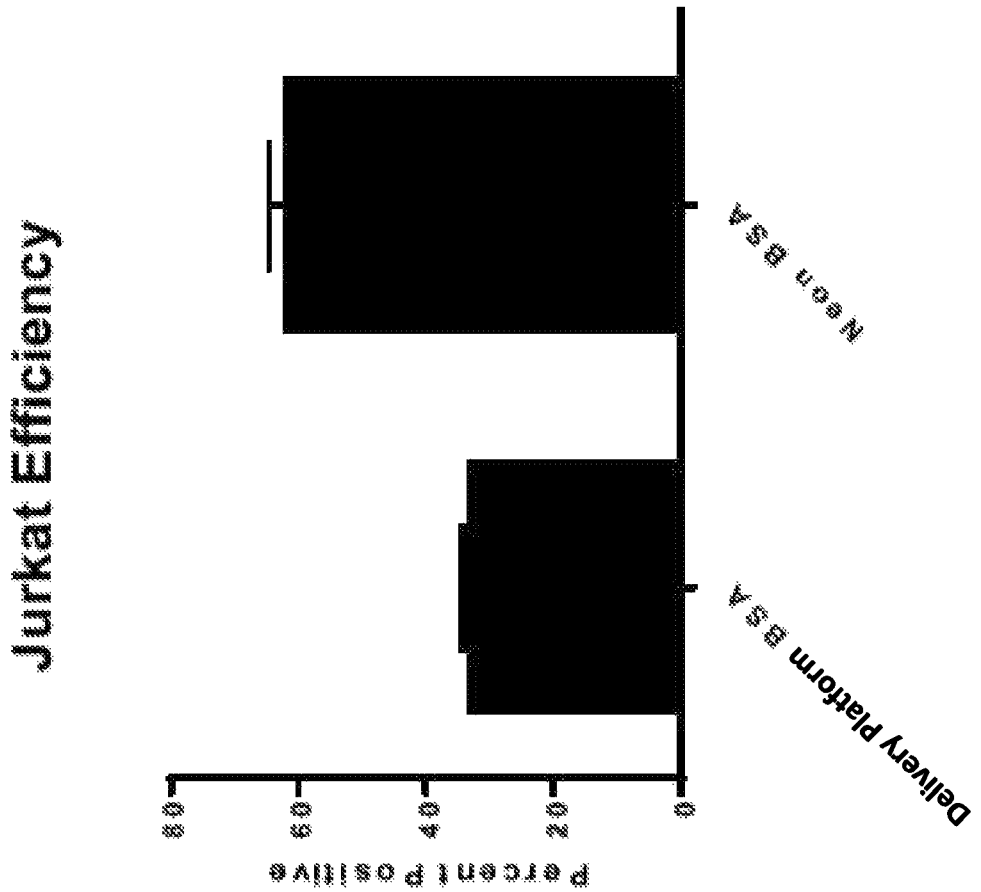
(FIG. 13B) The efficiency of delivery of BSA-FITC to Jurkat cells using Delivery Platform vs Neon electroporator.

The efficiency of delivery of BSA-FITC was examined by flow cytometry at 24 hr post-spray. With the delivery platform, of the 65% viable cells, 34% were positive for BSA-FITC (FIG. 13B). With electroporation, of the 8% viable cells, 62% were positive for BSA-FITC. Therefore, of the original starting populations, BSA-FITC was present in 22% cells following platform-mediated delivery and in 5% cells following electroporation.

Effect of Delivery Platform Technology-Mediated Delivery on Functionality of Primary Jurkat Cells Next, the effect of platform-mediated delivery on the functionality of Jurkat cells was examined. The delivery platform was used to deliver spray buffer only to cells. CD69 and CD25 are respectively early and late cell surface markers of T cell activation.

Delivery solution without payload (Spray buffer only, SBO) was delivered to cells using the delivery platform. Cells were stimulated with PHA and the expression of CD69 and CD25 was measured by flow cytometry at 4 hr and 24 hr post-stimulation respectively. Upregulation of CD69 and CD25 was observed in treated cells (FIG. 14).

Example 2: Establishment of In Vitro Edit Assay to Test Function of Gene Editing Tools and Effect of Delivery Solution on Function of Gene Editing Tools The Crispr Cas9 system of gene editing has been widely adopted. However, the majority of users utilize the DNA plasmid form of the Cas9 in combination with guide RNAs. Delivering the RNP version of the system was of interest because this was more transient and should therefore lead to fewer off-target effects. The requisite tools (recombinant Cas9 nuclease, single guides, 2-part guides) have recently become commercially available. Bespoke guide RNA sequences were designed based on corresponding plasmid sequences reported in the literature. A validation assay was performed to check the quality of the reagents. In order to assess the gene editing tools, an assay based on the Agilent SureGuide Cas9 Programmable Nuclease Kit in vitro edit test was developed. In this assay, the Cas9 protein was incubated together with the guide (single or 2-part) to form the RNP. This RNP was then incubated with a purified length of DNA (~250 to 750 bp) which contained the target site. If the edit was successful it would result in the creation of two strands of DNA which would be evident once separated on an agarose DNA gel. This assay served two purposes: firstly, it served as a quality control assay to check the functionality of the gene editing tools and secondly, it served to determine the effect of the delivery solution on the gene editing tools and specifically, the effect on Cas9/RNP activity. For the latter purpose, a solution of Cas9 or RNP was prepared in delivery solution, sprayed and then an aliquot of the sprayed solution was collected and used in the editing assay.

Materials

Agilent Sure Guide Cas9 Nuclease Kit: the kit provided Cas9 nuclease, control DNA target, control gRNA, 10×Cas9 digestion buffer (Agilent) and RNase free water. The optimized volumes for the control reaction are listed in Table 4. The various gRNA and DNA targets were synthesized or provided by IDT-DNA Cas9 (IDT-DNA). Delivery solution is described herein.

In Vitro Edit (IVE) Assay: Testing Function of Gene Editing Tools

This assay was based on the Agilent Sure Guide Cas9 Nuclease Kit. The optimized volumes for each component are listed in Table 4. DNA target, gRNA and Cas9 were provided in the kit to validate the procedure. All components, stored on ice, were added into test tubes suitable for a thermocycler in the proportions described in Table 4. Then the tubes were transferred into a thermocycler pre-warmed at 30° C. The following program was run:

30 min at 30° C.
15 min at 65° C.
Hold at 4° C.

Digested samples were then analyzed by gel electrophoresis where successful edit was confirmed by the presences of additional DNA bands—the size of which corresponded to the expected DNA fragments. This assay confirmed that the recombinant Cas9 protein and various guide RNAs used in these studies were functional.

TABLE 4

Component volumes for the IVE reaction*

| Component | Volume (µl) |
|---|---|
| Cas9 600 ng/µl | 1 |
| DNA Target 50 ng/µl | 2 |
| gRNA 1 µM | 1 |
| 10X Cas9 digestion buffer | 2 |
| RNase free water | 14 |
| Total | 20 |

All gRNA tested and the corresponding target DNA are listed here: sun sgGFP RNA with pCMV EGFR target DNA, sgRNA EGFP4 with EGFP target DNA, sgHPRT1 with HRT1 DNA as target, sgAAVS1 T1, sgAAVS1 T2 and AAVS1 T3 with AAVS1 as target DNA Testing Effect of Delivery Solution on Function Gene Editing Tools In this assay the IVE protocol was adapted to study the effect of the delivery solution and of the spray procedure on the functionality of Cas9 and RNP. To do so, Cas9 alone or as RNP (Cas9 complexed with gRNA) were first prepared in delivery solution and then used for IVE or sprayed and then collected for IVE. If edit occurred, that confirmed that the components of the RNP were capable of cutting the target DNA sequence, hence they were functional, despite the presence of ethanol and other chemicals in the delivery solution.

Solutions of Cas9 or RNP in delivery solution were made up as reported in Table 5. The RNP were formed by incubating Cas9 with gRNA for 15 min prior to adding S-buffer and water. Furthermore, corresponding samples were made up in water for comparison purposes. To make up the complex, 1:1 molar ratio Cas9/gRNA was used. In the case of Cas9 only solutions the gRNA was provided when IVE reactions were carried out (see Table 6).

TABLE 5

Composition of Cas9 solutions or RNP solutions

| Solution | Cas 9 10 µg/µl | sun sg GFP RNA 61 µM | S-buffer 10X with MgCl$_2$ 100 mM (µl) | EtOH (µl) | Water (µl) | Total volume (µl) |
|---|---|---|---|---|---|---|
| A | 1.2 | 0 | 0 | 0 | 18.8 | 20 |
| B | 1.2 | 0 | 0.5 | 3 | 15.3 | 20 |
| C | 2.0 | 2.0 | 1.0 | 6.0 | 29 | 40 |

Figure 17:
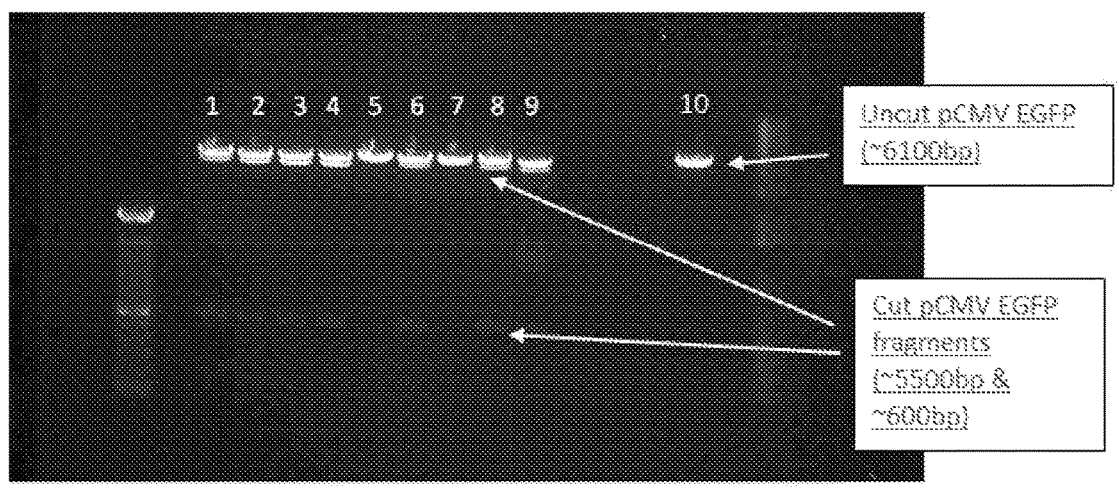
FIG. 17 is an image of an electrophoresis agarose gel illustrating the effect delivery solution on function of gene editing tools. Lane 1 is Cas9 600 ng/µl in RNase free water (positive ctrl); lane 2 is Cas9 600 ng/µl in RNase free water sprayed, lane 3 is Cas9 600 ng/µl in delivery solution; lane 4 is Cas9 600 ng/µl in delivery solution sprayed; lane 5 is complex Cas9/gRNA in delivery solution; lane 6 is complex Cas9/gRNA in delivery solution sprayed; lane 7 is complex Cas9/gRNA in delivery solution with EtOH added straight away; lane 8 is Cas9 in delivery solution containing 4 times more S-buffer; lane 9 is Alexa 488 Cas9 labelled in delivery solution; lane 10 is a negative ctrl (Cas9 in delivery solution, no gRNA added); the negative control where the DNA is not cut. Edit was observed in all samples except sample 7, where EtOH was added together with all other components (without preliminary 10 min incubation). For all other samples, a band for the fragmented DNA appeared close to the uncut DNA. Results indicated that neither the delivery solution nor the spray impeded the cutting activity of Cas9 and of the RNP. The agarose gel was a 1.0% gel containing cyber safe dye, and run at 100V for 60 minutes with gel loading dye.

All components, bar the ethanol, were added into a test-tube and incubated for 10 minutes. Then the ethanol was added. For each solution, aliquots of 1 µl (Cas9 solution) or 2 µl (RNP) were transferred into a test-tube for IVE testing, according to Table 6 and Table 7. To test the effect of the spray process on the RNP activity, other 10 µl aliquots were sprayed into empty wells of a 48 well plate and 1 or 2 µl solution were collected after spray and transferred into a PCR test tube. For IVE, see Table 6 and Table 7. Samples were digested as described above and then analyzed by means of agarose gel electrophoresis. A typical image of the gel is provided in FIG. 17.

TABLE 6

Component volumes per reaction, Agilent Cas9 buffer

| Component | Volume (µl) |
|---|---|
| Cas9 600 ng/µl (before or after spray) | 1 |
| pCMV EGFP Not1 82 ng/µl | 2 |
| Sun sg GFP RNA1 µM | 1 |
| 10X Cas9 Agilent buffer | 2 |
| RNase free water | 14 |
| Total | 20 |

TABLE 7

Component volumes per reaction, Agilent Csa9 buffer

| Component | Volume (µl) |
|---|---|
| Cas9 RNP 600/GFP gRNA 1:1 (sol C before or after spraying) | 2 |
| pCMV EGFP Not1 82 ng/µl | 2 |
| 10X Cas9 Agilent buffer | 2 |
| RNase free water | 14 |
| Total | 20 |

Example 3: Conjugation of Cas9 with Fluorescent Label for Visualization of Delivery into Cells To analyze whether Cas9 was entering cells following delivery using the Delivery Platform technology, conjugating the protein with a fluorescent label was explored. Cas9 labelling methods which target amine groups must be avoided, as they lead to precipitation of Cas9 due to its physical-chemistry characteristics. Therefore, Cas9 was labelled with the fluorescent tag, Alexa-488 maleimide, through the thiol group of cysteine (2 cysteine residues per molecule of protein). This reaction did not alter the overall charge of the protein at physiological pH. The experimental protocol followed was based on previous work (Zuris, J A et al., Nat Biotechnol 2015; 33(1) 73-80).

Materials

Cas9 was purchased either from Toolgen Genome Engineering (South Korea) or IDT Integrated DNA Technologies (USA). TCEP (tris(2-carboxyethyl)phosphine), Hepes, glycerol and KCl were of analytical grade and purchased from Sigma Aldrich. Alexa 488 maleimide (Mw 720.66 g/mol) was purchased from Thermo Fisher Scientific and received as powder, 1 mg. A 10 mM stock solution was prepared by adding 139 µl DMSO to the powder. The stock solution was stored at −20° C. Alexa 488 maleimide solution must be added to the Cas9 solution such that the final concentration of DMSO is no higher than 10%, to avoid precipitation of the protein. For 12.5 µM Cas9, 20-fold molar excess corresponded to 250 µM Alexa die which in turn corresponded to a volume of 6.25 µl of the 10 mM stock solution in 250 µl. To use all the 250 µl protein solution made up, 6.25 µl die stock were added to 250 µl Cas9 solution to generate a final volume of 256.25 µl, in which DMSO was 2.5% so well below the 10% limit which induces precipitation of the protein). For size-exclusion gel chromatography Sephadex G-25 (Sigma-Aldrich) was utilised. The elution buffer contained 250 mM KCl, 20 mM Hepes, pH 7.8.

Procedure for Labelling Cas9

A 2 mg/ml solution of Cas9 (12.5 µM) was made dissolving 0.5 mg Cas9 in 197 µl labelling buffer (20 mM Hepes pH 7.8; 250 mM KCl; 50 µl glycerol (63.1 mg); 3 µl TCEP 10 mM (10-fold molar excess)). The solution was deoxygenated with Argon. A 20 molar excess maleimide solution in DMSO was added drop-wise while pipetting up and down to stir. The mix was incubated overnight at 4° C. (Zuris et al. Nat Bitoechnol 2015 33(1): 73-80) in Ar atmosphere. Note: the KCl concentration becomes 200 mM in the final 250 µl volume, and the salt KCl and glycerol help keep Cas9 in solution. TCEP is a reducing agent frequently used in biochemistry and molecular biology applications. TCEP can keep the cysteines from forming di-sulfide bonds and unlike dithiothreitol and β-mercaptoethanol, it will not react as readily with the maleimide residues.

Figure 18:
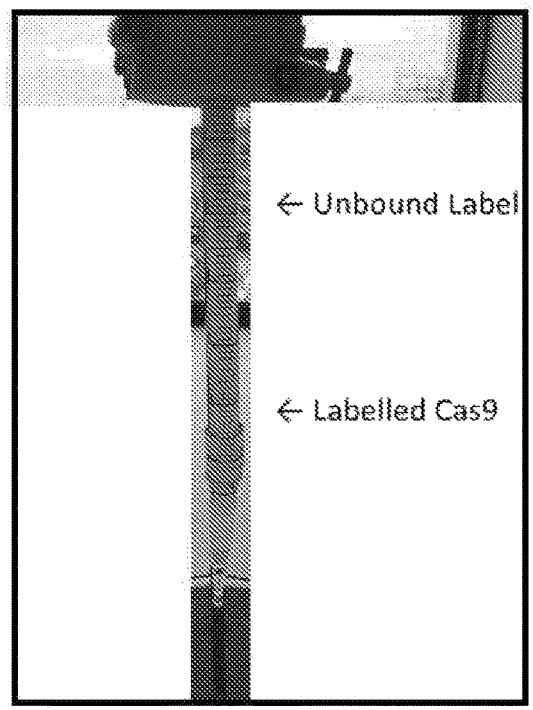
FIG. 18 is an image illustrating Cas9 purification. The larger labelled Cas9 separated from the unbound label and eluted from the column first.
Figure 19:
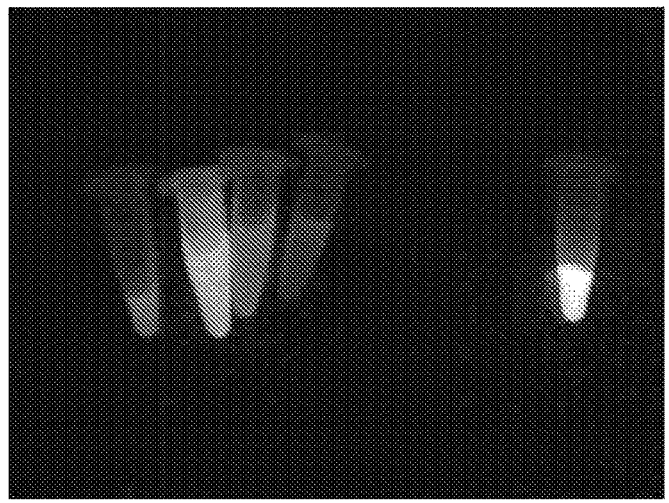
FIG. 19 is an image illustrating labelled Cas9 elutions post-separation on Sephadex column. Four aliquots were viewed on a trans-illuminator. The intensity of the second elution (from left) indicated the most concentrated and the free dye (far right) was used as reference.
Figure 20:
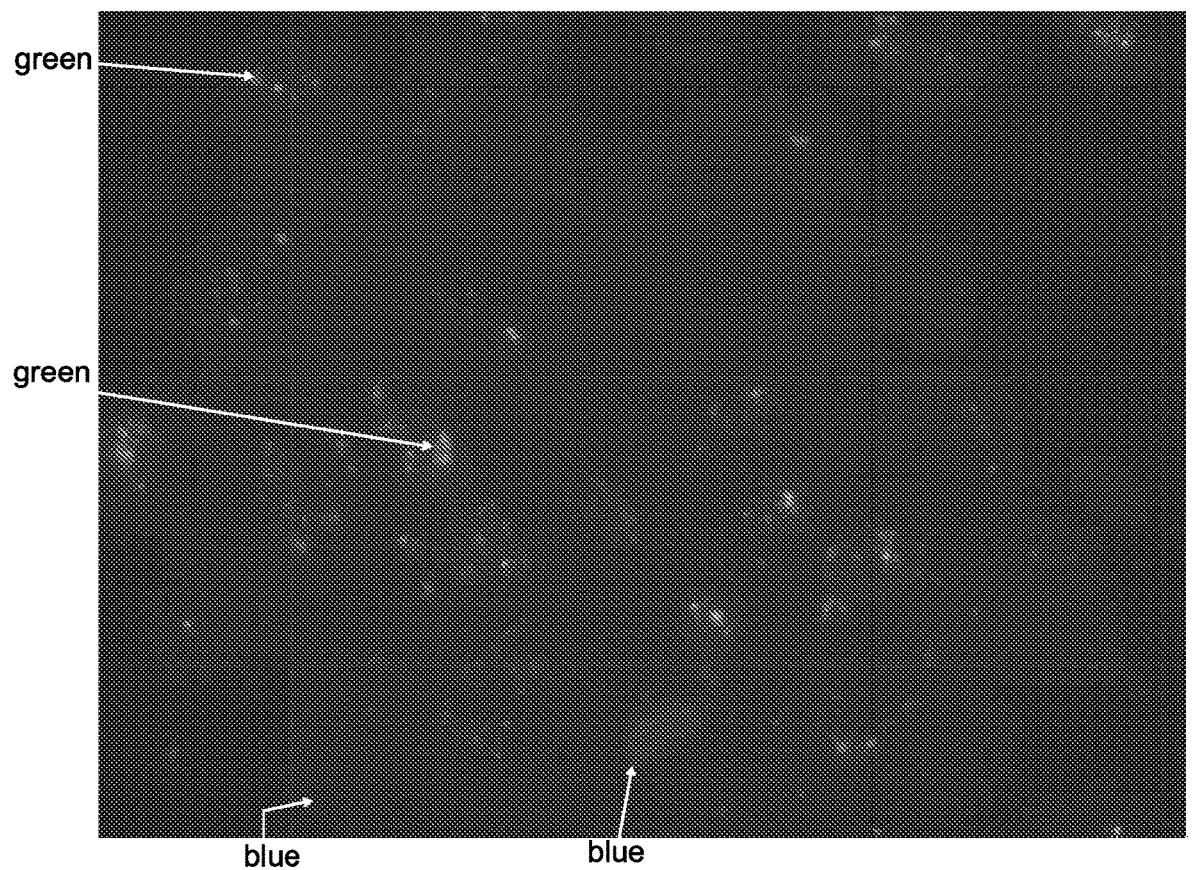
FIG. 20 is an image that represents uptake of Alexa 488 labelled Cas9 delivered to A549 cells by Delivery Platform technology (green dots). Nuclei of cells (in blue) were stained with DAPI to facilitate the visualization of cells.

The following day, after checking that no visible precipitate was present in the vial, the protein solution was loaded onto a Sephadex G25 column and eluted to purify and separate the labelled Cas9 from the free label. A faint band separated almost immediately, indicating successful labelling (FIG. 18). The eluted protein was significantly diluted. However, fluorescence was visible with the naked eye. Fluorescence was confirmed with a trans-illuminator for green fluorescence (see, FIG. 19). The Cas9 concentration after purification was evaluated with the Bicinchoninic acid assay. The more concentrated aliquot was used for RNP studies. The concentration ranged between 500-700 ng/µl, for about 1 ml volume collected.

Example 4: Approaches to Overcome Problem of Cas9 Precipitation

During the labelling process the Cas9 protein was susceptible to aggregation and precipitation. Others have also reported solubility problems with Cas9 in various solutions (Burger, A et al. 2016. *Development* 2016 143(11): 2025-37Cas9 precipitation was also observed when the protein was added to the delivery solution. Because ethanol can promote protein precipitation, it was hypothesized that one of the major factors contributing to Cas9 precipitation was the presence of ethanol in the delivery solution. The effect of increasing ethanol concentrations on Cas9 precipitation was assessed.

From the study described below, ethanol exceeding 15% induced rapid precipitation of the protein. With this information it was decided to try and increase Cas9 solubility by 1) reducing the ethanol concentration in the delivery solution, and 2) protecting the protein with an excipient/chaperone.

Effect of Ethanol Concentration on Cas9 Precipitation

A. Effect of Ethanol Concentration in Delivery Solution on Precipitation of Cas9

Figure 21:
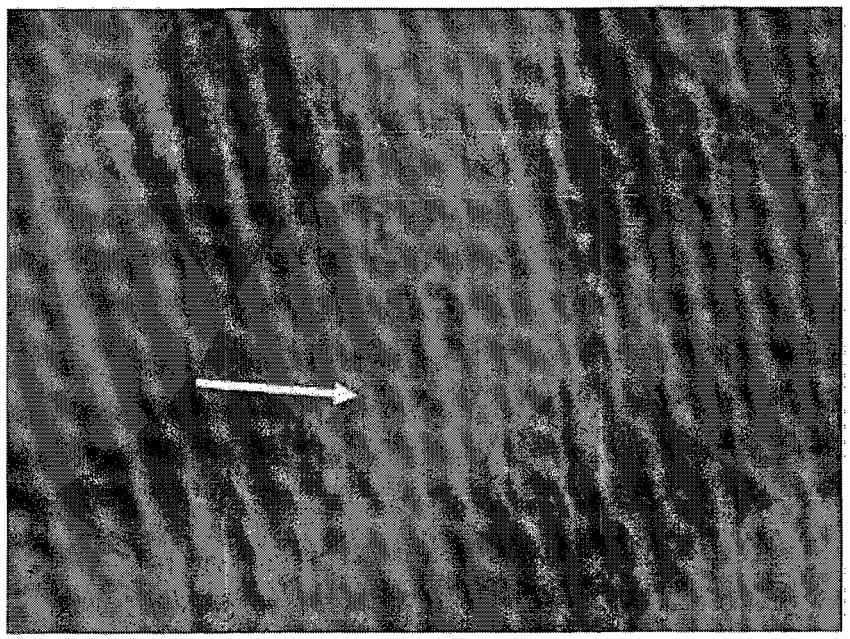
FIG. 21 is an image depicting un-labelled Cas9 500 ng/µl in delivery solution (0.5 µl Cas9 10 µg/µl, 2.5 µl S-buffer, 2.5

The labelled Cas9 was observed under the fluorescence microscope and the solution showed a green hue with little green "speckles". Those speckles grew greatly in size and number when the delivery solution (25% ethanol) was added to the Cas9. To ensure that the precipitation was not caused by the presence of the fluorescent probe on the protein, an unlabelled Cas9 solution in delivery solution with 25% ethanol was observed under the microscope. The picture is presented in FIG. 21 and aggregates of protein were visible. The protein aggregation and falling out of solution occurred in real-time while looking at the glass slide under the microscope.

After the preliminary step described above, solutions of Cas9 labelled with a fluorescent dye, containing increasing concentration of ethanol were prepared and analyzed under the fluorescence microscope immediately after the addition of ethanol. Alexa 488 Cas9 133 ng/µl labelled and purified in-house was added to the S buffer and water as listed in Table 8. The ethanol was added to the test tube just before the microscopy analysis of that sample.

Immediately after ethanol addition, 5 µl of solution was transferred to a glass slide and observed under the fluorescent microscope. Initially, samples 1-6 were investigated and results are shown in FIG. 22. After a first evaluation of results, samples 7, 8 and 9 were added (FIG. 23). Due to the low concentration of Alexa 488 Cas9, the maximum amount that could be delivered in 10 µl was 931 ng which is about 5 times less to what normally delivered (5 µg) for an edit experiment.

TABLE 8

Cas9 and ethanol volumes per 10 µl reaction

| Sample Number | % Ethanol | Alexa 488 Cas9 133 ng/µl (µl) | S-buffer * (µl) | Ethanol (µl) | RNase free water (µl) | Total volume (µl) |
|---|---|---|---|---|---|---|
| 1 | 1% | 7 | 1X, 2.5 | 0.1 | 0.4 | 10 |
| 2 | 5% | 7 | 1X, 2.5 | 0.5 | — | 10 |
| 7 | 8% | 7 | 10X, 0.25 | 0.8 | 1.95 | 10 |
| 3 | 10% | 7 | 10X, 0.25 | 1.0 | 1.75 | 10 |

TABLE 8-continued

Cas9 and ethanol volumes per 10 µl reaction

| Sample Number | % Ethanol | Alexa 488 Cas9 133 ng/µl (µl) | S-buffer * (µl) | Ethanol (µl) | RNase free water (µl) | Total volume (µl) |
|---|---|---|---|---|---|---|
| 8 | 12% | 7 | 10X, 0.25 | 1.2 | 1.55 | 10 |
| 9 | 14% | 7 | 10X, 0.25 | 1.4 | 1.35 | 10 |
| 4 | 15% | 7 | 10X, 0.25 | 1.5 | 1.25 | 10 |
| 5 | 20% | 7 | 10X, 0.25 | 2.0 | 0.75 | 10 |
| 6 | 25% | 7 | 10X, 0.25 | 2.5 | 0.25 | 10 |

* 1X S-buffer: 130 mM sucrose, 50 mM KCl, 50 mM ammonium acetate, 20 mM Hepes, pH 7.4; 10X S-buffer: 1.3M sucrose, 0.5M KCl, 0.5M ammonium acetate, 200 mM Hepes, pH 7.4

It is clear from FIG. 22 that aggregation appeared in the sample with 15% ethanol and the phenomenon becomes significant at 20 and 25%. No observable aggregation was observed for 1, 5 and 10% ethanol. For comparison, Cas9 with no ethanol and protein as eluted from the column are reported in FIG. 24.

As ethanol content below 10% results in poor uptake of the payload into cells, and an ethanol content greater than 15% results in significant precipitation of the protein, a closer investigation in the range between 10% and 15% ethanol was carried out, FIG. 23. When ethanol reached 12%, aggregation was seen at the edges of the droplet on the glass slide, indicating 10% ethanol was the best compromise for promoting uptake of payload and avoiding precipitation of the protein.

Finally, it was important to highlight that over time (1-2 h), protein aggregation was observed in all samples (except for 1% ethanol which was further examined after 2 h). These observations indicated that the Cas9 and ethanol containing solution must be used within a few minutes from preparation.

Of note, the concentration of Cas9 was lower than the concentration normally used for edit experiment because the solubility tests were carried out with Alexa 488 Cas9 made from commercially available Cas9. The labelled protein, once purified undergoes a significant dilution. The delivery solution for these assays was intended to maintain a proportion of 25% ethanol and 25% S-buffer in the 10 µl volume used for a single delivery, which meant the volume available for the addition of Cas9 was up to 5 µl. As the labelled protein was more diluted than the parent protein it was difficult to deliver 5 µg in the 5 µl volume available.

The most suitable ethanol content for the delivery solution was 10%. With such content, permeabilization of the cell membrane was still possible, and precipitation of Cas9 was avoided if the solutions were prepared and used within a few minutes. However, a reduction in delivery efficiency of large payloads such as mRNA occurred with ethanol concentrations less than 25%, and therefore the preference was to maintain the 25% ethanol concentration and to either avoid or reduce Cas9 precipitation.

B. Effect of Ethanol Concentration in Delivery Solution and Cas9 Concentration on In Vitro Edit Efficiency In vitro edit tests were carried out to evaluate the effect of Cas9 precipitation on edit efficiency of the gene editing tool. Several solutions with different amounts of Cas9 were made up for different ethanol content, as summarized in Table 9. The RNP complexes were made up by adding all reagents (Cas9 and gRNA) and components of the delivery solution (S-buffer, MGW), except for the ethanol. Ethanol was added after 10 min incubation and prior to spraying. The ratio Cas9/gRNA was 1:1 molar ratio. Cas9 was added to gRNA (384b, 5.3 µM, 223.7 ng/µl stock) in a 1:1 molar ratio and incubated for 15 min, then S-buffer and MGW were added and the mixture was incubated for 10 min. Ethanol was added last, immediately before spraying.

TABLE 9

Cas9 concentration for RNP complexes made up in delivery solution containing different amounts of ethanol

| Sample number | Cas9 concentration | % Ethanol |
|---|---|---|
| 1 | 250 ng/µl | 20 |
| 2 | 250 ng/µl | 10 |
| 3 | 250 ng/µl | 5 |
| 4 | 100 ng/µl | 20 |
| 5 | 100 ng/µl | 10 |
| 6 | 100 ng/µl | 5 |
| 7 | 50 ng/µl | 20 |
| 8 | 50 ng/µl | 10 |
| 9 | 50 ng/µl | 5 |

Immediately after the ethanol addition, 10 µl of solution was sprayed into an empty well of a 48 well plate. Then 2 µl of the sprayed solution were transferred into a test tube suitable for thermocycler and used for IVE test, as reported in Table 10, to assess the functionality of the complex. The components kept in ice were added in reaction tubes suitable for a thermocycler, also kept in ice. Then the tubes were transferred into a thermocycler pre-warmed at 30° C. The following program was run:

30 min at 30° C.
15 min at 65° C.
Hold at 4° C.

Digested samples were then analyzed by gel electrophoresis, using 1.5% gel.

TABLE 10

Component volumes per reaction for IVE of the Cas9/gRNA complex

| Component | Volume (µl) |
|---|---|
| Cas9/gRNA 1:1 sprayed | 2 |
| Target DNA (136 ng/µl) | 2 |
| 10X Cas9 Agilent buffer | 2 |
| RNase free water | 14 |
| Total | 20 |

As shown in FIG. 25, all DNA targets were edited to some extent. Samples 1-5 showed no differences, suggesting the amount of Cas9 protein used is in large excess with respect to what required for editing hence despite precipitation, the residual Cas9 in solution is sufficient to edit the target. The ethanol effect became evident only at the lowest Cas9 concentration. In sample 7 (50 ng/µl Cas9, 20% ethanol), the edited bands were weak and the uncut DNA signal was more intense. This indicated that ethanol-induced precipitation of Cas9 at the lowest concentration (and highest ethanol) deprived the system of functional Cas9 available for editing. At the higher concentrations, the protein remaining in solution was probably enough to cut the target DNA.

C. Use of Excipients to Prevent Precipitation of Cas9 i) Effect of High Salt Concentrations on Cas9 Precipitation

Cas9 requires a relatively high salt concentration to stay in solution and concentrations about 200-250 mM KCl are used in the most important publications. In the attempt to prevent precipitation occurring after ethanol addition, Cas9 or RNP solutions were made up in delivery solution where water was replaced with either 0.5 M KCl or 1 M KCl. As previously stated all components except ethanol were added, then the solution was incubated for 15 min at RT and finally ethanol was added. In all cases substantial precipitation of protein or complex was observed.

ii) Effect of Glycerol on Cas9 Precipitation

Glycerol is known to improve protein solubility. In this experiment 5, 20 or 20% glycerol was added to the recipe of the delivery solution. Again the ethanol was added to the rest of the components after 15 min incubation at RT. In the samples containing Cas9 only the addition of ethanol still led to precipitation but without the formation of big aggregates. To the contrary, no precipitation was observed for the RNP in delivery solution with 20% glycerol even after the addition of ethanol (FIG. 25). For the RNP in delivery solution with 5% and 10% glycerol it was hard to establish whether or not precipitate formed as the particles seen looked like background dirt present on some glass slide. Certainly, the typical big clusters of protein did not appear (FIGS. 26A-26C). However, when glycerol-containing solutions were sprayed onto cells, cell damage was observed. Therefore, glycerol was not a suitable excipient to use in this context.

iii) Effect of NDSB-201 (Non-Detergent Sulfobetaine, Zwitterionic Compound) on Cas9 Precipitation NDSB-201 is known to improve protein solubility. Cas9 alone or with RNP were made up in delivery solution containing 0.05 (D'Astolfo D S et al., *Cell* 161(3): 674-90), 0.2 and 0.5 M NDSB. Again, all components but ethanol were added together, solutions were incubated for 15 min, and then ethanol was added. When the ethanol was added, precipitate formed for all samples containing Cas9 only. No precipitation was seen for RNP (ribonucleoprotein, the complex of Cas9 with the guide RNA) with 0.5 M NDSB (FIGS. 26A-26C). For RNP with 0.05 and 0.2 M NDSB either little precipitate or no precipitate (hard to tell because of background noise) was observed.

iv) Effect of Other Excipients on Cas9 Precipitation

Taking into account the above results, a series of experiments were designated that assessed the ability of known protectants/chaperones/excipients to "protect" the Cas9 protein from ethanol-induced precipitation. Heat shock proteins (HSPs) are essential for the correct folding and maturation of a great diversity of client proteins and for protecting proteins from stress-induced unfolding and aggregation (Morimoto, R. I., 2008: *Genes & Development*, v. 22, p. 1427-1438; Richter, K et al. 2010: *Mol Cell*, v. 40, p. 253-266). Small HSPs (sHSP) are the major "holding" chaperones, retaining unfolding proteins in a conformation suitable for subsequent refolding, thus preventing their irreversible aggregation (Eyles, S. J., and L. M. Gierasch, 2010: *PNAS*, v. 107, p. 2727-2728; Stengel, F et al, 2010: *PNAS*, v. 107, p. 2007-2012). α-crystallin is an important member of the small heat shock protein family and a vital structural component of the lens (Reddy, et al 2006: *Iubmb Life*, v. 58, p. 632-641).

The following stock concentrations of components were used: Cas9 (10 µg/µl) (IDT, 1074182), Cas9 digestion buffer (Sureguide kit, Agilent), gRNA (21.8 µM) for HPRT (IDT), D-sorbitol (Sigma, S3889), D-mannitol (Sigma, M4125), α-crystallin from bovine eye lens (Sigma, C4163), NDSB (Sigma, 82804), Gelatin A (Sigma, G1890), Gelatin B (Sigma, G9391), Glycine (Sigma, G7126), Proline (Sigma, P5607), Tween-20 (Sigma, P9416), L-histidine (Sigma, H8000), myo-inositol (Sigma, 15125), and Trehalose (Sigma, 90210).

Selection of additives was decided based on the current literature on stabilizing proteins and prevention of aggregation. The final list of additives that were selected is shown in Table 11. The additives were tested to see if they could preserve Cas-9 nuclease function in the presence of ethanol. The stock Cas9 was diluted in nuclease free $H_2O$ to obtain a 1 µg/µl solution. The Cas9 and sgRNA were added in a molar ratio of 1:3. They were then incubated for 10 mins at RT to allow the Cas9:sgRNA ribonucleoprotein (RNP) to form. The additives were added to the concentration shown in Table 12. The ethanol was added last and the solutions were incubated at room temperature for 2 min. The solutions were then added directly to the in vitro edit reaction as outlined in Table 13. The samples were mixed and incubated on a thermocycler with the following program according to manufacturer's specifications: 30 min. at 30° C., 15 min at 65° C., Hold at 4° C. The samples were placed on ice and 4 µl of 6× loading dye (NEB, reducing) was added. The samples were loaded on a 2% agarose gel stained with Sybrsafe according to the manufacturer's instructions and run at 100 V for 1 h.

Using the Genetools program (Syngene) the editing efficiency of Cas9:gRNA was measured after exposure to different delivery solutions with or without additives. The intensity of band 2 (edited HPRT) relative to band 1 was obtained and expressed as a percentage. All values were normalized to the sample containing no ethanol.

To test the effect these protectants had on gene editing intracellularly, Cas9 RNP was delivered to cells, with some of the above protectants, by Delivery Platform technology. Bone marrow-derived Mesenchymal Stem Cells (MSCs) were seeded in a 96-well plate at a density of $9 \times 10^3$ cells per well and cultured overnight at 37° C. The following morning 5 µg of Cas9 and guide RNA (HPRT; 1:6 ratio) were complexed and added to delivery S Buffer, with α-crystallin (220 µM), NDSB (0.5M) or Sorbitol instead of sucrose (final 4%). Ethanol (25% v/v) then added and delivered to the cells by way of a spray. 4 hr later the process was repeated and the cells were then cultured for 72 hr prior to edit analysis by droplet digital PCR.

TABLE 11

Additives used in this study

| Category | Chemical | Stock concentration | Working concentratin | Publications |
|---|---|---|---|---|
| Zwitterionic | NDSB | 2M | 0.2M | D'Amico, S., and G. Feller, 2009: *Anall Biochem*, v. 385, p. 389-391 (2009). |
| Non-ionic detergent | Tween-20 | 0.5% v/v | 0.1% v/v | Kerwin, B. A., 2008: *J of Pharm Sciences*, v. 97, p. 2924-2935. |
| Sugar | Trehalose | 264 mM | 26.4 mM | Liu, R., H. et al, 2005: *Neurobiology of Disease*, v. 20, p. 74-81. |

TABLE 11-continued

Additives used in this study

| Category | Chemical | Stock concentration | Working concentratin | Publications |
|---|---|---|---|---|
| Alcohol sugar | myo-inositol | 5% w/v | 1% w/v | Ohta, E., et al. 2016: *J of Bioscience and Bioengineering*, v. 121, p. 399-405. |
| | D-sorbitol | 20% w/v | 4% w/v | Xie, G. F., and S. N. Timasheff, 1997: *Protein Science*, v. 6, p. 211-221. |
| | D-mannitol | 10% w/v | 2% w/v | Han, Y. et al, 2007: *Archives of Pharmacal Research*, v. 30, p. 1124-1131. |
| Heat shock protein | Alpha crystallin | 1 mM | 100/220 µM | Ferns, J. E., et al., 2012: *Neurochemical Research*, v. 37, p. 244-252. |
| Peptides | Gelatin, Type A | 5% w/v | 1% w/v | Young, S., M. et al, 2005: *J of Controlled Release*, v. 109, p. 256-274. |
| | Gelatin, Type B | 5% w/v | 1% w/v | Young, S., M. et al, 2005: *J of Controlled Release*, v. 109, p. 256-274. |
| Amino acids | Glycine | 1.25M | 0.25M | Platts, L., and R. J. Falconer, 2015: *Intl Journal of Pharmaceutics*, v. 486, p. 131-135. |
| | L-arginine | 250 mM | 50 mM | Platts, L., and R. J. Falconer, 2015: *Intl Journal of Pharmaceutics*, v. 486, p. 131-135. |
| | Proline | 375 mM | 75 mM | Samuel, D. et al. 2000: *Protein Science*, v. 9, p. 344-352. |
| | Histidine | 64 mM | 12.8 mM | Chen, B., et al. *Pharm Res*, v. 20, p. 1952-1960. |

TABLE 12

Components of in vitro edit reaction. Final concentration of Cas9 was 75 ng/µl

| Component | Volume |
|---|---|
| Cas-9 (1 µg/µl) | 1.5 µl |
| HPRT single guide RNA | 1.29 µl |
| S. buffer | 2.5 µl |
| Ethanol | 2.5 µl |
| Additive | Variable |
| $H_2O$ | Make up to 10 µl |

TABLE 13

Components of in vitro edit reaction. Final concentration of Cas9 was 75 ng/µl

| Component | Volume |
|---|---|
| Delivery solution | 1 µl |
| HPRT DNA (15 ng/µl, qiaquick purified after PCR) | 4 µl |
| 10x Cas9 digestion buffer (Sureguide kit, Agilent) | 2 µl |
| $H_2O$ | 13 µl |
| Total | 20 µl |

The in vitro edit experiments showed that additives can preserve Cas9 nuclease function in the presence of ethanol (FIG. 28 and FIGS. 19A-29B). The addition of α-crystallin and sorbitol in particular improved the nuclease activity of Cas-9:gRNA after exposure to delivery solution. The in vitro edit efficiency of Cas-9:gRNA improved on average from 49%, in the no additive control, to 98% and 103% efficiency in the sorbitol and α-crystallin samples respectively. α-crystallin and NDSB were added to the delivery solution to improve the CRISPR-Cas9 edit of hprt in MSCs (FIG. 30). The addition of α-crystallin to a final concentration of 220 µM increased the hprt edit from 11.09% (no additive control) to 16.34%. The addition of NDSB to the delivery solution had no effect on the hprt edit of MSCs. α-crystallin is also a more superior additive than sorbitol in maximising the edit of hprt in U2OS cells (FIG. 31).

Ethanol is known to displace water at protein sites which alters the structure of proteins (Dwyer, 1999 *Biopolymers* 49(7): 635-45). This could result in exposure of the hydrophobic core which can lead to protein aggregation. Recently, a study by Ferns, et al., (Ferns, 2012: *Neurochemical Research*, v. 37, p. 244-252) found that ethanol induced aggregation of GAPDH was prevented α-crystallin. Therefore, α-crystallin may be preventing aggregation of Cas-9.

Example 5: Optimization of Delivery Protocol to Achieve Higher Edit Efficiencies The ability of the Delivery Platform technology to affect an edit in adherent cells was influenced by the size of the target cell monolayer, the concentration of Cas9, the ratio of protein to guide RNA and the number of times the cells are processed by the technology. There may be an optimal ratio of Cas9 protein to guide RNA and that it may be both cell- and gene target-specific Materials used included: U2OS cells (Osteosarcoma cell line—ECACC), Bone-Marrow-derived Mesenchymal Stem Cells (MSCs; Lonza), Jurkat E6.1 cells (T cell line—ECACC), DMEM Low glucose (Sigma-Aldrich), FBS (Sigma), RPMI-1640 (Life Technologies), Trypsin/EDTA (Gibco), Cas9 nuclease (IDT-DNA), crRNA (IDT-DNA), trRNA (IDT-DNA), delivery S Buffer, α-crystallin (Sigma), Ethanol, Hex-labelled Drop Off probe (IDT-DNA), FAM-labelled Reference probe (IDT-DNA), and ddPCR Supermix (BioRad).

Cell Culture

U2OS cells were seeded at $5 \times 10^4$ for 24 well plates, $3 \times 10^4$ for 48 well plates and $1 \times 10^4$ for 96 well plates and cultured overnight at 37° C. The following morning 5 µg of Cas9 (HPRT guide; 1:3 ratio) was added to delivery S Buffer, with α-crystallin (220 μM) and ethanol (25% v/v) also added. This was then delivered to the cells in the form of a spray. The cells were allowed to recover for 4 hr before being sprayed again with the same payload. The cells were then cultured for 72 hr before harvest and analysis. In another set of experiments, Bone marrow-derived Mesenchymal Stem Cells (MSCs) were seeded in a 96-well plate at a density of $9 \times 10^3$ cells per well and cultured overnight at 37° C. The following morning 5 rig of Cas9 was added to delivery S Buffer, with α-crystallin (220 μM) and ethanol (25% v/v) also added.

In the first experiment, the effect of $MgCl_2$ addition was assessed. Cas9 RNP (5 rig; HPRT target 1:6) was delivered to MSC cells with or without 2.5 mM MgCl2. The cells were allowed to recover for 4 hr before the process was repeated and then they were cultured for 72 hr prior to edit analysis. In the next experiment, different amounts of guide were also added (crRNA:trRNA was 1:1 molar ratio) so that 1:1, 1:3 and 1:6 molar ratios of protein to guide RNA was achieved in a final volume of 10 μl. The guide used in these experiments was targeting a site within the HPRT gene and the sequence taken from the literature (Liang et al., 2015 *J Biotechnol* 208L44-53). The media was removed from the cells and the payload in delivery solution was added to the spray nozzle. The cells were sprayed and incubated for 2 minutes before the addition of 150 μl of 0.5×PBS (stop solution). They were further incubated for 30 seconds before the stop solution was removed and 150 μl normal media was added. The cells were cultured for 72 hr before being harvested for edit analysis.

In a second experiment, the amount of Cas9 was varied from 0.1 μg to 24 μg at a ratio of 1:1 protein to guide. The payload was delivered and the cells treated as described above. In a third experiment, the cells were processed repeatedly. 5 μg Cas9 at a guide ratio of 1:6 was delivered to the cells as described above. The cells were then trypsinized and reseeded into the same wells before being cultured overnight. The following morning the cells were processed again under the same conditions. The cells were left in media for 4 hr before they were processed for a third time under the same conditions. The cells were again cultured overnight. The following morning the cells were processed for a fourth time under the same conditions and left for 4 hr before being trypsinized and seeded into a well of a 48 well plate and cultured for 72 hr. The cells were then harvested and prepared for gene edit analysis by droplet digital PCR and drop off assay.

Edit Analysis

The presence of an edit was analyzed using Droplet Digital PCR (ddPCR) which is a method for performing digital PCR that is based on water-oil emulsion droplet technology. A sample was fractionated into 20,000 droplets, and PCR amplification of the template molecules occurred in each individual droplet. In this method the technology was used to detect the presence of an edit in the HPRT gene due to Cas9 RNP action on the genome. This assay was set up specifically to deal with non-homologous end joining repair of a double stranded cut in the DNA. Forward and reverse primers generated an amplicon of ~150 bp. Two internal probes were used; one which serves as a reference probe and should bind to all amplified DNA strands and a second which sits over the Cas9 cleavage site and is bound when no edit has taken place but cannot bind when an edit has been affected In this experiment the DNA was extracted from samples using the MagNA Pure compact system. ddPCR components were prepared as per manufacturers guidelines. Components were transferred to DG8 cartridges and droplets were generated with a QX200 Droplet generator. Droplets were then transferred into a 96-well PCR plate and sealed. PCR was performed and the droplets were analyzed using QX200 Droplet Reader.

i) Effect of Size of Cell Monolayer on Edit Efficiency

Edit efficiency increased when the diameter of the cell monolayer was decreased by seeding cells in smaller wells, thereby better matching the diameter of the monolayer with the diameter of the spray (FIG. 32).

U2OS cells were seeded in either 24-, 48-, or 96-well plates and cultured overnight. The following day, two doses of Cas9 RNP (5 μg; 1:6 ratio HPRT gRNA) was delivered by Delivery Platform technology and cells were cultured for a further 72 hr before harvesting. Edit efficiency was analyzed by ddPCR and indicated that cells that were seeded in the smallest wells produced the greatest edit efficiency ii) Effect of Increasing Cas9 Concentrations on Edit Efficiency The percentage edit that is achieved by delivering Cas9 at ratio of 1:1 with the guide RNA increased with increasing concentrations of Cas9, plateauing at about 5 μg Cas9 (FIG. 33).

MSCs were seeded into 96-well plates and cultured overnight. The following day different concentration of Cas9 RNP (0.1, 0.5, 1.0, 5.0, 10.0, 15.0, 24.0 μg) with the HPRT guide RNA at 1:1 molar ratio was delivered by Delivery Platform technology and cells were cultured for a further 72 hr before harvesting. Edit efficiency was analyzed by ddPCR and indicated that edit efficiency increased with increasing amounts of Cas9 protein with the increase plateauing at about 5 μg Cas9.

iii) Effect of Cas9:gRNA Ratio on Edit Efficiency

Delivering 5 ug of Cas9 along with the guide RNA at different ratios (1:1, 1:3 or 1:6) did not alter the efficiency of edit in the MSC cells (FIG. 34).

MSCs were seeded into 96-well plates and cultured overnight. The following day Cas9 RNP (5 μg) with the HPRT guide RNA at either 1:1, 1:3 or 1:6 molar ratios were delivered by Delivery Platform technology and cells were cultured for a further 72 hr before harvesting. Edit efficiency was analyzed by ddPCR and indicated that, with these cells and this particular target and guide RNA, there was no difference in editing efficiency with the ratios of protein: guide RNA tested iv) Effect of Number of RNP Doses Delivered on Edit Efficiency Increasing the number of times that the cells go through the delivery process (Cas9-5 μg, ratio-1:6) increased the percentage edit detected in the HPRT gene (FIG. 35). MSCs were seeded into 96-well plates and cultured overnight. Over the next 3 days, either 1, 2, 3 or 4 doses of Cas9 RNP (5 μg; 1:6 ratio HPRT gRNA) were delivered by Delivery Platform technology and cells were cultured for a further 72 hr, after the last dose delivered, before harvesting. Edit efficiency was analysed by ddPCR and indicated that the edit efficiency increased with number of doses of Cas9 RNP received by the cells. *$p<0.05$, Students' t test for independent means.

As evident herein, the platform delivery technology can deliver a range of molecules to cells while maintaining their viability and functionality. This attribute allows a regimen of multiple dosing of the same molecule or, potentially, different molecules at different time points (FIG. 35). This is unlike electroporation, where multiple dosing cannot be achieved due to the detrimental effect on the cells resulting in much reduced viability. The potential exits therefore, to deliver the plasmid form of Cas9, allow a period of time for the protein to be expressed by the cell and then deliver the guide RNA which, when combined, would affect the edit.

v) Effect of $MgCl_2$ on Edit Efficiency

Based on previous in vitro edit studies it was observed that $MgCl_2$ addition was necessary to affect an edit. In this study the effect of adding to cells alongside the Cas9 RNP was assessed. It demonstrated that $MgCl_2$ addition did not improve the edit efficiency and subsequent studies did not include $MgCl_2$ addition (FIG. 25). MSC cells were seeded in 96-well plates and Cas9 RNP (5 ug; HPRT 1:6 ratio) was delivered by Delivery Platform technology in the presence or absence of $MgCl_2$ (2.5 mM)

Example 6: Comparison with Electroporation

A comparison with the industry standard for protein delivery, electroporation, was assessed for delivery efficiency, viability and functionality.

A. Comparison of Edit Efficiencies: Delivery Platform Versus Electroporation

Edit efficiency was greater in MSCs where Cas9 was delivered by delivery technology provided herein compared with Electroporation (FIG. 37).

MSCs were seeded into 96-well plates and cultured overnight. Over the next 3 days, 4 doses of Cas9 RNP (5 μg; 1:6 ratio HPRT gRNA) were delivered by Delivery Platform technology and cells were cultured for a further 72 hr, after the last dose delivered, before harvesting. For the electroporation comparison, MSCs were prepared in buffer and treated as per manufacturer's instructions. The same amount of Cas9 and guide were delivered as per Delivery Platform treated cells. Cells were harvested and edit efficiency was analyzed by ddPCR. Successful edit was observed in when Cas9 was delivered by either methods, however, the efficiency was significantly greater in cells where the Cas9 RNP was delivered by Delivery Platform technology. *$p<0.05$, Students' t test for independent means.

B. Comparison of Cell Viability Following RNP Delivery: Delivery Platform Versus Electroporation Cell viability was comparable between cells that had been edited by Cas9 RNP delivered by either Delivery Platform technology or electroporation (FIG. 38). 24 hr post-delivery of the final dose of Cas9 RNP, cells were analyzed for viability by EBAO counts. No significant difference was observed in viability between these 2 groups.

C. Comparison of Cell Functionality Following RNP Delivery: Delivery Platform Versus Electroporation The functionality of MSCs is unaffected by Delivery Platform technology (FIG. 39). Three representative images of differentiated MSC from an untreated group (Untreated), a Cas9 RNP delivered by the Delivery Platform technology group (Delivery Platform), and a Cas9 RNP delivered by Electroporation group (Electroporation) were tested. One day post-delivery of Cas9 RNP (5 rig; 1:6 ratio HPRT gRNA) cells were seeded at $1 \times 10^5$ into a 6 well plate in culture medium and cultured for 5 days or until cells are 90-100% confluent. The media was then removed and 2 ml adipogenic differentiation media was added to the cells. Media was changed every 3 days until differentiation is observed (usually 2-3 weeks). Oil droplets can be observed (white) within in the cells, indicating differentiation. There was no difference between untreated and Delivery Platform-treated cells. However, differentiation appeared to be inhibited in cells that were treated by electroporation. Both adherent and suspension cells, and primary and cell lines, were assessed for edit post-delivery of Cas9 RNP by Delivery Platform technology.

Example 7: Edit Efficiency in Adherent and Suspension, Cell Lines and Primary Cells MSC and U2OS cells were seeded into 96-well plates and cultured overnight. Over the next 3 days, 4 doses of Cas9 RNP (5 rig; 1:6 ratio HPRT gRNA) were delivered by Delivery Platform technology and cells were cultured for a further 72 hr. For the suspension cells, $1.5 \times 10^6$ isolated human CD3+ T cells or Jurkat cells were seeded into a 96-well filter plate (1.2 rim). Cas9 RNP (5 rig; 1:6 ratio CXCR4 gRNA) was delivered by Delivery Platform technology and cells were cultured for a further 72 hr. Cells were harvested and edit efficiency was analyzed by ddPCR. Successful edit was observed in both cell lines and primary human cells (FIG. 40)

Example 8: Edit Efficiency Using Cas9 mRNA

The ability to affect an edit in cells post-delivery of Cas9 mRNA was assessed. Gene edit was detected in cells where Cas9 mRNA and guide RNA were delivered in the same payload (FIG. 41). MSCs were seeded into 96-well plates and cultured overnight. The next day Cas9 mRNA (4 μg) and guide RNA (equivalent to 1:6 ratio; HPRT gRNA) were delivered by delivery technology and cells were cultured for a further 72 hr before harvesting. Edit efficiency was analyzed by ddPCR and edit was detected in these cells.

Vector-Free Delivery of Gene Editing Proteins to Cells and Tissues

The Crispr Cas9 system has rapidly become prominent in the field of genome editing. Crispr Cas9 recognizes a specific sequence in the genome with the aid of a guide RNA and induces a double-stranded cut in the DNA. The cell can repair this cut with the error prone non-homologous end-joining process, thus editing the gene. The ability of Delivery Platform technologies provided herein to deliver gene editing tools to cells in order to affect an edit was assessed.

In order to assess whether the tools (recombinant Cas9 protein and commercially available guide RNAs) induced a cut in a DNA target, an in vitro edit assay was established based on the Agilent SureGuide Cas9 Programmable Nuclease Kit. The effect of Delivery Platform delivery solution on the function of Cas9 and the guide RNAs was also assessed using this non-limiting assay. It was found that the ability of Cas9 to affect an edit was not abolished by an exemplary delivery solution. Furthermore, when the Cas9 protein was added to the delivery solution, sprayed into a well, collected and then functionally assessed in the in vitro edit test in order to replicate the full delivery process, Cas9 activity was preserved. To confirm Cas9 uptake into target cells following delivery, the Cas9 protein was labelled with the fluorescent tag Alexa-488 maleimide through the thiol groups of cysteine amino acids (2 cysteine residues per molecule of protein). The successful labelling of the protein allowed the visualization of the protein intracellularly.

Cas9 is a bacterial protein that does not occur naturally in mammalian cells. Cas9 has a tendency to precipitate out of solution under certain conditions and this would affect its function. For most cells types, optimal delivery of cargos into cells using the Delivery Platform delivery technology is achieved with ethanol concentrations of up to 25% (v/v) and it was observed that Cas9 is prone to precipitation when in contact with levels of ethanol above 15%. In order reduce Cas9 ethanol-induced precipitation, a range of excipients were assessed using the in vitro edit assay and following deliver to cells. While some excipients such as glycerol and non-detergent sulfobetaine (NDSB) prevented ethanol-induced precipitation, these excipients caused some cell damage when included in spray delivery experiments. However, the addition of the heat shock protein, α-crystallin, to the delivery solution appeared to promote the editing ability of Cas9 in the in vitro edit assay and was also compatible with delivery to cells. When the Cas9 RNP was delivered to cells in the presence of α-crystallin, effective genome editing of cells was detected by droplet digital PCR. The addition of this excipient to the delivery solution enabled the subsequent optimization of protocols for Delivery Platform technology-mediated Cas9 RNP genome editing in both adherent and suspension cells, and in primary cells as well as cell lines. As an example, this optimization has yielded gene edit in 50% primary human MSC. Furthermore, it has been demonstrated that the level of Delivery Platform technology-mediated editing in MSC is greater than that achieved by electroporation and that viability and functionality of edited MSC is superior with the delivery technology provided herein compared with electroporation Other Embodiments All United States patents and published or unpublished United States patent applications cited herein are incorporated by reference. All published foreign patents and patent applications cited herein are hereby incorporated by reference. All other published references, documents, manuscripts, accession numbers, and scientific literature cited herein are hereby incorporated by reference.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method for delivering a gene editing composition across a plasma membrane of a cell, comprising:
providing a population of mesenchymal stem cells (MSCs), U2OS, Jurkat or T cells; and
contacting the population of cells with a volume of a hypotonic aqueous solution, the hypotonic aqueous solution comprising the gene editing composition, ethanol at a concentration of about 25% (v/v), about 32 mM sucrose, about 12 mM potassium chloride, about 12 mM ammonium acetate, about 5 mM 4-(2-hydroxyethyl)-1-piperazineethanesulfonic acid (HEPES), and about 2.5 mM MgCl$_2$,
wherein the volume is a function of: (i) exposed surface area of the population of cells; or (ii) a number of cells in the population of cells;
wherein the gene editing composition includes a Cas9 protein and a gRNA complex;
wherein contacting the population of cells with the volume of the hypotonic aqueous solution is performed by gas propelling the hypotonic aqueous solution to form a spray.

2. The method of claim 1, wherein the gene editing composition is detectable in said population of cells, or the progeny thereof, for
(a) about 0.5, 1, 2, 3, 4, 5, 6, 7, 8, 9, 10, 12, 24, 48, 60, 72, 0.5-2, 0.5-6, 6-12 or 0.5-72 hours after the population of cells is contacted with the aqueous solution, or
(b) less than about 0.5, 1, 2, 3, 4, 5, 6, 7, 8, 9, 10, 12, 24, 48, 60, 72, 0.5-2, 0.5-6, 6-12 or 0.5-72 hours after the population of cells is contacted with the aqueous solution.

3. The method of claim 1, wherein the population of cells, or the progeny thereof:
(a) becomes genetically modified after contact with the aqueous solution; or
(b) is viable after contact with the aqueous solution.

4. The method of claim 1, wherein the gene editing composition:
(a) induces single-strand or double-strand breaks in DNA within the cells; or
(b) comprises a repair template polynucleotide.

5. The method of claim 1, wherein the gene editing composition further comprises a repair template polynucleotide, wherein the repair template comprises
(a) a first flanking region comprising nucleotides in a sequence complementary to about 40 to about 90 base pairs on one side of the single or double strand break and a second flanking region comprising nucleotides in a sequence complementary to about 40 to about 90 base pairs on the other side of the single or double strand break;
(b) a first flanking region comprising nucleotides in a sequence complementary to at least about 20, 25, 30, 35, 40, 45, 50, 60, 70, 80, or 90 base pairs on one side of the single or double strand break and a second flanking region comprising nucleotides in a sequence complementary to at least about 20, 25, 30, 35, 40, 45, 50, 60, 70, 80, or 90 base pairs on the other side of the single or double strand break.

6. The method of claim 1, wherein:
(a) the volume of aqueous solution is delivered to the population of cells in the form of a spray of aqueous particles;
(b) the volume is between $2.6 \times 10^{-9}$ microliter per square micrometer of exposed surface area and $1.1 \times 10^{-6}$ microliter per square micrometer of exposed surface area;
(c) the population of cells is in contact with said aqueous solution for 0.1-10 minutes prior to adding a second volume of buffer or culture medium to submerse or suspend said population of cells; or
(d) the volume of aqueous solution is delivered to the population of cells in the form of a spray of aqueous particles, and wherein a buffer or culture medium comprises phosphate buffered saline (PBS) is added to submerse or suspend the population of cells after said population of cells is in contact with the aqueous particles for 0.1-10 minutes.

7. The method of claim 1, wherein the volume of aqueous solution is delivered to the population of cells in the form of a spray of aqueous particles, wherein
(a) the volume of the spray of aqueous particles is between $6.0 \times 10^{-7}$ microliter per cell and $7.4 \times 10^{-4}$ microliter per cell; and/or
(b) the aqueous particles have discrete units of volume ranging in size from 10 nm to 100 µm, 30-100 µm, 50-80 µm or 30-50 µm in diameter.

8. The method of claim 1, wherein the spray comprises a colloidal or sub-particle comprising a diameter of 10 nm to 100 µm.

9. The method of claim 1, wherein said aqueous solution:
(a) further comprises an additive, wherein said additive comprises a heat shock protein or a sugar alcohol;
(b) does not comprise glycerol;
(c) further comprises an additive, wherein said additive comprises a heat shock protein or a sugar alcohol, and wherein said heat shock protein comprises α-crystallin;

(d) further comprises an additive, wherein said additive comprises a heat shock protein or a sugar alcohol, wherein said heat shock protein comprises α-crystallin, and wherein said α-crystallin is present in a concentration of about 1 to about 500 µM; or
(e) further comprises an additive, wherein said additive comprises a heat shock protein or a sugar alcohol, wherein said sugar alcohol comprises sorbitol in concentration of about 1 to about 10% weight/volume.

10. The method of claim 1, wherein the MSCs comprise bone marrow-derived MSCs.

\* \* \* \* \*

```
SEQUENCE LISTING

<160> NUMBER OF SEQ ID NOS: 30

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190
```

```
Asn Gln Leu Phe Glu Glu Asn Pro Ile Asn Ala Ser Gly Val Asp Ala
    195                 200                 205
Lys Ala Ile Leu Ser Ala Arg Leu Ser Lys Ser Arg Arg Leu Glu Asn
210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
            275                 280                 285
Leu Phe Leu Ala Ala Lys Asn Leu Ser Asp Ala Ile Leu Leu Ser Asp
            290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
            355                 360                 365
Gln Glu Glu Phe Tyr Lys Phe Ile Lys Pro Ile Leu Glu Lys Met Asp
            370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
Leu Lys Asp Asn Arg Glu Lys Ile Glu Lys Ile Leu Thr Phe Arg Ile
            435                 440                 445
Pro Tyr Tyr Val Gly Pro Leu Ala Arg Gly Asn Ser Arg Phe Ala Trp
            450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
            530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
            595                 600                 605
```

```
Asn Glu Glu Asn Glu Asp Ile Leu Glu Asp Ile Val Leu Thr Leu Thr
    610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
```

```
            1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
        1295                1300                1305

Ile Ile His Leu Phe Thr Leu Thr Asn Leu Gly Ala Pro Ala Ala
        1310                1315                1320

Phe Lys Tyr Phe Asp Thr Thr Ile Asp Arg Lys Arg Tyr Thr Ser
        1325                1330                1335

Thr Lys Glu Val Leu Asp Ala Thr Leu Ile His Gln Ser Ile Thr
        1340                1345                1350

Gly Leu Tyr Glu Thr Arg Ile Asp Leu Ser Gln Leu Gly Gly Asp
        1355                1360                1365

<210> SEQ ID NO 2
<211> LENGTH: 12
<212> TYPE: PRT
<213> ORGANISM: Artificial Sequence
<220> FEATURE:
<223> OTHER INFORMATION: synthetic construct

<400> SEQUENCE: 2

Gly Gly Ser Gly Pro Pro Lys Lys Lys Arg Lys Val
```

```
<210> SEQ ID NO 3
<211> LENGTH: 9
<212> TYPE: PRT
<213> ORGANISM: Artificial Sequence
<220> FEATURE:
<223> OTHER INFORMATION: synthetic construct

<400> SEQUENCE: 3

Tyr Pro Tyr Asp Val Pro Asp Tyr Ala
1               5

<210> SEQ ID NO 4
<211> LENGTH: 1389
<212> TYPE: PRT
<213> ORGANISM: Artificial Sequence
<220> FEATURE:
<223> OTHER INFORMATION: synthetic construct

<400> SEQUENCE: 4

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285
```

```
Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
```

```
            705                 710                 715                 720
His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125
```

```
Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Gly Gly Ser Gly Pro Pro Lys Lys Lys Arg Lys Val Tyr Pro Tyr
    1370                1375                1380

Asp Val Pro Asp Tyr Ala
    1385

<210> SEQ ID NO 5
<211> LENGTH: 7
<212> TYPE: PRT
<213> ORGANISM: Artificial Sequence
<220> FEATURE:
<223> OTHER INFORMATION: synthetic construct

<400> SEQUENCE: 5

Pro Lys Lys Lys Arg Lys Val
1               5

<210> SEQ ID NO 6
<211> LENGTH: 16
<212> TYPE: PRT
<213> ORGANISM: Artificial Sequence
<220> FEATURE:
<223> OTHER INFORMATION: synthetic construct

<400> SEQUENCE: 6

Lys Arg Pro Ala Ala Thr Lys Lys Ala Gly Gln Ala Lys Lys Lys Lys
```

-continued

```
1               5               10              15
```

<210> SEQ ID NO 7
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (3)..(12)
<223> OTHER INFORMATION: Xaa is unknown or other

<400> SEQUENCE: 7

```
Lys Arg Xaa Xaa Xaa Xaa Xaa Xaa Xaa Xaa Xaa Xaa Lys Lys Lys Lys
1               5                   10                  15
```

<210> SEQ ID NO 8
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (3)..(3)
<223> OTHER INFORMATION: Xaa is unknown or other

<400> SEQUENCE: 8

```
Lys Lys Xaa Lys
1
```

<210> SEQ ID NO 9
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (3)..(3)
<223> OTHER INFORMATION: Xaa is unknown or other

<400> SEQUENCE: 9

```
Lys Arg Xaa Lys
1
```

<210> SEQ ID NO 10
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (3)..(3)
<223> OTHER INFORMATION: Xaa is unknown or other

<400> SEQUENCE: 10

```
Lys Lys Xaa Arg
1
```

<210> SEQ ID NO 11
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: misc_feature

```
<222> LOCATION: (3)..(3)
<223> OTHER INFORMATION: Xaa is unknown or other

<400> SEQUENCE: 11

Lys Arg Xaa Arg
1

<210> SEQ ID NO 12
<211> LENGTH: 20
<212> TYPE: PRT
<213> ORGANISM: Artificial Sequence
<220> FEATURE:
<223> OTHER INFORMATION: synthetic construct

<400> SEQUENCE: 12

Ala Val Lys Arg Pro Ala Ala Thr Lys Lys Ala Gly Gln Ala Lys Lys
1               5                   10                  15

Lys Lys Leu Asp
            20

<210> SEQ ID NO 13
<211> LENGTH: 25
<212> TYPE: PRT
<213> ORGANISM: Artificial Sequence
<220> FEATURE:
<223> OTHER INFORMATION: synthetic construct

<400> SEQUENCE: 13

Met Ser Arg Arg Lys Ala Asn Pro Thr Lys Leu Ser Glu Asn Ala
1               5                   10                  15

Lys Lys Leu Ala Lys Glu Val Glu Asn
            20                  25

<210> SEQ ID NO 14
<211> LENGTH: 9
<212> TYPE: PRT
<213> ORGANISM: Artificial Sequence
<220> FEATURE:
<223> OTHER INFORMATION: synthetic construct

<400> SEQUENCE: 14

Pro Ala Ala Lys Arg Val Lys Leu Asp
1               5

<210> SEQ ID NO 15
<211> LENGTH: 8
<212> TYPE: PRT
<213> ORGANISM: Artificial Sequence
<220> FEATURE:
<223> OTHER INFORMATION: synthetic construct

<400> SEQUENCE: 15

Pro Pro Lys Lys Lys Arg Lys Val
1               5

<210> SEQ ID NO 16
<211> LENGTH: 9
<212> TYPE: PRT
<213> ORGANISM: Artificial Sequence
<220> FEATURE:
<223> OTHER INFORMATION: synthetic construct

<400> SEQUENCE: 16

Lys Leu Lys Ile Lys Arg Pro Val Lys
1               5
```

<210> SEQ ID NO 17
<211> LENGTH: 25
<212> TYPE: PRT
<213> ORGANISM: Artificial Sequence
<220> FEATURE:
<223> OTHER INFORMATION: synthetic construct

<400> SEQUENCE: 17

Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25

<210> SEQ ID NO 18
<211> LENGTH: 1368
<212> TYPE: PRT
<213> ORGANISM: Streptococcus pyogenes

<400> SEQUENCE: 18

Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Ala Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Arg Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Arg Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp

```
                290                 295                 300
Ile Leu Arg Val Asn Ser Glu Ile Thr Lys Ala Pro Leu Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
                355                 360                 365
Gln Glu Glu Phe Tyr Lys Phe Ile Lys Pro Ile Leu Glu Lys Met Asp
                370                 375                 380
Gly Thr Glu Glu Leu Leu Ala Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
Leu Lys Asp Asn Arg Glu Lys Ile Glu Lys Ile Leu Thr Phe Arg Ile
                435                 440                 445
Pro Tyr Tyr Val Gly Pro Leu Ala Arg Gly Asn Ser Arg Phe Ala Trp
                450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
                515                 520                 525
Tyr Val Thr Glu Gly Met Arg Lys Pro Glu Phe Leu Ser Gly Glu Gln
                530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
                595                 600                 605
Asn Glu Glu Asn Glu Asp Ile Leu Glu Asp Ile Val Leu Thr Leu Thr
610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
                675                 680                 685
Ala Asn Arg Asn Phe Met Gln Leu Ile His Asp Asp Ser Leu Thr Phe
                690                 695                 700
Lys Glu Asp Ile Gln Lys Ala Gln Val Ser Gly Gln Gly Asp Ser Leu
705                 710                 715                 720
```

```
His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Asp Ile Leu Lys Glu Tyr Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Ile Lys
            835                 840                 845

Asp Asp Ser Ile Asp Asn Lys Val Leu Thr Arg Ser Asp Lys Asn Arg
            850                 855                 860

Gly Lys Ser Asp Asn Val Pro Ser Glu Glu Val Val Lys Lys Met Lys
865                 870                 875                 880

Asn Tyr Trp Lys Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
            1010                1015                1020

Lys Ser Glu Gln Glu Ile Gly Lys Ala Thr Ala Lys Tyr Phe Phe
            1025                1030                1035

Tyr Ser Asn Ile Met Asn Phe Phe Lys Thr Glu Ile Thr Leu Ala
            1040                1045                1050

Asn Gly Glu Ile Arg Lys Arg Pro Leu Ile Glu Thr Asn Gly Glu
            1055                1060                1065

Thr Gly Glu Ile Val Trp Asp Lys Gly Arg Asp Phe Ala Thr Val
            1070                1075                1080

Arg Lys Val Leu Ser Met Pro Gln Val Asn Ile Val Lys Lys Thr
            1085                1090                1095

Glu Val Gln Thr Gly Gly Phe Ser Lys Glu Ser Ile Leu Pro Lys
            1100                1105                1110

Arg Asn Ser Asp Lys Leu Ile Ala Arg Lys Lys Asp Trp Asp Pro
            1115                1120                1125
```

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Arg Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Phe Gly Ala Pro Ala Ala
    1310                1315                1320

Phe Ile Tyr Phe Asp Thr Thr Ile Gly Arg Asn Arg Tyr Lys Ser
    1325                1330                1335

Ile Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 19
<211> LENGTH: 1388
<212> TYPE: PRT
<213> ORGANISM: Streptococcus thermophilus

<400> SEQUENCE: 19

Met Thr Lys Pro Tyr Ser Ile Gly Leu Asp Ile Gly Thr Asn Ser Val
1               5                   10                  15

Gly Trp Ala Val Thr Thr Asp Asn Tyr Lys Val Pro Ser Lys Lys Met
            20                  25                  30

Lys Val Leu Gly Asn Thr Ser Lys Lys Tyr Ile Lys Lys Asn Leu Leu
        35                  40                  45

Gly Val Leu Leu Phe Asp Ser Gly Ile Thr Ala Glu Gly Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Thr Glu Met Ala Thr Leu Asp Asp Ala
                85                  90                  95

Phe Phe Gln Arg Leu Asp Asp Ser Phe Leu Val Pro Asp Asp Lys Arg
            100                 105                 110

Asp Ser Lys Tyr Pro Ile Phe Gly Asn Leu Val Glu Glu Lys Ala Tyr
        115                 120                 125

```
His Asp Glu Phe Pro Thr Ile Tyr His Leu Arg Lys Tyr Leu Ala Asp
    130                 135                 140

Ser Thr Lys Lys Ala Asp Leu Arg Leu Val Tyr Leu Ala Leu Ala His
145                 150                 155                 160

Met Ile Lys Tyr Arg Gly His Phe Leu Ile Glu Gly Glu Phe Asn Ser
                165                 170                 175

Lys Asn Asn Asp Ile Gln Lys Asn Phe Gln Asp Phe Leu Asp Thr Tyr
            180                 185                 190

Asn Ala Ile Phe Glu Ser Asp Leu Ser Leu Glu Asn Ser Lys Gln Leu
        195                 200                 205

Glu Glu Ile Val Lys Asp Lys Ile Ser Lys Leu Glu Lys Lys Asp Arg
    210                 215                 220

Ile Leu Lys Leu Phe Pro Gly Glu Lys Asn Ser Gly Ile Phe Ser Glu
225                 230                 235                 240

Phe Leu Lys Leu Ile Val Gly Asn Gln Ala Asp Phe Arg Lys Cys Phe
                245                 250                 255

Asn Leu Asp Glu Lys Ala Ser Leu His Phe Ser Lys Glu Ser Tyr Asp
            260                 265                 270

Glu Asp Leu Glu Thr Leu Leu Gly Tyr Ile Gly Asp Asp Tyr Ser Asp
        275                 280                 285

Val Phe Leu Lys Ala Lys Lys Leu Tyr Asp Ala Ile Leu Leu Ser Gly
    290                 295                 300

Phe Leu Thr Val Thr Asp Asn Glu Thr Glu Ala Pro Leu Ser Ser Ala
305                 310                 315                 320

Met Ile Lys Arg Tyr Asn Glu His Lys Glu Asp Leu Ala Leu Leu Lys
                325                 330                 335

Glu Tyr Ile Arg Asn Ile Ser Leu Lys Thr Tyr Asn Glu Val Phe Lys
            340                 345                 350

Asp Asp Thr Lys Asn Gly Tyr Ala Gly Tyr Ile Asp Gly Lys Thr Asn
        355                 360                 365

Gln Glu Asp Phe Tyr Val Tyr Leu Lys Lys Leu Leu Ala Glu Phe Glu
    370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
                405                 410                 415

Gln Glu Met Arg Ala Ile Leu Asp Lys Gln Ala Lys Phe Tyr Pro Phe
            420                 425                 430

Leu Ala Lys Asn Lys Glu Arg Ile Glu Lys Ile Leu Thr Phe Arg Ile
        435                 440                 445

Pro Tyr Tyr Val Gly Pro Leu Ala Arg Gly Asn Ser Asp Phe Ala Trp
    450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
                485                 490                 495

Ser Phe Asp Leu Tyr Leu Pro Glu Glu Lys Val Leu Pro Lys His Ser
            500                 505                 510

Leu Leu Tyr Glu Thr Phe Asn Val Tyr Asn Glu Leu Thr Lys Val Arg
        515                 520                 525

Phe Ile Ala Glu Ser Met Arg Asp Tyr Gln Phe Leu Asp Ser Lys Gln
    530                 535                 540
```

```
Lys Lys Asp Ile Val Arg Leu Tyr Phe Lys Asp Lys Arg Lys Val Thr
545                 550                 555                 560

Asp Lys Asp Ile Ile Glu Tyr Leu His Ala Ile Tyr Gly Tyr Asp Gly
                565                 570                 575

Ile Glu Leu Lys Gly Ile Glu Lys Gln Phe Asn Ser Ser Leu Ser Thr
            580                 585                 590

Tyr His Asp Leu Leu Asn Ile Ile Asn Asp Lys Glu Phe Leu Asp Asp
        595                 600                 605

Ser Ser Asn Glu Ala Ile Ile Glu Glu Ile Ile His Thr Leu Thr Ile
    610                 615                 620

Phe Glu Asp Arg Glu Met Ile Lys Gln Arg Leu Ser Lys Phe Glu Asn
625                 630                 635                 640

Ile Phe Asp Lys Ser Val Leu Lys Lys Leu Ser Arg Arg His Tyr Thr
                645                 650                 655

Gly Trp Gly Lys Leu Ser Ala Lys Leu Ile Asn Gly Ile Arg Asp Glu
            660                 665                 670

Lys Ser Gly Asn Thr Ile Leu Asp Tyr Leu Ile Asp Asp Gly Ile Ser
        675                 680                 685

Asn Arg Asn Phe Met Gln Leu Ile His Asp Asp Ala Leu Ser Phe Lys
    690                 695                 700

Lys Lys Ile Gln Lys Ala Gln Ile Ile Gly Asp Glu Asp Lys Gly Asn
705                 710                 715                 720

Ile Lys Glu Val Val Lys Ser Leu Pro Gly Ser Pro Ala Ile Lys Lys
                725                 730                 735

Gly Ile Leu Gln Ser Ile Lys Ile Val Asp Glu Leu Val Lys Val Met
            740                 745                 750

Gly Gly Arg Lys Pro Glu Ser Ile Val Val Glu Met Ala Arg Glu Asn
        755                 760                 765

Gln Tyr Thr Asn Gln Gly Lys Ser Asn Ser Gln Gln Arg Leu Lys Arg
    770                 775                 780

Leu Glu Lys Ser Leu Lys Glu Leu Gly Ser Lys Ile Leu Lys Glu Asn
785                 790                 795                 800

Ile Pro Ala Lys Leu Ser Lys Ile Asp Asn Asn Ala Leu Gln Asn Asp
                805                 810                 815

Arg Leu Tyr Leu Tyr Tyr Leu Gln Asn Gly Lys Asp Met Tyr Thr Gly
            820                 825                 830

Asp Asp Leu Asp Ile Asp Arg Leu Ser Asn Tyr Asp Ile Asp His Ile
        835                 840                 845

Ile Pro Gln Ala Phe Leu Lys Asp Asn Ser Ile Asp Asn Lys Val Leu
    850                 855                 860

Val Ser Ser Ala Ser Asn Arg Gly Lys Ser Asp Asp Val Pro Ser Leu
865                 870                 875                 880

Glu Val Val Lys Lys Arg Lys Thr Phe Trp Tyr Gln Leu Leu Lys Ser
                885                 890                 895

Lys Leu Ile Ser Gln Arg Lys Phe Asp Asn Leu Thr Lys Ala Glu Arg
            900                 905                 910

Gly Gly Leu Ser Pro Glu Asp Lys Ala Gly Phe Ile Gln Arg Gln Leu
        915                 920                 925

Val Glu Thr Arg Gln Ile Thr Lys His Val Ala Arg Leu Leu Asp Glu
    930                 935                 940

Lys Phe Asn Asn Lys Lys Asp Glu Asn Asn Arg Ala Val Arg Thr Val
945                 950                 955                 960

Lys Ile Ile Thr Leu Lys Ser Thr Leu Val Ser Gln Phe Arg Lys Asp
```

```
                965                 970                 975
Phe Glu Leu Tyr Lys Val Arg Glu Ile Asn Asp Phe His His Ala His
                980                 985                 990
Asp Ala Tyr Leu Asn Ala Val Val Ala Ser Ala Leu Leu Lys Lys Tyr
                995                1000                1005
Pro Lys Leu Glu Pro Glu Phe Val Tyr Gly Asp Tyr Pro Lys Tyr
       1010                1015                1020
Asn Ser Phe Arg Glu Arg Lys Ser Ala Thr Glu Lys Val Tyr Phe
       1025                1030                1035
Tyr Ser Asn Ile Met Asn Ile Phe Lys Lys Ser Ile Ser Leu Ala
       1040                1045                1050
Asp Gly Arg Val Ile Glu Arg Pro Leu Ile Glu Val Asn Glu Glu
       1055                1060                1065
Thr Gly Glu Ser Val Trp Asn Lys Glu Ser Asp Leu Ala Thr Val
       1070                1075                1080
Arg Arg Val Leu Ser Tyr Pro Gln Val Asn Val Val Lys Lys Val
       1085                1090                1095
Glu Glu Gln Asn His Gly Leu Asp Arg Gly Lys Pro Lys Gly Leu
       1100                1105                1110
Phe Asn Ala Asn Leu Ser Ser Lys Pro Lys Pro Asn Ser Asn Glu
       1115                1120                1125
Asn Leu Val Gly Ala Lys Glu Tyr Leu Asp Pro Lys Lys Tyr Gly
       1130                1135                1140
Gly Tyr Ala Gly Ile Ser Asn Ser Phe Thr Val Leu Val Lys Gly
       1145                1150                1155
Thr Ile Glu Lys Gly Ala Lys Lys Lys Ile Thr Asn Val Leu Glu
       1160                1165                1170
Phe Gln Gly Ile Ser Ile Leu Asp Arg Ile Asn Tyr Arg Lys Asp
       1175                1180                1185
Lys Leu Asn Phe Leu Leu Glu Lys Gly Tyr Lys Asp Ile Glu Leu
       1190                1195                1200
Ile Ile Glu Leu Pro Lys Tyr Ser Leu Phe Glu Leu Ser Asp Gly
       1205                1210                1215
Ser Arg Arg Met Leu Ala Ser Ile Leu Ser Thr Asn Asn Lys Arg
       1220                1225                1230
Gly Glu Ile His Lys Gly Asn Gln Ile Phe Leu Ser Gln Lys Phe
       1235                1240                1245
Val Lys Leu Leu Tyr His Ala Lys Arg Ile Ser Asn Thr Ile Asn
       1250                1255                1260
Glu Asn His Arg Lys Tyr Val Glu Asn His Lys Lys Glu Phe Glu
       1265                1270                1275
Glu Leu Phe Tyr Tyr Ile Leu Glu Phe Asn Glu Asn Tyr Val Gly
       1280                1285                1290
Ala Lys Lys Asn Gly Lys Leu Leu Asn Ser Ala Phe Gln Ser Trp
       1295                1300                1305
Gln Asn His Ser Ile Asp Glu Leu Cys Ser Ser Phe Ile Gly Pro
       1310                1315                1320
Thr Gly Ser Glu Arg Lys Gly Leu Phe Glu Leu Thr Ser Arg Gly
       1325                1330                1335
Ser Ala Ala Asp Phe Glu Phe Leu Gly Val Lys Ile Pro Arg Tyr
       1340                1345                1350
Arg Asp Tyr Thr Pro Ser Ser Leu Leu Lys Asp Ala Thr Leu Ile
       1355                1360                1365
```

His Gln Ser Val Thr Gly Leu Tyr Glu Thr Arg Ile Asp Leu Ala
    1370                1375                1380

Lys Leu Gly Glu Gly
    1385

<210> SEQ ID NO 20
<211> LENGTH: 23
<212> TYPE: PRT
<213> ORGANISM: Artificial Sequence
<220> FEATURE:
<223> OTHER INFORMATION: synthetic construct
<220> FEATURE:
<221> NAME/KEY: N
<222> LOCATION: (9)..(20)
<223> OTHER INFORMATION: N is A, G, T, or C
<220> FEATURE:
<221> NAME/KEY: misc_feature
<222> LOCATION: (21)..(21)
<223> OTHER INFORMATION: Xaa is unknown or other

<400> SEQUENCE: 20

Met Met Met Met Met Met Met Met Asn Asn Asn Asn Asn Asn Asn
1               5                   10                  15

Asn Asn Asn Asn Xaa Gly Gly
            20

<210> SEQ ID NO 21
<211> LENGTH: 27
<212> TYPE: PRT
<213> ORGANISM: Artificial Sequence
<220> FEATURE:
<223> OTHER INFORMATION: synthetic construct
<220> FEATURE:
<221> NAME/KEY: N
<222> LOCATION: (8)..(20)
<223> OTHER INFORMATION: N is A, G, T, or C
<220> FEATURE:
<221> NAME/KEY: misc_feature
<222> LOCATION: (21)..(22)
<223> OTHER INFORMATION: Xaa is unknown or other

<400> SEQUENCE: 21

Met Met Met Met Met Met Met Met Asn Asn Asn Asn Asn Asn Asn
1               5                   10                  15

Asn Asn Asn Asn Xaa Xaa Ala Gly Ala Ala Trp
            20                  25

<210> SEQ ID NO 22
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: N
<222> LOCATION: (9)..(20)
<223> OTHER INFORMATION: N is A, G, T, or C
<220> FEATURE:
<221> NAME/KEY: misc_feature
<222> LOCATION: (21)..(21)
<223> OTHER INFORMATION: Xaa is unknown or other
<220> FEATURE:
<221> NAME/KEY: misc_feature
<222> LOCATION: (24)..(24)
<223> OTHER INFORMATION: Xaa is unknown or other

<400> SEQUENCE: 22

Met Met Met Met Met Met Met Met Asn Asn Asn Asn Asn Asn Asn
1               5                   10                  15

```
Asn Asn Asn Asn Xaa Gly Gly Xaa Gly
            20              25

<210> SEQ ID NO 23
<211> LENGTH: 104
<212> TYPE: PRT
<213> ORGANISM: Homo sapiens

<400> SEQUENCE: 23

Met Asp Val Thr Ile Gln His Pro Trp Phe Lys Arg Thr Leu Gly Pro
1               5                   10                  15

Phe Tyr Pro Ser Arg Leu Phe Asp Gln Phe Phe Gly Glu Gly Leu Phe
            20                  25                  30

Glu Tyr Asp Leu Leu Pro Phe Leu Ser Ser Thr Ile Ser Pro Tyr Tyr
        35                  40                  45

Arg Gln Ser Leu Phe Arg Thr Val Leu Asp Ser Gly Ile Ser Glu Val
    50                  55                  60

Arg Ser Asp Arg Asp Lys Phe Val Ile Phe Leu Asp Val Lys His Phe
65                  70                  75                  80

Ser Pro Glu Asp Leu Thr Val Lys Val Gln Asp Asp Phe Val Glu Ile
                85                  90                  95

His Gly Lys His Asn Glu Arg Gln
            100

<210> SEQ ID NO 24
<211> LENGTH: 175
<212> TYPE: PRT
<213> ORGANISM: Homo sapiens

<400> SEQUENCE: 24

Met Asp Ile Ala Ile His His Pro Trp Ile His Arg Pro Phe Phe Pro
1               5                   10                  15

Phe His Ser Pro Ser Arg Leu Phe Asp Gln Phe Phe Gly Glu His Leu
            20                  25                  30

Leu Glu Ser Asp Leu Phe Pro Thr Ser Thr Ser Leu Ser Pro Phe Tyr
        35                  40                  45

Leu Arg Pro Pro Ser Phe Leu Arg Ala Pro Ser Trp Phe Asp Thr Gly
    50                  55                  60

Leu Ser Glu Met Arg Leu Glu Lys Asp Arg Phe Ser Val Asn Leu Asp
65                  70                  75                  80

Val Lys His Phe Ser Pro Glu Glu Leu Lys Val Lys Val Leu Gly Asp
                85                  90                  95

Val Ile Glu Val His Gly Lys His Glu Glu Arg Gln Asp Glu His Gly
            100                 105                 110

Phe Ile Ser Arg Glu Phe His Arg Lys Tyr Arg Ile Pro Ala Asp Val
        115                 120                 125

Asp Pro Leu Thr Ile Thr Ser Ser Leu Ser Ser Asp Gly Val Leu Thr
    130                 135                 140

Val Asn Gly Pro Arg Lys Gln Val Ser Gly Pro Glu Arg Thr Ile Pro
145                 150                 155                 160

Ile Thr Arg Glu Glu Lys Pro Ala Val Thr Ala Ala Pro Lys Lys
                165                 170                 175

<210> SEQ ID NO 25
<211> LENGTH: 173
<212> TYPE: PRT
<213> ORGANISM: Artificial Sequence
```

```
<220> FEATURE:
<223> OTHER INFORMATION: synthetic construct

<400> SEQUENCE: 25

Met Asp Ile Ala Ile Gln His Pro Trp Phe Lys Arg Thr Leu Gly Pro
1               5                   10                  15

Phe Tyr Pro Ser Arg Leu Phe Asp Gln Phe Gly Glu Gly Leu Phe
            20                  25                  30

Glu Tyr Asp Leu Leu Pro Phe Leu Ser Ser Thr Ile Ser Pro Tyr Tyr
        35                  40                  45

Arg Gln Ser Leu Phe Arg Thr Val Leu Asp Ser Gly Ile Ser Glu Val
    50                  55                  60

Arg Ser Asp Arg Asp Lys Phe Val Ile Phe Leu Asp Val Lys His Phe
65                  70                  75                  80

Ser Pro Glu Asp Leu Thr Val Lys Val Gln Glu Asp Phe Val Glu Ile
                85                  90                  95

His Gly Lys His Asn Glu Arg Gln Asp Asp His Gly Tyr Ile Ser Arg
            100                 105                 110

Glu Phe His Arg Arg Tyr Arg Leu Pro Ser Asn Val Asp Gln Ser Ala
        115                 120                 125

Leu Ser Cys Ser Leu Ser Ala Asp Gly Met Leu Thr Phe Ser Gly Pro
    130                 135                 140

Lys Ile Pro Ser Gly Val Asp Ala Gly His Ser Glu Arg Ala Ile Pro
145                 150                 155                 160

Val Ser Arg Glu Glu Lys Pro Ser Ser Ala Pro Ser Ser
                165                 170

<210> SEQ ID NO 26
<211> LENGTH: 175
<212> TYPE: PRT
<213> ORGANISM: Artificial Sequence
<220> FEATURE:
<223> OTHER INFORMATION: synthetic construct

<400> SEQUENCE: 26

Met Asp Ile Ala Ile His His Pro Trp Ile Arg Arg Pro Phe Phe Pro
1               5                   10                  15

Phe His Ser Pro Ser Arg Leu Phe Asp Gln Phe Phe Gly Glu His Leu
            20                  25                  30

Leu Glu Ser Asp Leu Phe Pro Ala Ser Thr Ser Leu Ser Pro Phe Tyr
        35                  40                  45

Leu Arg Pro Pro Ser Phe Leu Arg Ala Pro Ser Trp Ile Asp Thr Gly
    50                  55                  60

Leu Ser Glu Met Arg Leu Glu Lys Asp Arg Phe Ser Val Asn Leu Asp
65                  70                  75                  80

Val Lys His Phe Ser Pro Glu Glu Leu Lys Val Lys Val Leu Gly Asp
                85                  90                  95

Val Ile Glu Val His Gly Lys His Glu Glu Arg Gln Asp Glu His Gly
            100                 105                 110

Phe Ile Ser Arg Glu Phe His Arg Lys Tyr Arg Ile Pro Ala Asp Val
        115                 120                 125

Asp Pro Leu Ala Ile Thr Ser Ser Leu Ser Ser Asp Gly Val Leu Thr
    130                 135                 140

Val Asn Gly Pro Arg Lys Gln Ala Ser Gly Pro Glu Arg Thr Ile Pro
145                 150                 155                 160

Ile Thr Arg Glu Glu Lys Pro Ala Val Thr Ala Ala Pro Lys Lys
```

```
                                165                 170                 175

<210> SEQ ID NO 27
<211> LENGTH: 173
<212> TYPE: PRT
<213> ORGANISM: Artificial Sequence
<220> FEATURE:
<223> OTHER INFORMATION: synthetic construct

<400> SEQUENCE: 27

Met Asp Val Thr Ile Gln His Pro Trp Phe Lys Arg Thr Leu Gly Pro
1               5                   10                  15

Phe Tyr Pro Ser Arg Leu Phe Asp Gln Phe Gly Glu Gly Leu Phe
            20                  25                  30

Glu Tyr Asp Leu Leu Pro Phe Leu Ser Ser Thr Ile Ser Pro Tyr Tyr
            35                  40                  45

Arg Gln Ser Leu Phe Arg Thr Val Leu Asp Ser Gly Ile Ser Glu Val
        50                  55                  60

Arg Ser Asp Arg Asp Lys Phe Val Ile Phe Leu Asp Val Lys His Phe
65                  70                  75                  80

Ser Pro Glu Asp Leu Thr Val Lys Val Gln Asp Asp Phe Val Glu Ile
                85                  90                  95

His Gly Lys His Asn Glu Arg Gln Asp Asp His Gly Tyr Ile Ser Arg
            100                 105                 110

Glu Phe His Arg Arg Tyr Arg Leu Pro Ser Asn Val Asp Gln Ser Ala
        115                 120                 125

Leu Ser Cys Ser Leu Ser Ala Asp Gly Met Leu Thr Phe Cys Gly Pro
    130                 135                 140

Lys Ile Gln Thr Gly Leu Asp Ala Thr His Ala Glu Arg Ala Ile Pro
145                 150                 155                 160

Val Ser Arg Glu Glu Lys Pro Thr Ser Ala Pro Ser Ser
                165                 170

<210> SEQ ID NO 28
<211> LENGTH: 175
<212> TYPE: PRT
<213> ORGANISM: Artificial Sequence
<220> FEATURE:
<223> OTHER INFORMATION: synthetic construct

<400> SEQUENCE: 28

Met Asp Ile Ala Ile His His Pro Trp Ile Arg Arg Pro Phe Phe Pro
1               5                   10                  15

Phe His Ser Pro Ser Arg Leu Phe Asp Gln Phe Phe Gly Glu His Leu
            20                  25                  30

Leu Glu Ser Asp Leu Phe Pro Thr Ser Thr Ser Leu Ser Pro Phe Tyr
            35                  40                  45

Leu Arg Pro Pro Ser Phe Leu Arg Ala Pro Ser Trp Phe Asp Thr Gly
        50                  55                  60

Leu Ser Glu Met Arg Leu Glu Lys Asp Arg Phe Ser Val Asn Leu Asp
65                  70                  75                  80

Val Lys His Phe Ser Pro Glu Glu Leu Lys Val Lys Val Leu Gly Asp
                85                  90                  95

Val Ile Glu Val His Gly Lys His Glu Glu Arg Gln Asp Glu His Gly
            100                 105                 110

Phe Ile Ser Arg Glu Phe His Arg Lys Tyr Arg Ile Pro Ala Asp Val
        115                 120                 125
```

```
Asp Pro Leu Thr Ile Thr Ser Ser Leu Ser Ser Asp Gly Val Leu Thr
            130                 135                 140

Val Asn Gly Pro Arg Lys Gln Val Ser Gly Pro Glu Arg Thr Ile Pro
145                 150                 155                 160

Ile Thr Arg Glu Glu Lys Pro Ala Val Thr Ala Ala Pro Lys Lys
                165                 170                 175

<210> SEQ ID NO 29
<211> LENGTH: 173
<212> TYPE: PRT
<213> ORGANISM: Artificial Sequence
<220> FEATURE:
<223> OTHER INFORMATION: synthetic construct

<400> SEQUENCE: 29

Met Asp Val Thr Ile Gln His Pro Trp Phe Lys Arg Thr Leu Gly Pro
1               5                   10                  15

Phe Tyr Pro Ser Arg Leu Phe Asp Gln Phe Phe Gly Glu Gly Leu Phe
                20                  25                  30

Glu Tyr Asp Leu Leu Pro Phe Leu Ser Ser Thr Ile Ser Pro Tyr Tyr
            35                  40                  45

Arg Gln Ser Leu Phe Arg Thr Val Leu Asp Ser Gly Ile Ser Glu Val
    50                  55                  60

Arg Ser Asp Arg Asp Lys Phe Val Ile Phe Leu Asp Val Lys His Phe
65                  70                  75                  80

Ser Pro Glu Asp Leu Thr Val Lys Val Gln Asp Asp Phe Val Glu Ile
                85                  90                  95

His Gly Lys His Asn Glu Arg Gln Asp Asp His Gly Tyr Ile Ser Arg
            100                 105                 110

Glu Phe His Arg Arg Tyr Arg Leu Pro Ser Asn Val Asp Gln Ser Ala
        115                 120                 125

Leu Ser Cys Ser Leu Ser Ala Asp Gly Met Leu Thr Phe Cys Gly Pro
    130                 135                 140

Lys Ile Gln Thr Gly Leu Asp Ala Thr His Ala Glu Arg Ala Ile Pro
145                 150                 155                 160

Val Ser Arg Glu Glu Lys Pro Thr Ser Ala Pro Ser Ser
                165                 170

<210> SEQ ID NO 30
<211> LENGTH: 175
<212> TYPE: PRT
<213> ORGANISM: Artificial Sequence
<220> FEATURE:
<223> OTHER INFORMATION: synthetic construct

<400> SEQUENCE: 30

Met Asp Ile Ala Ile His His Pro Trp Ile Arg Arg Pro Phe Phe Pro
1               5                   10                  15

Phe His Ser Pro Ser Arg Leu Phe Asp Gln Phe Phe Gly Glu His Leu
                20                  25                  30

Leu Glu Ser Asp Leu Phe Pro Thr Ser Thr Ser Leu Ser Pro Phe Tyr
            35                  40                  45

Leu Arg Pro Pro Ser Phe Leu Arg Ala Pro Ser Trp Phe Asp Thr Gly
    50                  55                  60

Leu Ser Glu Met Arg Leu Glu Lys Asp Arg Phe Ser Val Asn Leu Asp
65                  70                  75                  80

Val Lys His Phe Ser Pro Glu Glu Leu Lys Val Lys Val Leu Gly Asp
                85                  90                  95
```

-continued

```
Val Ile Glu Val His Gly Lys His Glu Glu Arg Gln Asp Glu His Gly
                100                 105                 110

Phe Ile Ser Arg Glu Phe His Arg Lys Tyr Arg Ile Pro Ala Asp Val
            115                 120                 125

Asp Pro Leu Thr Ile Thr Ser Ser Leu Ser Ser Asp Gly Val Leu Thr
        130                 135                 140

Val Asn Gly Pro Arg Lys Gln Val Ser Gly Pro Glu Arg Thr Ile Pro
145                 150                 155                 160

Ile Thr Arg Glu Glu Lys Pro Ala Val Thr Ala Ala Pro Lys Lys
                165                 170                 175
```